(12) United States Patent
Gymer et al.

(10) Patent No.: US 6,979,690 B2
(45) Date of Patent: Dec. 27, 2005

(54) OXO OR OXY-PYRIDINE COMPOUNDS AS 5-HT4 RECEPTOR MODULATORS

(75) Inventors: Geoffrey Gymer, Sandwich (GB); Kiyoshi Kawamura, Aichi-ken (JP); Sachiko Mihara, Aichi-ken (JP); Mikio Morita, Aichi-ken (JP); Alan Stobie, Sandwich (GB); Chikara Uchida, Aichi-ken (JP); Seiji Nukui, Aichi-ken (JP)

(73) Assignee: Pfizer Inc., New York, NY (US)

( * ) Notice: Subject to any disclaimer, the term of this patent is extended or adjusted under 35 U.S.C. 154(b) by 194 days.

(21) Appl. No.: 10/337,497

(22) Filed: Jan. 7, 2003

(65) Prior Publication Data

US 2003/0207875 A1    Nov. 6, 2003

Related U.S. Application Data

(60) Provisional application No. 60/346,747, filed on Jan. 7, 2002.

(51) Int. Cl.[7] .................... A61K 31/445; C07D 401/12
(52) U.S. Cl. ................. 514/318; 514/235.5; 514/255; 544/124; 544/360; 546/139; 546/193; 546/208
(58) Field of Search .................... 514/318, 235.5, 514/255; 546/193, 139, 208; 544/124, 360

(56) References Cited

U.S. PATENT DOCUMENTS

| | | | |
|---|---|---|---|
| 5,137,893 A | 8/1992 | Becker et al. | 514/293 |
| 5,219,850 A | 6/1993 | Becker et al. | 514/214 |
| 5,434,161 A | 7/1995 | Becker et al. | 514/300 |
| 5,591,749 A | 1/1997 | Becker et al. | 514/300 |
| 5,604,239 A | 2/1997 | Becker et al. | 514/300 |
| 5,864,039 A * | 1/1999 | Kawakita et al. | 546/229 |
| 5,968,965 A | 10/1999 | Dinsmore et al. | 514/399 |

FOREIGN PATENT DOCUMENTS

| | | | |
|---|---|---|---|
| EP | 0504679 | 9/1992 | C07D 519/00 |
| EP | 0274867 | 4/1994 | C07D 233/60 |
| EP | 1217000 | 6/2002 | C07D 401/00 |
| JP | HEI 1-258674 | 10/1989 | C07D 453/02 |
| JP | 0967347 | 11/1997 | C07D 223/12 |
| JP | 10203987 | 4/1998 | A61K 31/55 |
| JP | 2001 6877 | 1/2001 | H05B 33/14 |
| WO | WO 9100858 | 1/1991 | C07D 233/60 |
| WO | WO 9215593 | 9/1992 | C07D 519/00 |
| WO | WO 9308185 | 4/1993 | C07D 451/04 |
| WO | WO 9407859 | 4/1994 | C07D 213/80 |

(Continued)

OTHER PUBLICATIONS

Tapia et al. "2,3-dihydro-2-oxo . . . " CA 131:184899 (1999).*
Courtemanche et al. "Polyfluoroalkyl . . . " CA 135:226993 (2001).*

Trilateral Project B3b :comparative sudy on reach-through claims (2001).*

(Continued)

*Primary Examiner*—Celia Chang
(74) *Attorney, Agent, or Firm*—Gregg C. Benson; Frank W. Forman

(57) ABSTRACT

This invention provides compounds of the formula (I) and (II):

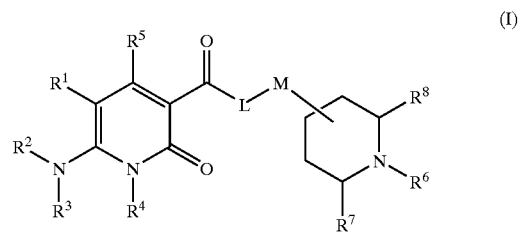

(I)

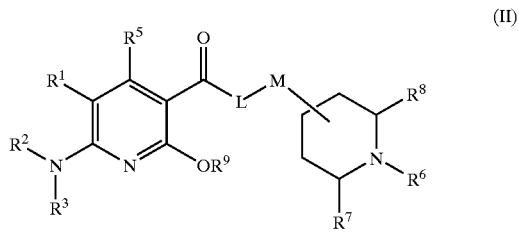

(II)

or the pharmaceutically acceptable esters thereof, and the pharmaceutically acceptable salts thereof: wherein $R^1$ is hydrogen or halo; $R^2$ and $R^3$ are independently hydrogen or $C_{1-6}$ alkyl; $R^4$ and $R^5$ are independently hydrogen or $C_{1-6}$ alkyl; $R^6$ is hydrogen, $C_{1-12}$ alkyl, $C_{1-6}$ alkoxy ($C_{1-6}$)alkyl or $C_{1-12}$ alkyl substituted by up to 3 substituents selected from the groups consisting of $C_{3-8}$ cycloalkyl, aryl, heteroaryl and heterocyclic; $R^7$ and $R^8$ are hydrogen or taken together may form alkylene chain having one or two carbon atoms; $R^9$ is $C_{1-6}$ alkyl or $C_{3-8}$ cycloalkyl; $R^{10}$ is $C_{1-6}$ alkyl or $NR^{11}R^{12}$; L is $(CR^{11}R^{12})_n$ or $NR^{11}$; M is $NR^{11}$ or $(CR^{11}R^{12})_n$; $R^{11}$ and $R^{12}$ are independently hydrogen or $C_{1-6}$ alkyl; n is an integer from 0 to 5; and m is an integer from 0 to 2; said heterocyclic, aryl and heteroaryl are unsubstituted or are substituted by at least one substituent selected from the group consisting of halo and $C_{1-6}$ alkyl; with the proviso that when $R^9$ is $C_{1-6}$ alkyl, L is not $NR^{11}$.

These compounds have 5-HT$_4$ receptor binding activity, and thus are useful for the treatment of gastroesophageal reflux disease, non-ulcer dyspepsia, irritable bowel syndrome or the like in mammalian, especially humans. This invention also provides a pharmaceutical composition comprising the above compound.

11 Claims, No Drawings

FOREIGN PATENT DOCUMENTS

| WO | WO 9408998 | 4/1994 | ......... C07D 471/04 |
|----|------------|--------|------------------------|
| WO | WO 9605166 | 2/1996 | ......... C07C 211/35 |
| WO | WO 9631475 | 10/1996 | ......... C07D 213/38 |
| WO | WO 9727852 | 8/1997 | ........ A61K 31/415 |
| WO | WO 9738665 | 10/1997 | |
| WO | WO 9950247 | 10/1999 | ......... C07D 211/14 |
| WO | WO 9950264 | 10/1999 | ......... C07D 401/14 |
| WO | WO 0105763 | 1/2001 | ......... C07D 211/00 |
| WO | WO 0114331 | 3/2001 | ......... C07D 211/00 |

OTHER PUBLICATIONS

Dumuis, et al., "A 5HT Receptor in the Central Nervous System, Positively Coupled with Adnylate Cyclase, is Antagonized by ICS 205 930", Eur. J. of Pharmacology, 146, pp. 187-188 (1988).

Dumuis, et al. "The Gastrointestinal Prokinetic Benzamide Derivatives are Agonists at the Non-classical 5-HT Receptor (5-HT$_4$) Positively Coupled to Adenylate Cyclase in Neurons", Naunyn-Schmiedeberg's Archives of Pharmacology, 340, 403-410 (1989).

Bockaert, et al., "The 5-HT$_4$ Receptor: A Place in the Sun" TiPs Reviews, vol. 13, pp. 141-145 (1992).

Ford, et al., "The 5-HT$_4$ Receptor", Medicinal Research Reviews, vol. 13 (6), pp. 633-662 (1993).

Gullikson, et al., "Gastrointestinal Motility Responses to the S and R Enantiomers of Zacopride, a 5-HT4 Agonist and 5-HT3 Antagonist", Drug Development Research, 26, pp. 405-417 (1992).

Eglen, et al., "Central 5-HT$_4$ Receptors", TiPS Review, 16, pp. 391-398 (1995).

Bockaert, et al., "5-HT4 Receptors", CNS Drugs, 1(1), pp. 6-15 (1994).

Romanelli, et al., "Synthesis and Biological Activity of a Series of Aryl Tropanyl Esters and Amides Chemically Related to 1H-Indole-3-carboxylic Acid endo 8-Methyl-8-azabicyclo[3.2.1]oct-3-yl Ester", Arzneim-Forsch./Drug. Res. 43 (II) (8), pp. 913-918 (1993).

Kaumann, et al., "A 5-HT$_4$-like Receptor in Human Right Atrium", Naunyn-Schmiedeberg's Archives of Pharmacology, 344, pp. 150-159 (1991).

Mutterer, et al., "Haologenated pyridines v. fluorinated and brominated pyridine compounds", Helvetica Chimica Acta, 59, Fasc. 1 (1976) No. 23-24, pp. 229-235 (Translation of German Article).

Barlow, et al., "Diels-Alder reactions of trichloro-1,2,4-triazine: intramolecular additions with 1,5 and 1,6 dienes", J. Chem. Soc., Perkin Trans. 1, pp 519-524 (1995).

Lantos, et al., "Novel Cage Compounds from Inter-intramolecular Diels-Alder Reactions of 1,2,4-Triazines with Cyclo-octa-1,5-diene", J. Chem. Socl, Chem. Commun., pp. 1482-1483 (1988).

Greene, et al., "Protection for the Hydroxyl Group, including 1,2-and 1,3-Diols", Protective Groups in Organic Synthesis, 2$^{nd}$ Edition, pp. 10-142 (1991).

Greene, et al., "Protection for the Amino Group", Protective Groups in Organic Synthesis, 2$^{nd}$ Edition, pp. 309-405 (1991).

Greene, et al., "Protection for the Carboxyl Group", Protective Groups in Organic Synthesis, 3$^{rd}$ Edition, pp. 369-377.

Feibush, et al., "Chirah Separation of Heterocyclic Drugs by HPLC: Solute-Stationary Phase Base-Pair Interactions", J. Am. Chem. Soc., 108, pp. 3310-3318 (1986).

Baxter, et al., 5-Hydroxytryptamine, receptors mediate relaxation of the rat oesophageal tunica muscularis mucosae, Naunyn-Schmiedeberg's Archives of Pharmacology, 343, pp. 439-446 (1991).

Mine, et al., "Comparison of Effect of Mosapride Citrate and Existing 5-HT$_4$ Receptor Agonists on Gastrointestinal Motility in Vivo and in Vitro ", JPET, 283 (3), pp. 1000-1008 (1997).

Reeves, et al., "Investigation into the 5-hydroxytryptamine receptor mediating smooth muscle relaxation in the rat oesophagus", Br. J. Pharmacol., 103, pp. 1067-1072 (1991).

Coldwell, et al., "The Synthesis, and Dopamine D$_2$ and Serotonin 5-HT$_3$ Receptor Affinity of 3-Aza Analogues (Pyridyl) of 4-Amino-5-chloro-2-methoxybenzamides", Bioorganic & Medicinal Chemistry Letters, 5 (1), pp. 39-42 (1995).

Itoh, et al., "Synthesis and pharmacological evaluation of carboxamide derivatives as selective serotoninergic 5-HT$_4$ receptor agonists", Eur. J. Med. Chem. 34, pp. 977-989 (1999).

Grob, et al., "Polar Substituent Effects in the Solvolysis of Primary and Tertiary Alkyl Halides, Polar Effect IX", Helvetica Chimica Acta, 63, Fasc. 8, pp. 2152-2158 (1980).

Prugh, et al., "A Simple Method of Protecting a Secondary Amine with tert Butyloxycarbonyl (BOC) in the Presence of a Primary Amine", Synthetic Communications, 22 (16), pp. 2357-2360 (1992).

Kimpe, et al., "A Convenient Synthesis of 1-Chloro-2-alkanones", Synthesis, 2, pp. 188-190 (1987).

Blanco, et al., "Halogenation of Enol Silyl Ethers. Synthesis of Various Types of α-Bromocarbonyl Compounds", Synthesis, pp. 194-196 (1976).

Lopez-Rodriguez, et al., "Benzimidazole Derivatives. Part 1: Synthesis and Structure-Activity Relationships of New Benzimidazole-4-carboxamides and Carboxylates as Potent and Selective 5-HT$_4$ Receptor Antagonists", Bioorganic & Medicinal Chemistry, 7, pp. 2271-2281 (1999).

Klein, et al., "Design of a New Class of Orally Active Fibrinogen Receptor Antagonists", J. Med. Chem., 41, pp. 2492-2502 (1998).

Turner, "Regiospecific Electrophilic Substitution of Aminopyridines: Ortho Lithiation of 2-, 3-, and 4-(Pivaloylamino) pyridines", J. Org. Chem. 48, pp. 3401-3408 (1983).

Keenan, et al., "Conformational Preferences in Benzodiazephine Series of Potent Nonpeptide Fibrinogen Receptor Antagonists", J. Med. Chem. 42, pp. 545-559 (1999).

Hirokawa, et al., "Synthesis of N-(1-Ethyl-4-Methylhexahydro-1,4-Diazepin-6-YL)Nicotinamides and Their Affinities for 5-HT$_3$ and Dopamine D$_2$ Receptors", Biorganic & Medicinal Chemistry Letters, 8, pp. 1551-1554 (1998).

\* cited by examiner

OXO OR OXY-PYRIDINE COMPOUNDS AS 5-HT4 RECEPTOR MODULATORS

CROSS-REFERENCE TO RELATED APPLICATION

This application claims priority from U.S. provisional application No. 60/346,747, filed on Jan. 7, 2002.

TECHNICAL FIELD

This invention relates to novel oxo or oxy-pyridine compounds. These compounds have 5-HT$_4$ receptor binding activity (e.g., agonist or antagonist activities), and thus are useful for the treatment of or prevention of gastroesophageal reflux disease, gastrointestinal disease, gastric motility disorder, non-ulcer dyspepsia, irritable bowel syndrome, constipation, dyspepsia, esophagitis, gastroesophageral disease, nausea, central nervous system disease, alzheimers disease, cognitive disorder, emesis, migraine, neurological disease, pain, ischaemic stroke, anxiety, cardiovascular disorder or the like, in mammalian, especially human. The present invention also relates to a pharmaceutical composition comprising the above compounds.

BACKGROUND ART

Serotonin (5-HT) receptors are known to have a plurality of subtypes such as 5-HT$_1$, 5-HT$_2$, 5-HT$_3$ and 5-HT$_4$. These 5-HT$_4$ receptors are disclosed in, for example, European Journal of Pharmacology 146 (1988), 187–188, and Naunyn-Schmiedeberg's Arch. Pharmacol. (1989) 340:403–410.

5-HT$_4$ receptor modulators (e.g., agonists and antagonists) are found to be useful for the treatment of a variety of diseases such as gastroesophageal reflux disease, gastrointestinal disease, gastric motility disorder, non-ulcer dyspepsia, irritable bowel syndrome, constipation, dyspepsia, esophagitis, gastroesophageral disease, nausea, central nervous system disease, alzheimers disease, cognitive disorder, emesis, migraine, neurological disease, pain, and cardiovascular disorders such as cardiac failure and heart arryhthmia (See TiPs, 1992, 13, 141; Ford A. P. D. W. et al., Med. Res. Rev., 1993, 13, 633; Gullikson G. W. et al., Drug Dev. Res., 1992, 26, 405; Richard M. Eglen et al, TiPS, 1995, 16, 391; Bockaert J. Et al., CNS Drugs, 1, 6; Romanelli M. N. et al., Arzheim Forsch./Drug Res., 1993, 43, 913; Kaumann A. et al., Naunyn-Schmiedeberg's. 1991, 344, 150; and Romanelli M. N. et al., Arzheim Forsch./Drug Res., 1993, 43, 913).

A variety of oxy-pyridine compounds have been known as 5HT receptor antagonists or agonists. WO 94/07859 discloses oxy-pyridine compounds as 5HT$_4$ antagonists. WO93/08185; Japanese Patent Publication Laid-Open No. H09-067,347 and H10-203,987; describe a variety of oxy-pyridine compounds as 5HT$_3$ receptor antagonists.

Also, oxy-pyridine compounds synthesized for different uses are described in WO96/31475; WO01/5763; WO 99/50247; WO 97/27852; WO91/00858 and EP 274867.

It would be desirable if there were provided 5HT$_4$ receptor modulators (e.g., agonists and antagonists) which have more 5HT$_4$ receptor modulating activities (e.g., angonist or antagonist activities).

BRIEF DESCRIPTION OF THE INVENTION

The present invention provides compounds of the following formula (I) and (II):

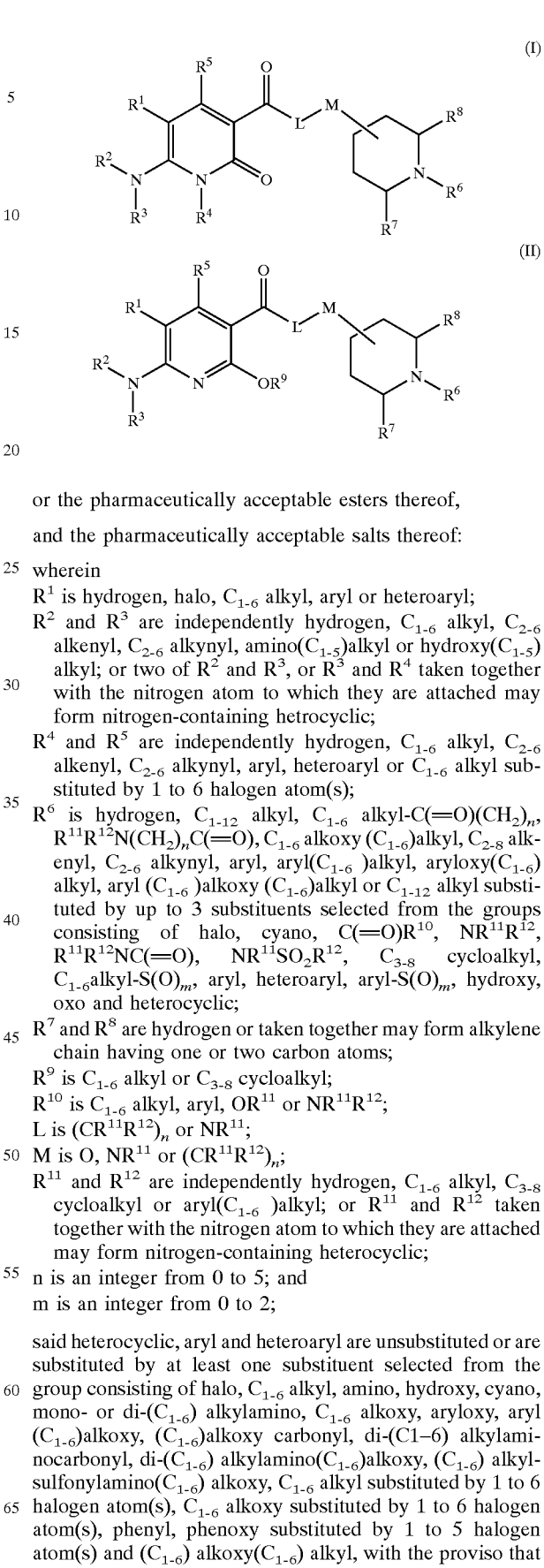

or the pharmaceutically acceptable esters thereof, and the pharmaceutically acceptable salts thereof:

wherein $R^1$ is hydrogen, halo, $C_{1-6}$ alkyl, aryl or heteroaryl;

$R^2$ and $R^3$ are independently hydrogen, $C_{1-6}$ alkyl, $C_{2-6}$ alkenyl, $C_{2-6}$ alkynyl, amino($C_{1-5}$)alkyl or hydroxy($C_{1-5}$) alkyl; or two of $R^2$ and $R^3$, or $R^3$ and $R^4$ taken together with the nitrogen atom to which they are attached may form nitrogen-containing hetrocyclic;

$R^4$ and $R^5$ are independently hydrogen, $C_{1-6}$ alkyl, $C_{2-6}$ alkenyl, $C_{2-6}$ alkynyl, aryl, heteroaryl or $C_{1-6}$ alkyl substituted by 1 to 6 halogen atom(s);

$R^6$ is hydrogen, $C_{1-12}$ alkyl, $C_{1-6}$ alkyl-C(=O)(CH$_2$)$_n$, $R^{11}R^{12}N(CH_2)_nC(=O)$, $C_{1-6}$ alkoxy ($C_{1-6}$)alkyl, $C_{2-8}$ alkenyl, $C_{2-6}$ alkynyl, aryl, aryl($C_{1-6}$)alkyl, aryloxy($C_{1-6}$)alkyl, aryl ($C_{1-6}$)alkoxy ($C_{1-6}$)alkyl or $C_{1-12}$ alkyl substituted by up to 3 substituents selected from the groups consisting of halo, cyano, C(=O)R$^{10}$, NR$^{11}$R$^{12}$, R$^{11}$R$^{12}$NC(=O), NR$^{11}$SO$_2$R$^{12}$, $C_{3-8}$ cycloalkyl, $C_{1-6}$alkyl-S(O)$_m$, aryl, heteroaryl, aryl-S(O)$_m$, hydroxy, oxo and heterocyclic;

$R^7$ and $R^8$ are hydrogen or taken together may form alkylene chain having one or two carbon atoms;

$R^9$ is $C_{1-6}$ alkyl or $C_{3-8}$ cycloalkyl;

$R^{10}$ is $C_{1-6}$ alkyl, aryl, OR$^{11}$ or NR$^{11}$R$^{12}$;

L is (CR$^{11}$R$^{12}$)$_n$ or NR$^{11}$;

M is O, NR$^{11}$ or (CR$^{11}$R$^{12}$)$_n$;

$R^{11}$ and $R^{12}$ are independently hydrogen, $C_{1-6}$ alkyl, $C_{3-8}$ cycloalkyl or aryl($C_{1-6}$)alkyl; or $R^{11}$ and $R^{12}$ taken together with the nitrogen atom to which they are attached may form nitrogen-containing heterocyclic;

n is an integer from 0 to 5; and m is an integer from 0 to 2;

said heterocyclic, aryl and heteroaryl are unsubstituted or are substituted by at least one substituent selected from the group consisting of halo, $C_{1-6}$ alkyl, amino, hydroxy, cyano, mono- or di-($C_{1-6}$) alkylamino, $C_{1-6}$ alkoxy, aryloxy, aryl ($C_{1-6}$)alkoxy, ($C_{1-6}$)alkoxy carbonyl, di-(C1–6) alkylaminocarbonyl, di-($C_{1-6}$) alkylamino($C_{1-6}$)alkoxy, ($C_{1-6}$) alkylsulfonylamino($C_{1-6}$) alkoxy, $C_{1-6}$ alkyl substituted by 1 to 6 halogen atom(s), $C_{1-6}$ alkoxy substituted by 1 to 6 halogen atom(s), phenyl, phenoxy substituted by 1 to 5 halogen atom(s) and ($C_{1-6}$) alkoxy($C_{1-6}$) alkyl, with the proviso that when $R^9$ is $C_{1-6}$ alkyl, then L is not $NR^{11}$; and when $R^9$ is $C_{1-6}$ alkyl and L is $(CR^{11}R^{12})_n$ wherein n is 0, then M is not $NR^{11}$.

The oxo or oxy-pyridine compounds of this invention have 5-$HT_4$ receptor modulating activities (e.g., an antagonistic or agonistic function towards 5-$HT_4$ receptor), and are thus useful for the treatment or prevention of disease conditions mediated by 5-$HT_4$ receptor activities.

Thus, the present invention provides a pharmaceutical composition for the treatment of disease conditions mediated by 5-$HT_4$ receptor activities, in a mammalian subject, which comprises administering to said subject a therapeutically effective amount of a compound of formula (I) and (II).

Further, the present invention also provides a pharmaceutical composition for the treatment of gastroesophageal reflux disease, gastrointestinal disease, gastric motility disorder, upper gut motility disorder, non-ulcer dyspepsia, irritable bowel syndrome, constipation, dyspepsia, esophagitis, gastroesophageral disease, nausea, central nervous system disease, alzheimers disease, cognitive disorder, emesis, migraine, neurological disease, pain, ischaemic stroke, anxiety, cardiovascular disorders such as cardiac failure and heart arryhthmia, or the like, which comprises a therapeutically effective amount of the oxo or oxy-pyridine compound of formula (I) and (II) or its pharmaceutically acceptable salt together with a pharmaceutically acceptable carrier.

Also, the present invention provides a method for the treatment of disease conditions mediated by 5-$HT_4$ receptor activities, in a mammalian subject, which comprises administering to said subject a therapeutically effective amount of a compound of formula (I) and (II). Further, the present invention provides a method for the treatment of the disease conditions as mentioned above. Furthermore, the present invention provides use of the compound of formula (I) and (II) in the manufacture of a medicament for the treatment or prevention of disease conditions mediated by 5-$HT_4$ receptor activity, in a mammalian subject. The conditions mediated by 5-$HT_4$ receptor activity are those diseases or disorders described as above.

DETAILED DESCRIPTION OF THE INVENTION

As used herein, the term "halo" means fluoro, chloro, bromo and iodo, preferably fluoro or chloro.

As used herein, the term "alkyl" means straight or branched chain saturated radicals, including, but not limited to methyl, ethyl, n-propyl, isopropyl, n-butyl, iso-butyl, secondary-butyl, tertiary-butyl, iso-pentyl, n-hexyl, n-heptyl, methylpentyl, butylmethyl and the like.

As used herein, the term "alkenyl" means straight or branched chain hydrocarbon radicals having at least one double bond including, but not limited to, ethenyl, propenyl, 1-butenyl, 2-butenyl, hexenyl, 4-methyl-3-pentenyl and the like.

As used herein, the term "alkynyl" means a hydrocarbon radical having at least one triple bond including, but not limited to, ethynyl, propynyl, 1-butynyl, 2-butynyl and the like.

As used herein, the term "alkylene" means saturated hydrocarbon (straight chain or branched) wherein a hydrogen atom is removed from each of the terminal carbons such as methylene, ethylene, propylene, butylene, pentylene, hexylene and the like.

As used herein, the term "cycloalkyl" means a saturated carbocyclic radical including, but not limited to, cyclopropyl, cyclobutyl, cyclohexyl, cycloheptyl, cyclooctyl, cyclononyl, cyclodecyl and the like.

As used herein, the term "alkoxy" means alkyl-O—, including, but not limited to methoxy, ethoxy, n-propoxy, isopropoxy, n-butoxy, iso-butoxy, secondary-butoxy, tertiary-butoxy.

As used herein, the term "acyl" means a group having carbonyl such as R'—C(O)— wherein R' is $C_{1-5}$ alkyl, phenyl or $C_{3-7}$ cycloalkyl, including, but not limited to formyl, acetyl, ethyl-C(O)—, n-propyl-C(O)—, isopropyl-C(O)—, n-butyl-C(O)—, iso-butyl-C(O)—, secondary-butyl-C(O)—, tertiary-butyl-C(O)—, cyclopropyl-C(O)—, cyclobutyl-C(O)—, cyclopentyl-C(O)—, cyclohexyl-C(O)—, cycloheptyl-C(O)—, and the like.

As used herein, the term "nitrogen-containing heterocyclic" means 5- to 10-membered monocyclic or bicyclic rings having at least one nitrogen ring atom, including, but not limited to, a heterocyclic ring selected from morpholino, piperazino, piperidino, pyrrolidino, azetidino, pyrazolidino, (1,2,3,4)-tetrahydroisoqunolino and perhydroisoquinolino, preferably morpholino, piperazino and piperidino.

As used herein, the term "aryl" means a monocyclic or bicyclic aromatic carbocyclic ring of 6 to 11 carbon atoms including, but not limited to, phenyl, naphthyl, indanyl, (1,2,3,4)-tetrahydronaphthyl, indenyl and isoindenyl, preferably phenyl and naphthyl.

As used herein, the term "aryloxy" means an O-aryl group wherein "aryl" is defined above.

As used herein, the term "arylalkyl" means an alkyl radical which is substituted by an aryl group as defined above.

As used herein, the term "heterocyclic" means a 5- to 11-membered monocyclic or bicyclic ring which may be saturated, partially unsaturated, or aromatic, and which consists of carbon atoms and from 1 to 4 heteroatoms independently selected from the group consisting of N, O and S. Examples of the heterocyclics include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H, 6H-1,5,2-dithiazinyl, thiophenyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4a H-carbazole, carbazole, beta-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl, 2-oxo-2,3,4,5-tetrahydro-1H-1-benzazepin-3-yl or oxazolidinyl. Preferable heterocyclic groups include piperidino, morpholino, thiamorpholino, pyrrolidino, pyrazolino, pyrazolidino, pyrazoryl, piperazinyl, furyl, thienyl, oxazolyl, tetrazolyl, thiazolyl, imidazolyl, imidazolinyl, pyrazolyl, pyridyl, pyrimidinyl, pyrrolyl, pyrrolidinyl, tetrahydropyaranyl and quinolyl.

As used herein, the term "heteroaryl" means a 5- to 12-membered monocyclic or bicyclic ring which consists of carbon atoms and from 1 to 4 heteroatoms independently selected from the group consisting of N, O and S. Examples of the heteroaryl include, but are not limited to, pyrazolyl, furyl, thienyl, oxazolyl, tetrazolyl, thiazolyl, imidazolyl, thiadiazolyl, pyridyl, pyrimidinyl, pyrrolyl, thiophenyl, pyrazinyl, pyridazinyl, isooxazolyl, isothiazolyl, triazolyl, benzofuranyl, isobenzofuranyl, benzothiophenyl, indolyl, isoindolyl, benzoxazolyl, benzothiazolyl, indazolyl, benzimidazolyl, quinolyl, isoquinolyl, cinnolinyl, phthalazinyl, quinazolinyl quinoxalinyl and the like.

As used herein, the term "substituted nitrogen-containing heterocyclic, substituted aryl, substituted arylalkyl, substituted heteroaryl or substituted heterocyclic" means those groups which are substituted with one to three (preferably one to two) substituents selected from halo, alkyl, amino, hydroxy, cyano, mono- or di-alkylamino, alkoxy, aryloxy, aralkyloxy, alkoxycarbonylalkoxy, dialkylaminocarbonylalkoxy, dialkylaminoalkoxy, alkylsulfonylaminoalkoxy and alkoxyalkyl.

As used herein, the term "modulator" means compounds, agonists, antagonists, ligands, substrates and enzymes, which directly or indirectly affect regulation of the receptor activity.

In the compounds of formula (I) and (II), $R^1$ is preferably hydrogen, halo, $C_{1-6}$ alkyl or heteroaryl; more preferably hydrogen, halo or heteroaryl; most preferably hydrogen or halo.

In the compounds of formula (I) and (II), $R^2$ and $R^3$ are preferably independently hydrogen or $C_{1-6}$ alkyl; or two of $R^2$ and $R^3$, or $R^3$ and $R^4$ taken together with the nitrogen atom to which they are attached may form nitrogen-containing hetrocyclic; more preferably independently hydrogen or $C_{1-6}$ alkyl; most preferably hydrogen.

In the compounds of formula (I) and (II), $R^4$ and $R^5$ are preferably independently hydrogen, $C_{1-6}$ alkyl, aryl, $C_{1-6}$ alkyl substituted with 1 to 6 halogen atom(s); said aryl is unsubstituted or is substituted by at least one substituent selected from the groups consisting of halo, $C_{1-6}$ alkyl, amino, hydroxy, cyano, mono- or di-($C_{1-6}$) alkylamino, $C_{1-6}$ alkoxy, aryloxy, aryl ($C_{1-6}$)alkoxy, ($C_{1-6}$)alkoxy carbonyl ($C_{1-6}$)alkoxy, di-(C1–6) alkylaminocarbonyl, di-($C_{1-6}$) alkylamino($C_{1-6}$) alkoxy, ($C_{1-6}$) alkylsulfonylamino($C_{1-6}$) alkoxy and ($C_{1-6}$) alkoxy($C_{1-6}$) alkyl; more preferably independently hydrogen, $C_{1-6}$ alkyl or $C_{1-6}$ alkyl substituted by 1 to 6 halogen atom(s); more preferably independently hydrogen or $C_{1-6}$ alkyl; and most preferably hydrogen.

In the compounds of formula (I) and (II), $R^6$ is $C_{1-12}$ alkyl, $C_{3-8}$ alkenyl or $C_{1-12}$ alkyl substituted by up to 3 substituents selected from the groups consisting of C(=O)$R^{10}$, $C_{3-8}$ cycloalkyl, hydroxy, cyano, oxo, phenyl, naphthyl, phenyl-S and 5–12 membered monocyclic or bicyclic aromatic or non-aromatic ring containing 1 to 4 heteroatoms selected from O, N and S;

said phenyl, naphthyl and 5–12 membered monocyclic or bicyclic aromatic or non-aromatic ring are unsubstituted or are substituted by at least one substituent selected from the groups consisting of halo, cyano, $C_{1-6}$ alkyl, $C_{1-6}$ alkyl substituted by 1 to 6 halogen atom(s), $C_{1-6}$ alkoxy, $C_{1-6}$ alkoxy substituted by 1 to 6 halogen atom(s), mono- or di-($C_{1-6}$)alkyl amino and $C_{1-6}$ alkoxy($C_{1-6}$) alkyl wherein $R^{10}$ is $C_{1-6}$alkyl, O$R^{11}$ or N$R^{11}R^{12}$ wherein $R^{11}$ and $R^{12}$ are independently hydrogen, $C_{3-8}$ cycloalkyl or $C_{1-6}$ alkyl; more preferably $C_{1-10}$ alkyl, $C_{3-8}$ alkenyl or $C_{1-10}$ alkyl substituted with up to 3 substituents selected from the groups consisting of C(=O)$R^{10}$, $C_{5-7}$ cycloalkyl, hydroxy, cyano, oxo, phenyl, naphthyl, phenyl-S, N$R^{11}R^{12}$ and heteroaryl selected from the groups consisting of indolyl, pyrazolyl, furyl, thienyl, oxazolyl, tetrazolyl, thiazolyl, imidazolyl, pyridyl, pyrimidinyl, pyrrolyl and quinolyl, and heterocyclic selected from the groups consisting of pyrazolino, pyrazolidino, imidazolinyl, piperidino, morpholino, thiamorpholino, pyrrolidino, piperazinyl, pyrrolidinyl, tetrahydrofuranyl, tetrahydropyranyl and phthalimidolyl; said phenyl, naphthyl, heteroaryl and heterocyclic are unsubstituted or are substituted by at least one substituent selected from the groups consisting of halo, cyano, $C_{1-6}$ alkyl, $C_{1-6}$ alkyl substituted by 1 to 6 halogen atom(s), $C_{1-6}$ alkoxy, $C_{1-6}$ alkoxy substituted by 1 to 6 halogen atom(s), mono- or di-($C_{1-6}$)alkyl amino and $C_{1-6}$ alkoxy($C_{1-6}$) alkyl wherein $R^{10}$ is $C_{1-6}$alkyl or $C_{1-6}$ alkoxy; $R^{11}$ and $R^{12}$ are independently hydrogen, $C_{3-8}$ cycloalkyl or $C_{1-6}$ alkyl; more preferably $C_{1-10}$ alkyl, $C_{3-8}$ alkenyl or $C_{1-10}$ alkyl substituted with up to 3 substituents selected from the groups consisting of C(=O)$R^{10}$, $C_{5-7}$ cycloalkyl, oxo, phenyl, naphthyl, phenyl-S, N$R^{11}R^{12}$ and heteroaryl selected from the groups consisting of indolyl, furyl, thienyl, oxazolyl, pyridyl, pyrrolyl and quinolyl, and heterocyclic selected from the groups consisting of piperidino, morpholino, pyrrolidino, piperazinyl, phthalimidolyl, tetrahydropyranyl and pyrrolidinyl; said phenyl, naphthyl, heteroaryl and heterocyclic are unsubstituted or are substituted by at least one substituent selected from the groups consisting of halo, $C_{1-6}$ alkyl, $C_{1-6}$ alkyl substituted by 1 to 6 halogen atom(s), $C_{1-6}$ alkoxy and $C_{1-6}$ alkoxy substituted by 1 to 6 halogen atom(s); more preferably isobutyl, cyclohexylmethyl, n-butyl, indolylethyl, phenylethyl, fluorophenylethyl, ethoxycarbonyl(n-propyl)methyl, methoxycarbonyl(phenyl)methyl, naphthylethyl, trifuluoromethoxyphenylmethyl, n-heptyl, n-butyl(ethoxycarbonyl) methyl, (1,3-dioxo-1,3-dihydro-2H-isoindol-2-yl)propyl, isopentyl, n-hexyl, hexenyl, chlorophenylmethyl, dichlorophenylmethyl, pyrrolylethyl, ethoxycarbonyl(ethyl)methyl, cyclohexylethyl, ethoxycarbonyl(isopropyl)methyl, ethylhexyl, phenylthioethyl, methylpentyl, (1,3-dioxo-1,3-dihydro-2H-isoindol-2-yl)butyl, bromofluorophenylmethyl, butylmethyl or bromophenylmethyl; dimethoxyphenyl-oxoethyl, benzoylethyl, 3,3-dimethyl-2-oxobutyl, 1,3,3-trimethyl-2-oxobutyl-2-oxobutyl, 2-hydroxy-3,3-dimethylbutyl, 4-methoxycarbonyl-3,3-dimethyl-2-oxo-butyl, 3,3-dimethyl-2-oxobutyl, neopentyl, [(dimethylamino)carbonyl]pentyl, (piperidinylcarbonyl)pentyl or {[cyclohexyl(methyl) amino]carbonyl}pentyl; most preferably isobutyl, cyclohexylmethyl, n-butyl, indolylethyl, phenylethyl, fluorophenylethyl, ethoxycarbonyl(n-propyl)methyl, methoxycarbonyl(phenyl)methyl, naphthylethyl; 4-methoxycarbonyl-3,3-dimethyl-2-oxo-butyl, 3,3-dimethyl-2-oxobutyl, neopentyl, [(dimethylamino)carbonyl]pentyl, (piperidinylcarbonyl)pentyl or {[cyclohexyl(methyl)amino]carbonyl}pentyl.

In the compounds of formula (I) and (II), $R^7$ and $R^8$ are preferably hydrogen.

In the compounds of formula (I) and (II), $R^9$ is preferably $C_{1-6}$ alkyl.

In the compounds of formula (I) and (II), L is preferably $(CR^{11}R^{12})_n$ or $NR^{11}$, wherein $R^{11}$ and $R^{12}$ are independently hydrogen or $C_{1-6}$ alkyl, and n is an integer from 0 to 3; more preferably $(CR^{11}R^{12})_n$ or $NR^{11}$, wherein $R^{11}$ and $R^{12}$ are independently hydrogen or methyl, and n is an integer from 0 to 2; most preferably $NR^{11}$.

In the compounds of formula (I) and (II), M is preferably $(CR^{11}R^{12})_n$ or $NR^{11}$, wherein $R^{11}$ and $R^{12}$ are independently hydrogen or $C_{1-6}$ alkyl, and n is an integer from 0 to 3; more preferably $(CR^{11}R^{12})_n$, wherein $R^{11}$ and $R^{12}$ are independently hydrogen or methyl, and n is an integer from 0 to 2; most preferably chemical bond or methylene.

Preferred compounds of this invention are those of the formula (I) wherein $R^1$ is hydrogen, halo, $C_{1-6}$ alkyl or heteroaryl;

$R^2$ and $R^3$ are independently hydrogen or $C_{1-6}$ alkyl; or two of $R^2$ and $R^3$, or $R^3$ and $R^4$ taken together with the nitrogen atoms to which they are attached may form nitrogen-containing hetrocyclic;

$R^4$ and $R^5$ are independently hydrogen, $C_{1-6}$ alkyl, aryl, $C_{1-6}$ alkyl substituted with 1 to 6 halogen atom(s);

said aryl is unsubstituted or is substituted by at least one substituent selected from the groups consisting of halo, $C_{1-6}$ alkyl, amino, hydroxy, cyano, mono- or di-$(C_{1-6})$ alkylamino, $C_{1-6}$ alkoxy, aryloxy, aryl $(C_{1-6})$alkoxy, $(C_{1-6})$ alkoxy carbonyl$(C_{1-6})$alkoxy, di-(C1–6) alkylaminocarbonyl, di-$(C_{1-6})$ alkylamino$(C_{1-6})$ alkoxy, $(C_{1-6})$ alkylsulfonylamino$(C_{1-6})$ alkoxy and $(C_{1-6})$ alkoxy$(C_{1-6})$ alkyl;

$R^6$ is $C_{1-12}$ alkyl, $C_{3-8}$ alkenyl or $C_{1-12}$ alkyl substituted by up to 3 substituents selected from the groups consisting of $C(=O)R^{10}$, $C_{3-8}$ cycloalkyl, hydroxy, cyano, oxo, phenyl, naphthyl, phenyl-S and 5–12 membered monocyclic or bicyclic aromatic or non-aromatic ring containing 1 to 4 heteroatoms selected from O, N and S;

said phenyl, naphthyl and 5–12 membered monocyclic or bicyclic aromatic or non-aromatic ring are unsubstituted or are substituted by at least one substituent selected from the groups consisting of halo, cyano, $C_{1-6}$ alkyl, $C_{1-6}$ alkyl substituted by 1 to 6 halogen atom(s), $C_{1-6}$ alkoxy, $C_{1-6}$ alkoxy substituted by 1 to 6 halogen atom(s), mono- or di-$(C_{1-6})$alkyl amino and $C_{1-6}$ alkoxy$(C_{1-6})$ alkyl; and $R^7$ and $R^8$ are hydrogen;

$R^9$ is $C_{1-6}$ alkyl;

$R^{10}$ is $C_{1-6}$alkyl, $OR^{11}$ or $NR^{11}R^{12}$ wherein $R^{11}$ and $R^{12}$ are independently hydrogen, $C_{3-8}$ cycloalkyl or $C_{1-6}$ alkyl;

L is $(CR^{11}R^{12})_n$ or $NR^{11}$, wherein $R^{11}$ and $R^{12}$ are independently hydrogen or $C_{1-6}$ alkyl, and n is an integer from 0 to 3; and M is $(CR^{11}R^{12})_n$ or $NR^{11}$, wherein $R^{11}$ and $R^{12}$ are independently hydrogen or $C_{1-6}$ alkyl, and n is an integer from 0 to 3;

said heterocyclic, aryl and heteroaryl are unsubstituted or are substituted by at least one substituent selected from the group consisting of halo, $C_{1-6}$ alkyl, amino, hydroxy, cyano, mono- or di-$(C_{1-6})$ alkylamino, $C_{1-6}$ alkoxy, aryloxy, aryl $(C_{1-6})$alkoxy, $(C_{1-6})$alkoxy carbonyl$(C_{1-6})$alkoxy, di-(C1–6) alkylaminocarbonyl, di-$(C_{1-6})$ alkylamino$(C_{1-6})$ alkoxy, $(C_{1-6})$ alkylsulfonylamino$(C_{1-6})$ alkoxy and $(C_{1-6})$ alkoxy $(C_{1-6})$ alkyl.

More preferred compounds of this invention are those of the formula (I) wherein $R^1$ is hydrogen, halo or heteroaryl;

$R^2$ and $R^3$ are independently hydrogen or $C_{1-6}$ alkyl;

$R^4$ and $R^5$ are independently hydrogen, $C_{1-6}$ alkyl or $C_{1-6}$ alkyl substituted by 1 to 6 halogen atom(s);

$R^6$ is $C_{1-10}$ alkyl, $C_{3-8}$ alkenyl or $C_{1-10}$ alkyl substituted with up to 3 substituents selected from the groups consisting of $C(=O)R^{10}$, $C_{5-7}$ cycloalkyl, hydroxy, cyano, oxo, phenyl, naphthyl, phenyl-S, $NR^{11}R^{12}$ and heteroaryl selected from the groups consisting of indolyl, pyrazolyl, furyl, thienyl, oxazolyl, tetrazolyl, thiazolyl, imidazolyl, pyridyl, pyrimidinyl, pyrrolyl and quinolyl, and heterocyclic selected from the groups consisting of pyrazolino, pyrazolidino, imidazolinyl, piperidino, morpholino, thiamorpholino, pyrrolidino, piperazinyl, pyrrolidinyl, tetrahydrofuranyl, tetrahydropyranyl and phthalimidolyl;

said phenyl, naphthyl, heteroaryl and heterocyclic are unsubstituted or are substituted by at least one substituent selected from the groups consisting of halo, cyano, $C_{1-6}$ alkyl, $C_{1-6}$ alkyl substituted by 1 to 6 halogen atom(s), $C_{1-6}$ alkoxy, $C_{1-6}$ alkoxy substituted by 1 to 6 halogen atom(s), mono- or di-$(C_{1-6})$alkyl amino and $C_{1-6}$ alkoxy $(C_{1-6})$ alkyl;

$R^{10}$ is $C_{1-6}$alkyl or $C_{1-6}$ alkoxy;

$R^{11}$ and $R^{12}$ are independently hydrogen, $C_{3-8}$ cycloalkyl or $C_{1-6}$ alkyl;

L is $(CR^{11}R^{12})$, or $NR^{11}$, wherein $R^{11}$ and $R^{12}$ are independently hydrogen or methyl, and n is an integer from 0 to 2; and M is $(CR^{11}R^{12})_n$, wherein $R^{11}$ and $R^{12}$ are independently hydrogen or methyl, and n is an integer from 0 to 2.

Also, preferred compounds of this invention are those of the formula (I)

wherein $R^1$ is hydrogen or halo;

$R^2$ and $R^3$ are hydrogen;

$R^4$ and $R^5$ are independently hydrogen or $C_{1-6}$ alkyl;

$R^6$ is $C_{1-10}$ alkyl, $C_{3-8}$ alkenyl or $C_{1-10}$ alkyl substituted with up to 3 substituents selected from the groups consisting of $C(=O)R^{10}$, $C_{5-7}$ cycloalkyl, oxo, phenyl, naphthyl, phenyl-S, $NR^{11}R^{12}$ and heteroaryl selected from the groups consisting of indolyl, furyl, thienyl, oxazolyl, pyridyl, pyrrolyl and quinolyl, and heterocyclic selected from the groups consisting of piperidino, morpholino, pyrrolidino, piperazinyl, phthalimidolyl, pyrrolidinyl and tetrahydropyaranyl;

said phenyl, naphthyl, heteroaryl and heterocyclic are unsubstituted or are substituted by at least one substituent selected from the groups consisting of halo, cyano, $C_{1-6}$ alkyl, $C_{1-6}$ alkyl substituted by 1 to 6 halogen atom(s), $C_{1-6}$ alkoxy, $C_{1-6}$ alkoxy substituted by 1 to 6 halogen atom(s), mono- or di-$(C_{1-6})$alkyl amino and $C_{1-6}$ alkoxy $(C_{1-6})$ alkyl;

$R^{10}$ is $C_{1-6}$alkoxy;

$R^{11}$ and $R^{12}$ are independently $C_{3-8}$ cycloalkyl or $C_{1-6}$ alkyl;

L is $(CR^{11}R^{12})_n$ or $NR^{11}$, wherein $R^{11}$ and $R^{12}$ are independently hydrogen or methyl, and n is an integer from 0 to 2; and M is $(CR^{11}R^{12})_n$, wherein $R^{11}$ and $R^{12}$ are independently hydrogen or methyl, and n is an integer from 0 to 2

Also, more preferred compounds of this invention are those of the formula (I) wherein $R^1$ is hydrogen or halo;

$R^2$ and $R^3$ are hydrogen;

$R^4$ and $R^5$ are hydrogen;

$R^6$ is $C_{1-10}$ alkyl, $C_{3-8}$ alkenyl or $C_{1-10}$ alkyl substituted with up to 3 substituents selected from the groups consisting of $C_{1-6}$ alkoxycarbonyl, $C_{5-7}$ cycloalkyl, oxo, phenyl, naphthyl, phenyl-S and heteroaryl selected from the groups consisting of indolyl and pyridyl, and heterocyclic selected from the groups consisting of pyrrolyl, piperidino, phthalimidolyl and tetrahydropyranyl;

said phenyl, naphthyl, heteroaryl and heterocyclic are unsubstituted or are substituted by at least one substituent selected from the groups consisting of halo, $C_{1-6}$ alkyl, $C_{1-6}$ alkyl substituted by 1 to 6 halogen atom(s), $C_{1-6}$ alkoxy and $C_{1-6}$ alkoxy substituted by 1 to 6 halogen atom(s);

$R^{10}$ is $C_{1-6}$ alkoxy;

L is $(CR^{11}R^{12})_n$ or $NR^{11}$, wherein $R^{11}$ and $R^{12}$ are independently hydrogen or methyl, and n is an integer from 0 to 2; and M is $(CR^{11}R^{12})_n$, wherein $R^{11}$ and $R^{12}$ are independently hydrogen or methyl, and n is an integer from 0 to 2

Also, more preferred compounds of this invention are those of the formula (I) wherein $R^1$ is hydrogen or halo;

$R^2$ and $R^3$ are hydrogen;

$R^4$ and $R^5$ are hydrogen;

$R^6$ is isobutyl, cyclohexylmethyl, n-butyl, indolylethyl, phenylethyl, fluorophenylethyl, ethoxycarbonyl(n-propyl)methyl, methoxycarbonyl(phenyl)methyl, naphthylethyl, trifuluoromethoxyphenylmethyl, n-heptyl, n-butyl (ethoxycarbonyl)methyl, (1,3-dioxo-1,3-dihydro-2H-isoindol-2-yl)propyl, isopentyl, n-hexyl, hexenyl, chlorophenylmethyl, dichlorophenylmethyl, pyrrolylethyl, ethoxycarbonyl(ethyl)methyl, cyclohexylethyl, ethoxycarbonyl(isopropyl)methyl, ethylhexyl, phenylthioethyl, methylpentyl, (1,3-dioxo-1,3-dihydro-2H-isoindol-2-yl) butyl, bromofluorophenylmethyl, butylmethyl, bromophenylmethyl, dimethoxyphenyl-oxoethyl, benzoylethyl, 3,3-dimethyl-2-oxobutyl, 1,3,3-trimethyl-2-oxobutyl-2-oxobutyl, 2-hydroxy-3,3-dimethylbutyl, 4-methoxycarbonyl-3,3-dimethyl-2-oxo-butyl, 3,3-dimethyl-2-oxobutyl, neopentyl, [(dimethylamino)carbonyl]pentyl, (piperidinylcarbonyl)pentyl or {[cyclohexyl(methyl)amino]carbonyl}pentyl;

$R^{10}$ is $C_{1-6}$ alkoxy;

L is $(CR^{11}R^{12})_n$ or $NR^{11}$, wherein $R^{11}$ and $R^{12}$ are independently hydrogen or methyl, and n is an integer from 0 to 2; and M is chemical bond or methylene.

Also, more preferred compounds of this invention are those of the formula (1) wherein $R^1$ is hydrogen or halo;

$R^2$ and $R^3$ are hydrogen;

$R^4$ and $R^5$ are hydrogen;

$R^6$ is isobutyl, cyclohexylmethyl, n-butyl, indolylethyl, phenylethyl, fluorophenylethyl, ethoxycarbonyl(n-propyl)methyl, methoxycarbonyl(phenyl)methyl, naphthylethyl, 4-methoxycarbonyl-3,3-dimethyl-2-oxo-butyl, 3,3-dimethyl-2-oxobutyl, neopentyl, [(dimethylamino)carbonyl]pentyl, (piperidinylcarbonyl)pentyl or {[cyclohexyl(methyl)amino]carbonyl}pentyl;

$R^{10}$ is $C_{1-6}$ alkoxy;

L is $NR^{11}$; and

M is chemical bond or methylene.

Preferred individual compounds of this invention are:

6-amino-5-chloro-2-oxo-N-({1-[4-(trifluoromethoxy)benzyl]-4-piperidinyl}methyl)-1,2-dihydro-3-pyridinecarboxamide;

6-amino-5-chloro-N-[(1-heptyl-4-piperidinyl)methyl]-2-oxo-1,2-dihydro-3-pyridinecarboxamide;

ethyl 2-[4-({[(6-amino-5-chloro-2-oxo-1,2-dihydro-3-pyridinyl)carbonyl] amino}methyl)-1-piperidinyl]hexanoate;

6-amino-5-chloro-N-({1-[3-(1,3-dioxo-1,3-dihydro-2H-isoindol-2-yl)propyl]-4-piperidinyl}methyl)-2-oxo-1,2-dihydro-3-pyridinecarboxamide;

6-amino-5-chloro-N-{[1-(3-methylbutyl)-4-piperidinyl]methyl}-2-oxo-1,2-dihydro-3-pyridinecarboxamide;

6-amino-5-chloro-N-[(1-hexyl-4-piperidinyl)methyl]-2-oxo-1,2-dihydro-3-pyridinecarboxamide;

6-amino-5-chloro-N-{[1-(5-hexenyl)-4-piperidinyl]methyl}-2-oxo-1,2-dihydro-3-pyridinecarboxamide;

6-amino-5-chloro-N-{[1-(3-chlorobenzyl)-4-piperidinyl]methyl}-2-oxo-1,2-dihydro-3-pyridinecarboxamide;

6-amino-5-chloro-N-{[1-(2,6-dichlorobenzyl)-4-piperidinyl]methyl}-2-oxo-1,2-dihydro-3-pyridinecarboxamide;

6-amino-5-chloro-2-oxo-N-({1-[2-(1H-pyrrol-1-yl)ethyl]-4-piperidinyl}methyl)-1,2-dihydro-3-pyridinecarboxamide;

ethyl 2-[4-({[(6-amino-5-chloro-2-oxo-1,2-dihydro-3-pyridinyl)carbonyl] amino}methyl)-1-piperidinyl]butanoate;

6-amino-5-chloro-N-{[1-(2-cyclohexylethyl)-4-piperidinyl]methyl}-2-oxo-1,2-dihydro-3-pyridinecarboxamide;

ethyl 2-[4-({[(6-amino-5-chloro-2-oxo-1,2-dihydro-3-pyridinyl)carbonyl] amino}methyl)-1-piperidinyl]-3-methylbutanoate;

6-amino-5-chloro-N-{[1-(2-ethylhexyl)-4-piperidinyl]methyl}-2-oxo-1,2-dihydro-3-pyridinecarboxamide;

6-amino-5-chloro-2-oxo-N-({1-[2-(phenylthio)ethyl]-4-piperidinyl}methyl)-1,2-dihydro-3-pyridinecarboxamide;

6-amino-5-chloro-N-{[1-(4-methylpentyl)-4-piperidinyl]methyl}-2-oxo-1,2-dihydro-3-pyridinecarboxamide;

6-amino-5-chloro-N-({1-[4-(1,3-dioxo-1,3-dihydro-2H-isoindol-2-yl)butyl]-4-piperidinyl}methyl)-2-oxo-1,2-dihydro-3-pyridinecarboxamide;

6-amino-N-{[1-(4-bromo-2-fluorobenzyl)-4-piperidinyl]methyl}-5-chloro-2-oxo-1,2-dihydro-3-pyridinecarboxamide;

6-amino-N-[(1-butyl-4-piperidinyl)methyl]-5-chloro-2-oxo-1,2-dihydro-3-pyridinecarboxamide di-hydrochloride;

6-amino-5-chloro-N-{[1-(2-methylbutyl)-4-piperidinyl]methyl}-2-oxo-1,2-dihydro-3-pyridinecarboxamide;

6-amino-N-{[1-(2-bromobenzyl)-4-piperidinyl]methyl}-5-chloro-2-oxo-1,2-dihydro-3-pyridinecarboxamide;

6-amino-N-{[1-(3-bromobenzyl)-4-piperidinyl]methyl}-5-chloro-2-oxo-1,2-dihydro-3-pyridinecarboxamide;

1-(6-amino-5-chloro-2-methoxy-3-pyridinyl)-3-(1-isobutyl-4-piperidinyl)-1-propanone;

6-amino-5-chloro-N-{[1-(cyclohexylmethyl)-4-piperidinyl]methyl}-2-oxo-1,2-dihydro-3-pyridinecarboxamide;

6-amino-5-chloro-N-({1-[2-(1H-indol-2-yl)ethyl]-4-piperidinyl}methyl)-2-oxo-1,2-dihydro-3-pyridinecarboxamide;

6-amino-5-chloro-2-oxo-N-{[1-(2-phenylethyl)-4-piperidinyl]methyl}-1,2-dihydro-3-pyridinecarboxamide;

6-amino-5-chloro-N-({1-[2-(4-fluorophenyl)ethyl]-4-piperidinyl}methyl)-2-oxo-1,2-dihydro- 3-pyridinecarboxamide;

6-amino-5-chloro-N-({1-[2-(1H-indol-3-yl)ethyl]-4-piperidinyl}methyl)-2-oxo-1,2-dihydro-3-pyridinecarboxamide;

ethyl 2-[4-({[(6-amino-5-chloro-2-oxo-1,2-dihydro-3-pyridinyl)carbonyl] amino}methyl)-1-piperidinyl]pentanoate;

methyl [4-({[(6-amino-5-chloro-2-oxo-1,2-dihydro-3-pyridinyl)carbonyl] amino}methyl)-1-piperidinyl](phenyl)acetate;

6-amino-5-chloro-N-{[1-(2-methylpropyl)-4-piperidinyl]methyl}-2-oxo-1,2-dihydro-3-pyridinecarboxamide;

6-amino-5-chloro-N-({1-[2-(1-naphthyl)ethyl]-4-piperidinyl}methyl)-2-oxo-1,2-dihydro-3-pyridinecarboxamide;
6-amino-5-chloro-N-({1-[2-(2,4-dimethoxyphenyl)-2-oxoethyl]piperidin-4-yl}methyl)-2-oxo-1,2-dihydropyridine-3-carboxamide;
6-Amino-5-chloro-N-{[1-(1-methyl-2-oxo-2-phenylethyl)piperidin-4-yl]methyl}-2-oxo-1,2-dihydropyridine-3-carboxamide;
6-amino-5-chloro-3-{3-[1-(3,3-dimethyl-2-oxobutyl)piperidine-4-yl] prpanoyl}pyridin-2(1H)-one;
6-amino-5-chloro-3-{3-[1-(1,3,3-trimethyl-2-oxobutyl-2-oxobutyl)piperidine-4-yl]propanoyl}pyridin-2(1H)-one;
6-amino-5-chloro-3-{3-[1-(cyclohexylmethyl)piperidine-4-yl]propanoyl}pyridin-2(1H)-one;
6-amino-5-chloro-3-{3-[1-(2-hydroxy-3,3-dimethylbutyl)piperidine-4-yl] propanoyl}pyridin-2(1H)-one;
methyl 5-[4-({[(6-amino-5-chloro-2-oxo-1,2-dihydropyridin-3-yl)carbonyl] amino}methyl)piperidin-1-yl]-3,3-dimethyl-4-oxopentanoate;
6-amino-5-chloro-N-{[1-(3,3-dimethyl-2-oxobutyl)piperidin-4-yl]methyl}-2-oxo-1,2-dihydropyridine-3-carboxamide;
6-amino-5-chloro-N-[(1-neopentylpiperidin-4-yl)methyl]-2-oxo-1,2-dihydropyridine-3-carboxamide;
6-amino-5-chloro-N-[(1-{1-[(methylamino)carbonyl]pentyl}piperidin-4-yl)methyl]-2-oxo-1,2-dihydropyridine-3-carboxamide;
6-amino-5-chloro-2-oxo-N-({1-[1-(piperidin-1-ylcarbonyl)pentyl]piperidin-4-yl} methyl)-1,2-dihydropyridine-3-carboxamide; and
6-amino-5-chloro-N-{[1-(1-{[cyclohexyl(methyl)amino]carbonyl}pentyl)piperidine-4-yl]methyl}-2-oxo-1,2-dihydropyridine-3-carboxamide; and salts thereof.
Most preferred individual compounds of this invention are:
1-(6-amino-5-chloro-2-methoxy-3-pyridinyl)-3-(1-isobutyl-4-piperidinyl)-1-propanone;
6-amino-5-chloro-N-{[1-(cyclohexylmethyl)-4-piperidinyl]methyl}-2-oxo-1,2-dihydro-3-pyridinecarboxamide;
6-amino-5-chloro-N-({1-[2-(1H-indol-2-yl)ethyl]-4-piperidinyl}methyl)-2-oxo-1,2-dihydro-3-pyridinecarboxamide;
6-amino-5-chloro-2-oxo-N-{[1-(2-phenylethyl)-4-piperidinyl]methyl}-1,2-dihydro-3-pyridinecarboxamide;
6-amino-5-chloro-N-({1-[2-(4-fluorophenyl)ethyl]-4-piperidinyl}methyl)-2-oxo-1,2-dihydro-3-pyridinecarboxamide;
6-amino-5-chloro-N-({1-[2-(1H-indol-3-yl)ethyl]-4-piperidinyl}methyl)-2-oxo-1,2-dihydro-3-pyridinecarboxamide;
ethyl 2-[4-({[(6-amino-5-chloro-2-oxo-1,2-dihydro-3-pyridinyl)carbonyl] amino}methyl)-1-piperidinyl]pentanoate;
methyl [4-({[(6-amino-5-chloro-2-oxo-1,2-dihydro-3-pyridinyl)carbonyl] amino}methyl)-1-piperidinyl](phenyl)acetate;
6-amino-5-chloro-N-{[1-(2-methylpropyl)-4-piperidinyl]methyl}-2-oxo-1,2-dihydro-3-pyridinecarboxamide;
6-amino-5-chloro-N-({1-[2-(1-naphthyl)ethyl]-4-piperidinyl}methyl)-2-oxo-1,2-dihydro-3-pyridinecarboxamide;
6-amino-5-chloro-2-oxo-N-({1-[4-(trifluoromethoxy)benzyl]-4-piperidinyl}methyl)-1,2-dihydro-3-pyridinecarboxamide;
methyl 5-[4-({[(6-amino-5-chloro-2-oxo-1,2-dihydropyridin-3-yl)carbonyl] amino}methyl)piperidin-1-yl]-3,3-dimethyl-4-oxopentanoate;
6-amino-5-chloro-N-{[1-(3,3-dimethyl-2-oxobutyl-2-oxobutyl)piperidin-4-yl] methyl}-2-oxo-1,2-dihydropyridine-3-carboxamide;
6-amino-5-chloro-N-[(1-neopentylpiperidin-4-yl)methyl]-2-oxo-1,2-dihydropyridine- 3-carboxamide;
6-amino-5-chloro-N-[(1-{1-[(methylamino)carbonyl]pentyl}piperidin-4-yl)methyl]-2-oxo-1,2-dihydropyridine-3-carboxamide;
6-amino-5-chloro-2-oxo-N-({1-[1-(piperidin-1-ylcarbonyl)pentyl]piperidin-4-yl}methyl)-1,2-dihydropyridine-3-carboxamide; and
6-amino-5-chloro-N-{[1-(1-{[cyclohexyl(methyl)amino]carbonyl}pentyl)piperidine-4-yl] methyl}-2-oxo-1,2-dihydropyridine-3-carboxamide; and salts thereof.

General Synthesis

The oxo or oxy-pyridine compounds of formula (I) and (II) of this invention may be prepared by a variety of synthetic methods. For example, the oxo-pyridine compounds of formula (Ia) wherein L is NH, may be prepared by a coupling reaction of the compound (1) with an amine compound (2) to obtain a corresponding amide compound (3), followed by a hydrolysis of the compound (3), as indicated in the following Scheme 1.

Scheme 1:

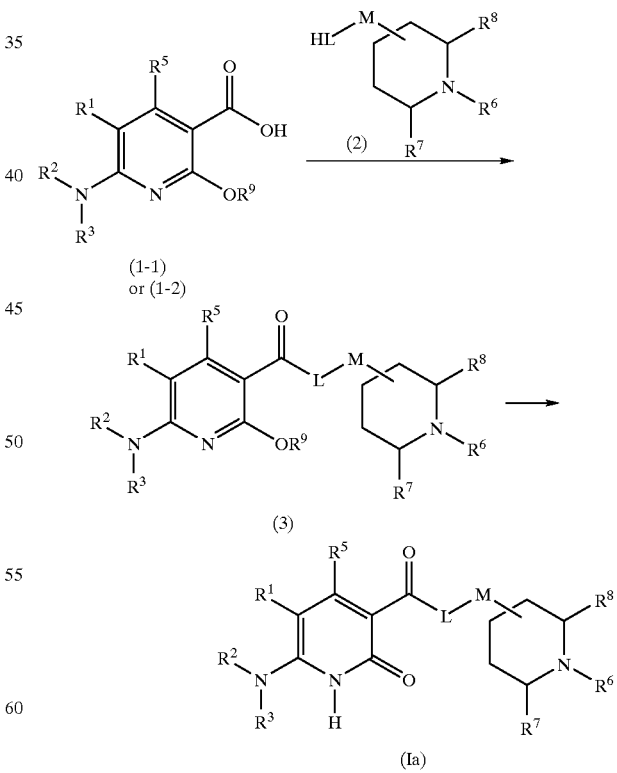

(wherein L is NH; $R^9$ is $C_{1-6}$ alkyl, $C_{3-8}$ cycloalkyl, tetrahydropyranyl, methoxymethyl, methoxyethoxymethyl, tert-butyldimethylsilyl (TBS), benzyl, substituted or non-substituted phenylmethyl, for example, methoxybenzyl; and all other symbols are as already defined).

In Scheme 1, the carboxylic acid compound (1) may be coupled with the amine compound (2) to give an oxypyridine compound (3) wherein L is NH.

The coupling reaction may be carried out in the presence of a suitable condensation agent in a reaction-inert solvent. Suitable condensation agents include 1,1'-carbonyldiimidazole (CDI), diisopropylcarbodiimide (DIC), dicyclohexylcarbodiimide (DCC), water soluble carbodiimide (WSC), 2-ethoxy-N-ethoxycarbonyl- 1,2-dihydroquinoline, benzotriazol-1-yloxy-tris(dimethylamino) phosphonium hexafluorophosphate (BOP), diethyl azodicarboxylate-triphenylphosphine, diethylcyanophosphonate (DEPC), diphenylphosphorylazide (DPPA), bromotripyrrolidino phosphonium hexafluorophosphate (PyBrop[trademark]), bis(2-oxo-3-oxazolidinyl) phosphinic chloride (BOPCl), benzotriazole-1-yl-oxy-tris-pyrrolidino-phosphonium hexafluorophosphate (PyBOP), 2-(1-H-benzotriazole-1-yl)-1,1,3,3,-tetramethyluronium hexafluorophosphate (HBTU) and ethyl chloroformate. Suitable reaction-inert solvents include aqueous or non-aqueous organic solvents such as tetrahydrofuran, N,N-dimethylformamide (DMF), dioxane, acetone, dimethoxyethane and acetonitrile; and halogenated hydrocarbons such as chloroform, dichloromethane and dichloroethane (preferably dichloromethane). This reaction may be carried out at a temperature in the range from −20 to 80° C., usually from 0° C. to 30° C. for 30 minutes to 100 hours, usually 5 hours to 30 hours.

The hydrolysis may be carried out by conventional procedures. In a typical procedure, the hydrolysis is carried out by treatment with diluted hydrochloric acid in a suitable reaction-inert solvent such as methanol at a temperature in the range from 50° C. to the reflux temperature, usually from 70° C. to the reflux temperature for 30 minute to 24 hour, usually 1 to 10 hours.

When $R^9$ is benzyl group, the compound (Ia) can be prepared by subjecting a compound (3) to catalytic hydrogenation followed by hydrolysis. The catalytic hydrogenation can be carried out in the presence of hydrogen or hydrogen source such as ammonium formate, and a suitable metal containing catalysts such as palladium, platinum, nickel, platinum oxide and rhodium in a suitable reaction-inert solvent such as methanol. The preferred catalyst is palladium on carbon. This hydrogenation can be carried out at a temperature in the range from 20 to 100° C., usually from 25° C. to 80° C. for 5 minutes to 48 hours, usually 30 minutes to 24 hours.

Scheme 2:

Alternatively, the compounds (Ia) may also be prepared in the following reaction steps.

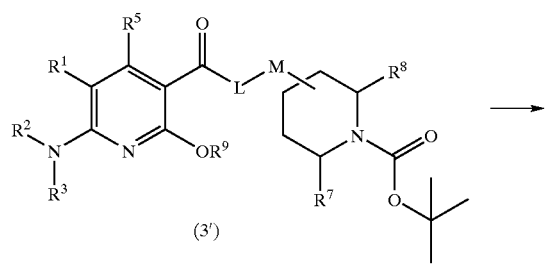

(3')

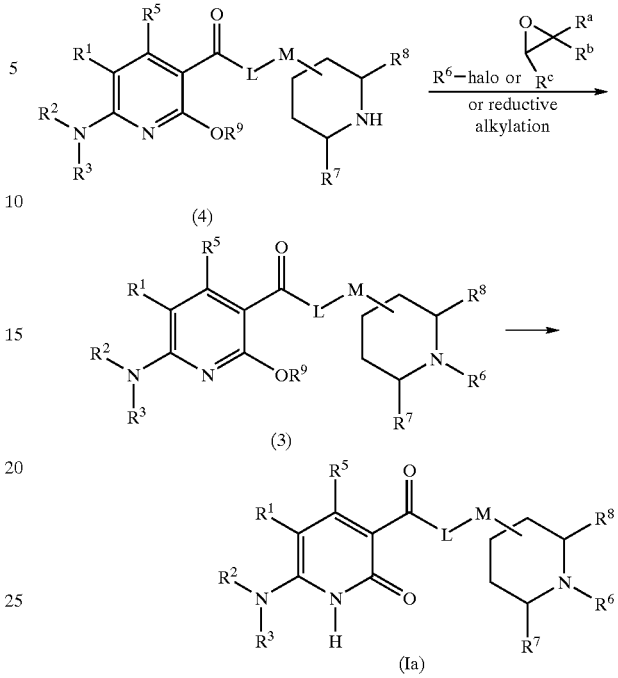

In Scheme 2, tert-butoxycarbonyl (Boc) compound of formula (3) wherein $R^6$ is Boc, (hereinafter represented by Formula (3')), may be subject to deprotection of an amino-protecting group, to obtain a compound (4). The deprotection may be carried out in the presence of acid (e.g., hydrochloric acid and sulfuric acid). The deprotection can be carried out in a suitable reaction-inert solvent such as methanol at a temperature in the range from 0 to 50° C., usually from 0 to 30° C. for 10 minutes to 24 hours, usually 30 minutes to 20 hours. The compound of formula (3) may be prepared from the compound of formula (4) by methods known to those skilled in the art. The compound of formula (4) may be treated with appropriate halide derivatives, $R^6$-halo in the presence of a base such as sodium bicarbonate, sodium carbonate, potassium carbonate, triethyl amine and diisopropyl ethyl amine in a reaction inert solvent such as THF and DMF at about 30 to 150° C., usually from 50° C. to 100° C. for 30 minutes to 24 hours, usually 30 minutes to 12 hours. Alternatively, the compound of formula (3) may be prepared from the compound of formula (4) by treating with an epoxide compound of formula (2-1) wherein $R^a$, $R^b$ and $R^c$ are $C_{1-6}$ alkyl. This reaction may be carried out in the presence of a base such as sodium bicarbonate, sodium carbonate, potassium carbonate, cesium carbonate, triethyl amine and diisopropyl ethyl amine in a reaction inert solvent such as THF and DMF at about 30 to 150° C., usually from 50° C. to 100° C. for 30 minutes to 24 hours, usually 30 minutes to 12 hours. Also, the compound of formula (3) may be prepared from the compound of formula (4) by reductive alkylation treating with $C_{1-5}$ alkyl aldehyde. This reaction may be carried out in the presence of a reducing reagent such as sodium borohydride, sodium cyanoborohydryde in a reaction inert solvent such as methanol, ethanol and THF at about 30 to 150° C., usually from 50° C. to 100° C. for 30 minutes to 24 hours, usually 30 minutes to 12 hours. Then, the compound (3) may be subjected to hydrolysis to obtain a compound (Ia) under the same reaction conditions described in Scheme 1.

Scheme 3:

Further, compounds (Ia) may be prepared through the compound (Ia-1) (Compound (Ia) wherein $R^6$ is hydrogen) by a treating of the compound (3') with an acid to obtain a corresponding oxo-pyridine compound (Ia-1), followed by a introducing $R^6$ group to nitrogen atom of the compound (Ia-1), as indicated in the following Scheme 3.

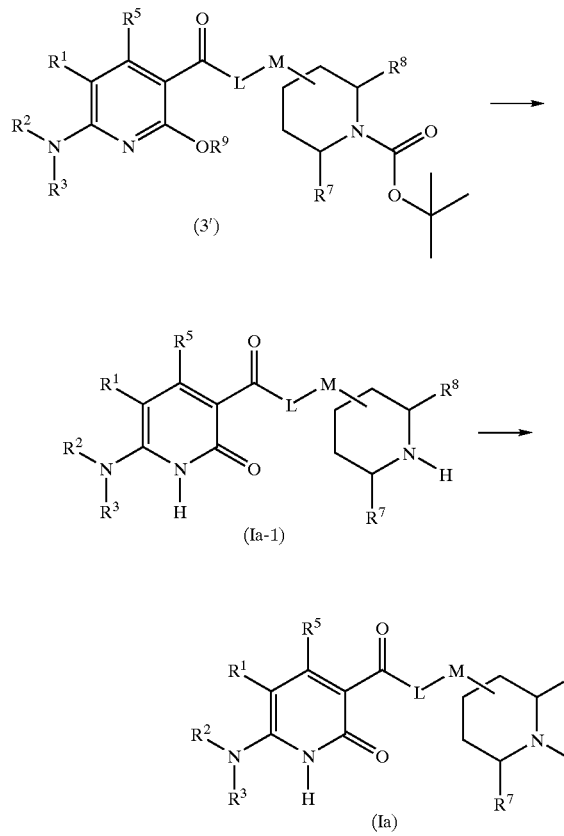

In Scheme 3, the hydrolysis can be carried out according to the conventional procedures. In a typical procedure, the hydrolysis is carried out by treatment with diluted hydrochloric acid in a suitable reaction-inert solvent such as methanol at a temperature in the range from 50° C. to the reflux temperature, usually from 70° C. to the reflux temperature for 30 minute to 24 hour, usually 2 to 15 hours. The introducing $R^6$ group to nitrogen atom of the compound (Ia-1) may be carried out under the similar conditions as described in Scheme 2.

Scheme 4:

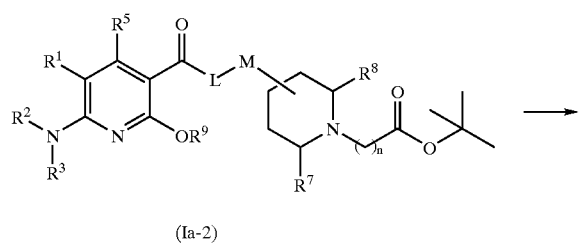

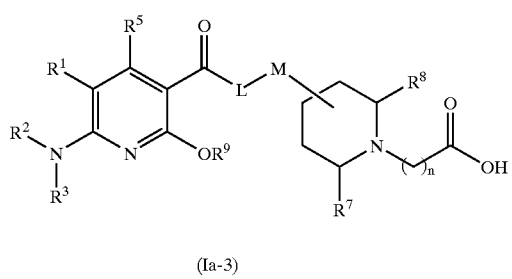

In Scheme 4, the compound (Ia-2) (Compound (Ia) wherein $R^6$ is —$(CH_2)nCO_2tBoc$) may be treated with an acid under the conventional procedure to obtain a compound (Ia-3) (Compound (Ia) wherein $R^6$ is —$(CH_2)nCO_2H$). In a typical procedure, the hydrolysis is carried out by treatment with diluted hydrochloric acid in a suitable reaction-inert solvent such as water at a temperature in the range from 50° C. to the reflux temperature, usually from 70° C. to the reflux temperature for 30 minute to 24 hour, usually 2 to 15 hours.

Scheme 5:

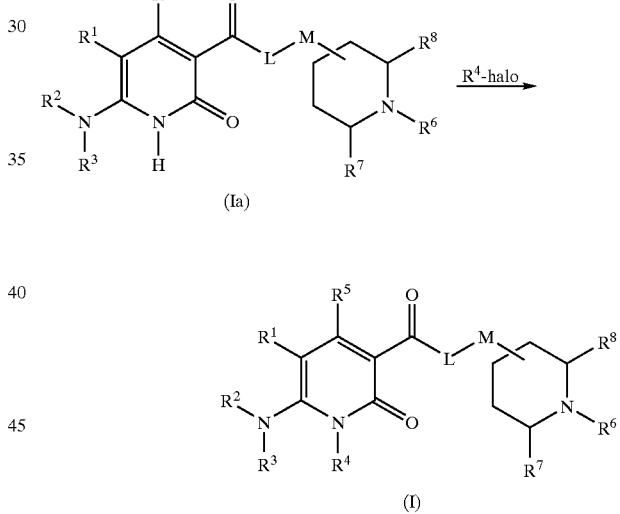

In scheme 5, the compound of formula (I) wherein $R^4$ is not hydrogen, may be prepared from the compound of formula (Ia) by methods known to those skilled in the art. The compound of formula (Ia) may be treated with appropriate halide derivatives, $R^4$-halo in the presence of a base such as sodium bicarbonate, sodium carbonate, potassium carbonate, sodium hydride, potassium t-butoxide, lithium diisopropylamide (LDA) and sodium amide in a reaction inert solvent such as THF and DMF at about −20 to 70° C., usually from −5° C. to 50° C. for 30 minutes to 24 hours, usually 30 minutes to 12 hours.

Scheme 6:

In Scheme 6, the compound (Ia-4) (Compound (Ia) wherein $R^1$ is hydrogen) may be prepared from the compound (3) wherein $R^1$ is halogen.

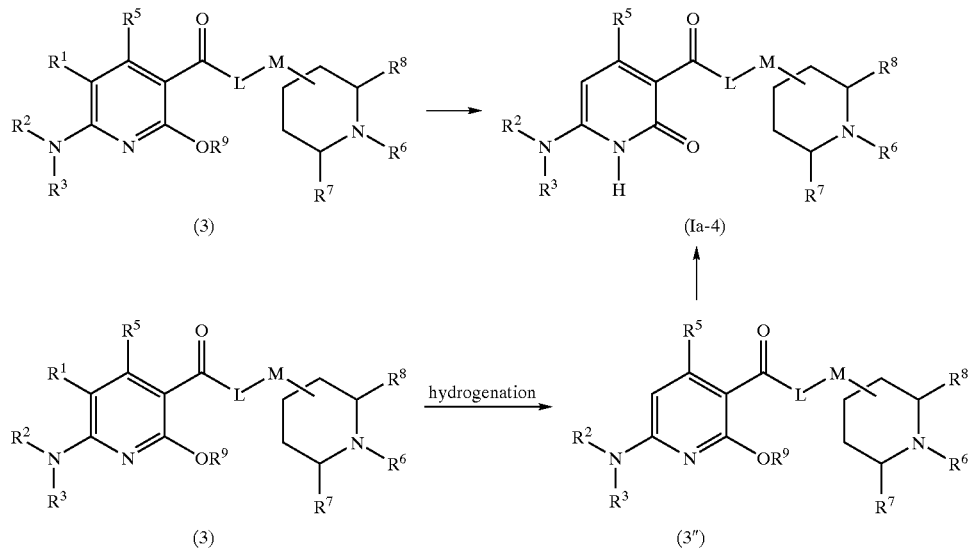

The compound (3) may be reacted with copper, copper (II) acetate or copper (I) chloride, to obtain a compound (Ia-4). This reaction can be carried out in a suitable reaction-inert solvent. Suitable solvents include, for example, methylimidazole, nitrobenzene and DMF. This reaction may be carried out at a temperature in the range from −20 to 100° C., usually from 0° C. to 50° C. for 30 minutes to 24 hours, usually 5 to 20 hours. This reaction may be carried out in the presence of a base such as sodium bicarbonate, sodium carbonate and potassium carbonate. Alternatively, the compound (Ia-4) can be prepared by subjecting a compound (3) to catalytic hydrogenation followed by hydrolysis. In Scheme 6, the catalytic hydrogenation can be carried out in the presence of hydrogen or hydrogen source such as ammonium formate, and a suitable metal containing catalysts such as palladium, platinum, nickel, platinum oxide and rhodium in a suitable reaction-inert solvent such as methanol. The preferred catalyst is palladium on carbon. This hydrogenation can be carried out at a temperature in the range from 20 to 100° C., usually from 25° C. to 80° C. for 5 minutes to 48 hours, usually 30 minutes to 24 hours. Then, the compound (3″) may be subjected to conventional hydrolysis to obtain the compound (Ia-4) under the same condition described in Scheme 1.

Scheme 7:

The pyridyl compounds (Ia-5) (Compound (Ia) wherein $R^1$ is aryl or heteroaryl; and $R^2$ and $R^3$ are hydrogen), may be prepared in the following reaction steps.

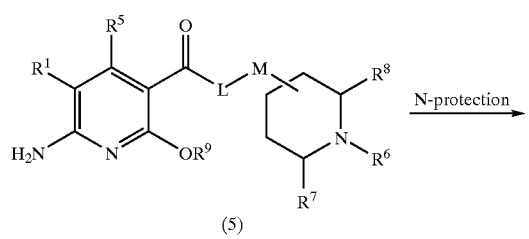

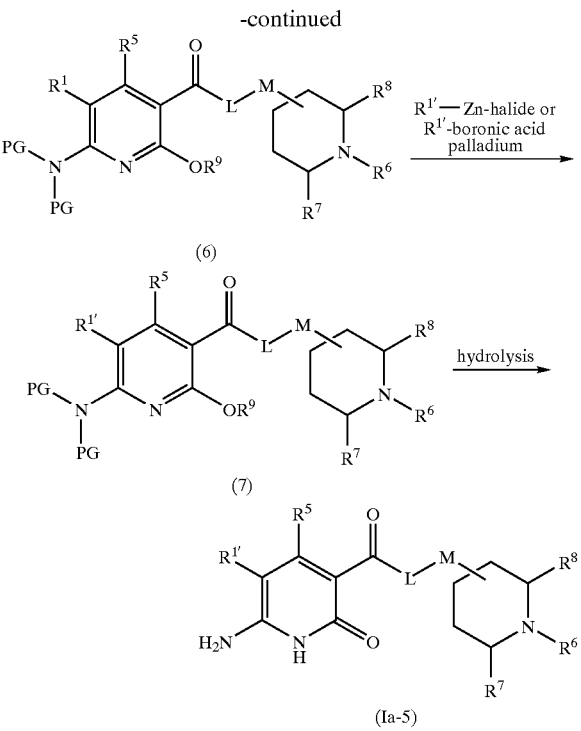

In Scheme 7, an amino group of compound (5) (Compound (Ia) wherein $R^1$ is halogen; and $R^2$ and $R^3$ are hydrogen) may be protected by a suitable protecting group, for example, methoxycarbonyl, ethoxycarbonyl, tert-butoxycarbonyl (Boc), or the like, to obtain a compound (6) wherein PG is a protecting group. This reaction may be carried out by a number of standard procedures known to those skilled in the art (e.g., "Protection for the Hydroxy Group and the Amino Group", in *Protective Groups in Organic Synthesis,* 2nd Edition, T. W. Greene and P. G. M. Wuts, Ed., John Wiley and Sons, Inc. 1991, pp. 10–142, 309–405). Suitable solvents include, for example, ethers such as tetrahydrofuran(THF), 1,2-dimethoxyethane, diethyl ether, diisopropyl ether, diphenyl ether and 1,4-dioxane. Suitable bases include, for example, triethyl amine, pyridine and 4-(dimethylamino)pyridine. This reaction may be carried out at a temperature in the range from −50 to 100° C., usually from −100° C. to 80° C. for 30 minutes to 24 hours, usually 30 minutes to 10 hours. The compound (6) may be treated with $R^{1'}$—Zn-halid or $R^{1'}$-boronic acid wherein $R^{1'}$ is aryl or heteroaryl, in the presence of palladium. This reaction can be carried out in a suitable reaction-inert solvent such as THF, toluene, dioxane, 1,2-dimetoxyethane, acetonitrile and DMF. This reaction may be carried out at a temperature in the range from 30° C. to 180° C., usually from 70° C. to the reflux temperature for 30 minutes to 48 hours, usually 30 minutes to 18 hours. Then, the compound (7) may be subjected to deprotection of an amino-protecting group and hydrolysis at once or separately, to obtain a compound (Ia-5). The deprotection may be carried out by a number of standard procedures known to those skilled in the art (e.g., "Protection for the Hydroxy Group and the Amino Group", in *Protective Groups in Organic Synthesis*, 2nd Edition, T. W. Greene and P. G. M. Wuts, Ed., John Wiley and Sons, Inc. 1991, pp. 10–142, 309–405). In a typical procedure, this reaction can be carried out by treatment with diluted hydrochloric acid in a suitable reaction-inert solvent such as methanol at a temperature in the range from 50° C. to the reflux temperature, usually from 70° C. to the reflux temperature for 30 minute to 24 hour, usually 1 to 10 hours.

Scheme 8:

The carboxylate compounds (1—1) and (1-2) used as starting materials in Scheme 1 may be prepared in the following reaction steps.

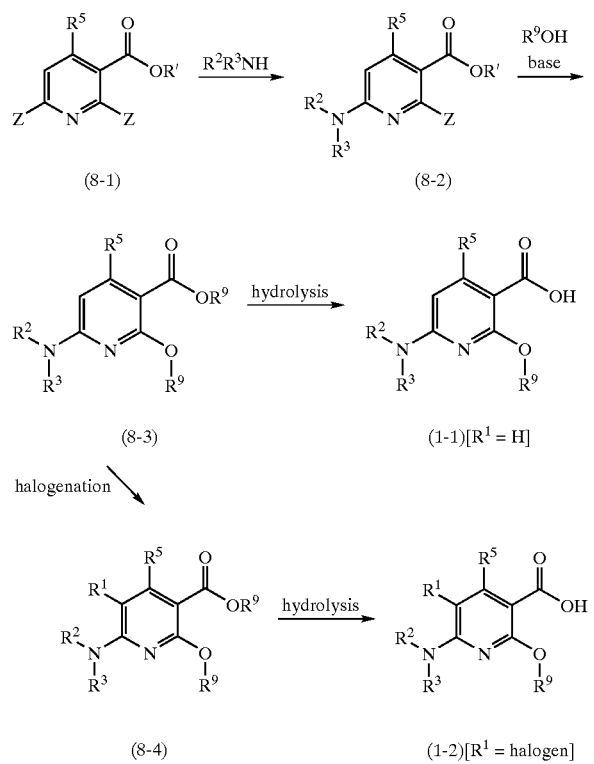

In Scheme 8, a nicotinate compound (8-1) wherein R' is $C_{1-3}$ alkyl and Z is halogen, may be reacted with an amine compound: $NHR^2R^3$, to obtain a compound (8-2). This reaction is generally carried out at a pressure from 1 to 5 atmospheres, preferably at 1 to 4 atmospheres. This reaction can be carried out in a suitable reaction-inert solvent. Suitable solvents include, for example, alcohols such as methanol, ethanol, propanol, butanol, 2-methoxyethanol and ethylene glycol; ethers such as tetrahydrofuran, 1,2-dimethoxyethane, diethyl ether, diisopropyl ether, diphenyl ether and 1,4-dioxane; halogenated hydrocarbons such as chloroform, dichloroethane and 1,2-dichloroethane; amides such as N,N-dimethylformamide and hexamethylphospholictriamide; sulfoxides such as dimethyl sulfoxide; acetonitrile; benzene, toluene, xylene; and pyridine. This reaction may be carried out at a temperature in the range from −50 to 100° C., usually from −30° C. to 50° C. for 30 minutes to 24 hours, usually 1 to 10 hours. Then, the compound (8-2) may be treated with an alcohol compound: $R^9OH$, in the presence of a base to obtain a compound (8-3). Suitable solvents include, for example, alcohols such as methanol, ethanol, propanol, butanol, 2-methoxyethanol and ethylene glycol; ethers such as tetrahydrofuran, 1,2-dimethoxyethane, diethyl ether, diisopropyl ether, diphenyl ether and 1,4-dioxane; halogenated hydrocarbons such as chloroform, dichloroethane and 1,2-dichloroethane; amides such as N,N-dimethylformamide and hexamethylphospholictriamide; sulfoxides such as dimethyl sulfoxide; acetonitrile; benzene, toluene, xylene; and pyridine. This reaction may be carried out at a temperature in the range from 0° C. to the reflux temperature, usually from 20° C. to the reflux temperature for 30 minutes to 24 hours, usually 30 minutes to 5 hours. Suitable bases include, for example, sodium hydride and potassium t-butoxide and potassium carbonate. When $R^1$ is halo, the compound (8-3) is treated with halogen or N-halogenated succimide or SELECTFLUOR (trademark) under appropriate conditions, to obtain a compound (8-4) wherein $R^1$ is halo. This reaction can be carried out in a suitable reaction-inert solvent such as halogenated hydrocarbons such as chloroform, dichloroethane and 1,2-dichloroethane; amides such as N,N-dimethylformamide and hexamethylphospholictriamide; sulfoxides such as dimethyl sulfoxide; acetonitrile. This reaction may be carried out at a temperature in the range from 0 to 150° C., usually from 25 to 90° C. for 5 minutes to 24 hours, usually 30 minutes to 8 hours. The hydrolysis of compounds (8-3) and (8-4) may be carried out by conventional procedures. In a typical procedure, the hydrolysis is carried out by treatment with sodium hydroxide, potassium hydroxide or lithium hydroxide in a suitable reaction-inert solvent. Suitable solvents include, for example, alcohols such as methanol, ethanol, propanol, butanol, 2-methoxyethanol, and ethylene glycol; ethers such as tetrahydrofuran, 1,2-dimethoxyethane, and 1,4-dioxane; halogenated hydrocarbons such as chloroform, dichloroethane, and 1,2-dichloroethane; amides such as N,N-dimethylformamide and hexamethylphospholictriamide; and sulfoxides such as dimethyl sulfoxide. This reaction may be carried out at a temperature in the range from −20 to 150° C., usually from 20° C. to 100° C. for 30 minutes to 24 hours, usually 60 minutes to 10 hour.

Scheme 9:

Alternatively, the carboxylate compounds (1—1) and (1-2) used as starting materials in Scheme 1 may also be prepared in the following reaction steps.

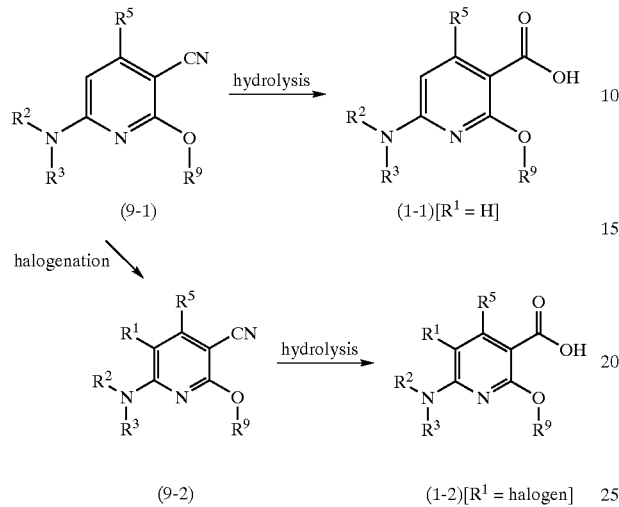

The nitrile compound (9-1) may be converted to the carboxylate compounds (1—1) and (1-2) respectively according to the similar procedure as described in Scheme 8.

Scheme 10:

The amine compound (2) used as starting materials in Scheme 1 may be prepared in the following reaction steps.

The amine compound (2) may be prepared by introducing $R^6$ group to an amine compound (10-1) to obtain a corresponding $R^6$—N amine compound (10-2), followed by reduction of the compound (10-2) with a reducing agent, as indicated in the following Scheme 10.

The introducing $R^6$ group to nitrogen atom of the compound (10-1) may be carried out under the similar conditions as described in Scheme 2. The reduction of carbonyl group of compound (10-2) may be carried out by conventional procedures. In a typical procedure, the reduction is carried out by treatment with lithium aluminum hydride, lithium borohydride or boran in a suitable reaction-inert solvent. Suitable solvents include, for example, ethers such as tetrahydrofuran, 1,2-dimethoxyethane, and 1,4-dioxane. This reaction may be carried out at a temperature in the range from −20 to 100° C., usually from 20° C. to 65° C. for 30 minutes to 24 hours, usually 60 minutes to 10 hour.

Scheme 11:

The compounds of formula (Ia-6) and (IIa) wherein L is $CR^{11}R^{12}$; $R^2$ and $R^3$ are hydrogen; and all other symbols are as already defined, may be prepared in the following reaction steps.

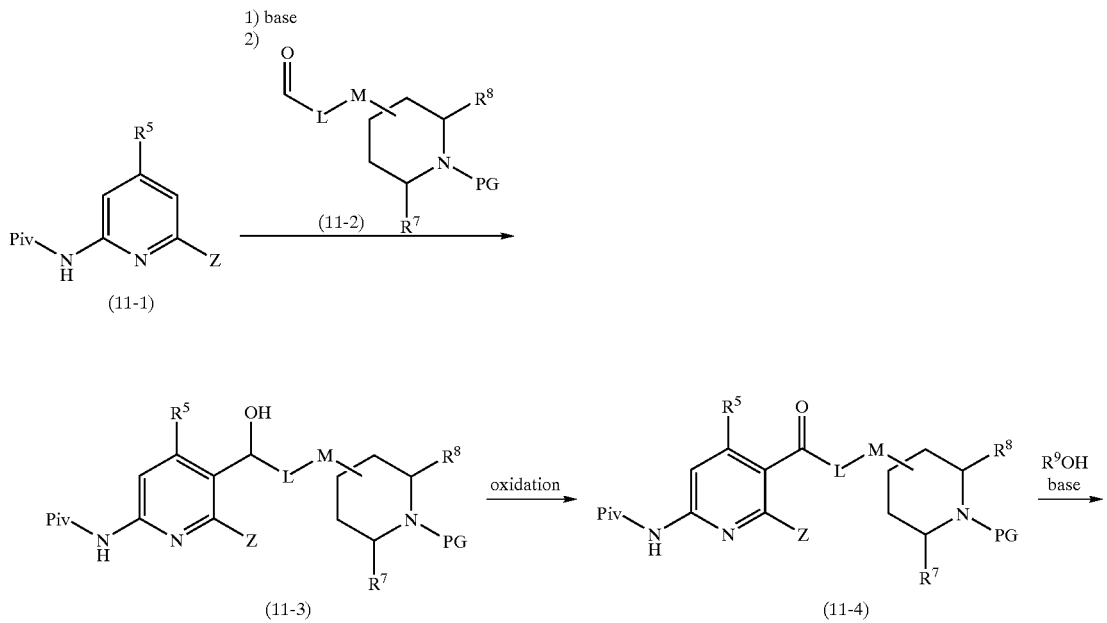

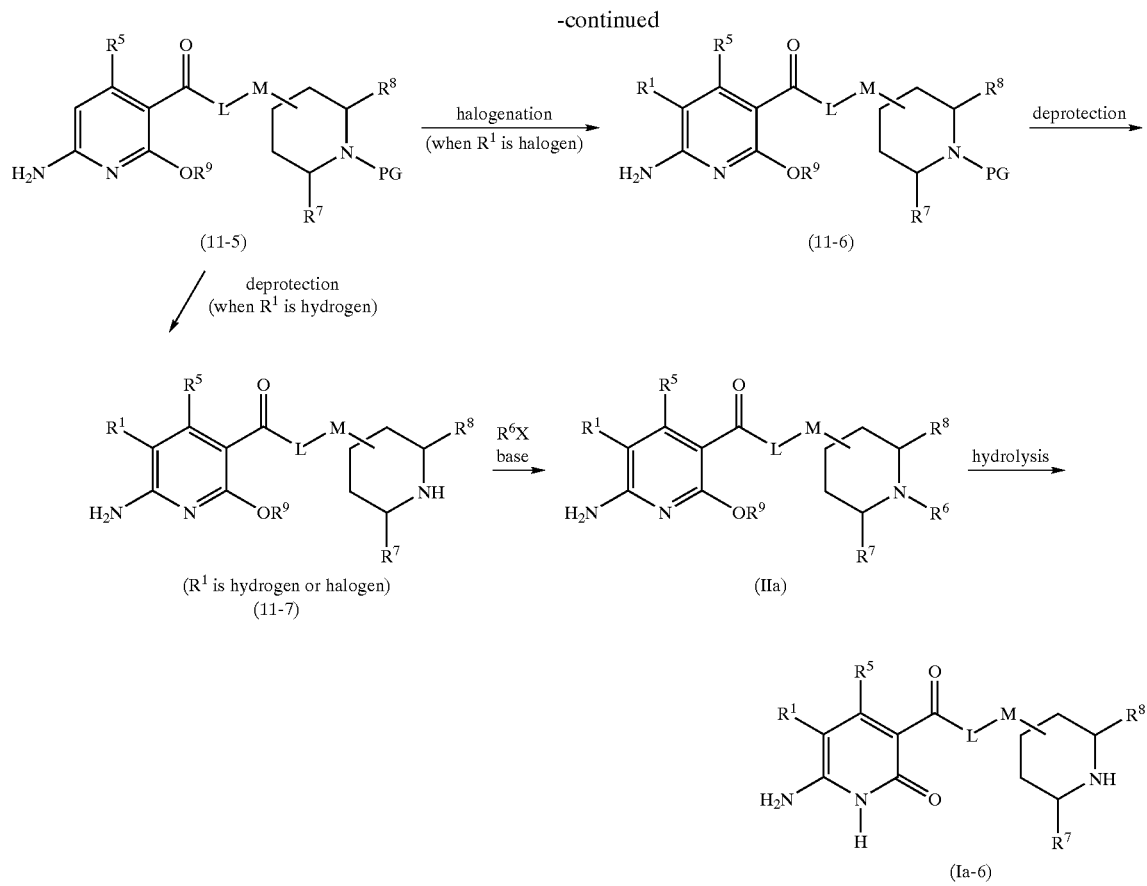

In Scheme 11, a pyridine compound (11-1) may be treated with a base such as n-BuLi or lithium diisopropylamide, followed by an aldehyde compound (11-2) wherein PG is defined above, to obtain a compound (11-4). This reaction can be carried out in a suitable reaction-inert solvent. Suitable solvents include, for example, ethers such as tetrahydrofuran, 1,2-dimethoxyethane, diethyl ether, diisopropyl ether, diphenyl ether and 1,4-dioxane. This reaction may be carried out at a temperature in the range from −50 to 100° C., usually from 0° C. to 80° C. for 30 minutes to 24 hours, usually 30 minutes to 10 hours. The compound (11-3) may be treated with an oxidizing agent, for example, oxalyl chloride-dimethylsulfoxide (Swern oxidation condition), pyridinium chlorochromate (PCC), pyridinium dichromate (PDC), manganese dioxide, tetrapropylammonium perruthenate (TPAP), or the like, to obtain a compound (11-4). This reaction can be carried out in a suitable reaction-inert solvent such as halogenated hydrocarbons such as chloroform, dichloroethane and 1,2-dichloroethane. This reaction may be carried out at a temperature in the range from −100 to 80° C., usually from −80 to 50° C. for 5 minutes to 30 hours, usually 15 minutes to 20 hours. Then, the compound (11-4) may be subject to alkoxylation according to the similar procedure described in Scheme 8. When $R^1$ is halogen, the obtained alkoxy compound may be subjected to halogenation according to the similar procedure described in Scheme 8. The deprotection of an amino-protecting group of compounds (11-5) wherein $R^1$ is hydrogen, and (11-6) wherein $R^1$ is halogen, to obtain a compound (11-7). The deprotection may be carried out by a number of standard procedures known to those skilled in the art (e.g., "Protection for the Hydroxy Group and the Amino Group ", in *Protective Groups in Organic Synthesis,* 2nd Edition, T. W. Greene and P. G. M. Wuts, Ed., John Wiley and Sons, Inc. 1991, pp. 10–142, 309–405). Then, introducing $R^6$ group to nitrogen atom in piperidine ring may be carried out under the similar conditions described in Scheme 2. The obtained compound (IIa) may be subjected to hydrolysis to provide a compound (Ia-6) according to the similar procedure described in Scheme 1.

Scheme 12:

The bicyclic carboxylic acid compound (12-5) may be prepared in the following reaction steps.

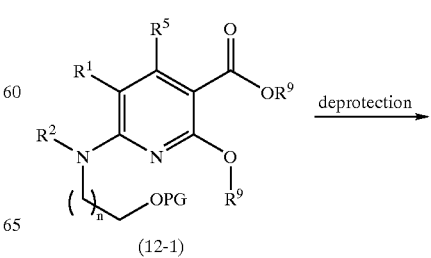

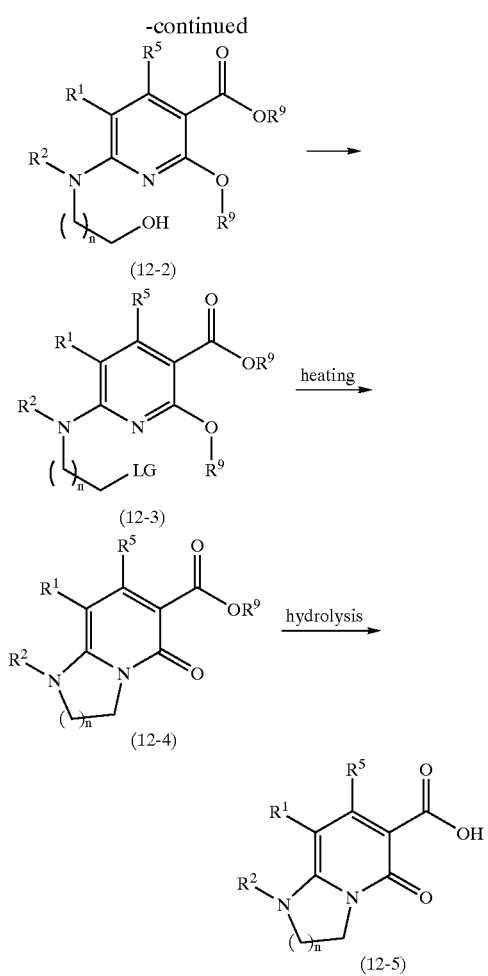

The compound (12-1) can be prepared by the similar procedure described in Scheme 8. The deprotection of compound 12-1 may be carried out by a number of standard procedures known to those skilled in the art as described in Scheme 11. The hydroxy group of compound 12-2 may be converted to the leaving group according to the conventional procedure. In a typical procedure, the conversion is carried out by treatment with p-toluenesulfonyl chloride, methanesulfonyl chloride or trifluoromethanesulfonyl anhydride in the presence of a base in a suitable reaction-inert solvent. Suitable bases include, for example, pyridine, triethyl amine, lutidine and dimethylaminopyridine. Suitable solvents include, for example, ethers such as tetrahydrofuran, 1,2-dimethoxyethane, and 1,4-dioxane; and halogenated hydrocarbons such as chloroform, dichloroethane, and 1,2-dichloroethane. This reaction may be carried out at a temperature in the range from −20 to 100° C., usually from 20° C. to 80° C. for 30 minutes to 24 hours, usually 60 minutes to 10 hour. The obtained compound (12-3 wherein LG is a leaving group, such as p-toluenesulfonyloxy, methanesulfonyloxy or trifluoromethanesulfonyloxy and the like) may be heated in a suitable reaction inert solvent. Suitable solvents include, for example, alcohols such as methanol, ethanol, propanol, butanol, 2-methoxyethanol, and ethylene glycol; ethers such as tetrahydrofuran, 1,2-dimethoxyethane, and 1,4-dioxane; halogenated hydrocarbons such as chloroform, dichloroethane, and 1,2-dichloroethane; amides such as N,N-dimethylformamide and hexamethylphospholictriamide; and sulfoxides such as dimethyl sulfoxide. This reaction may be carried out at a temperature in the range from 0° C. to the reflux temperature, usually from 20° C. to the reflux temperature for 30 minutes to 24 hours, usually 60 minutes to 10 hour. The hydrolysis of compound (12-4) may be carried out by similar procedure described in Scheme 8.

Scheme 13:

When $R^5$ is trifluoromethyl, the oxy-pyridine compounds (9-1) used as starting materials in Scheme 9 may be prepared in the following reaction steps.

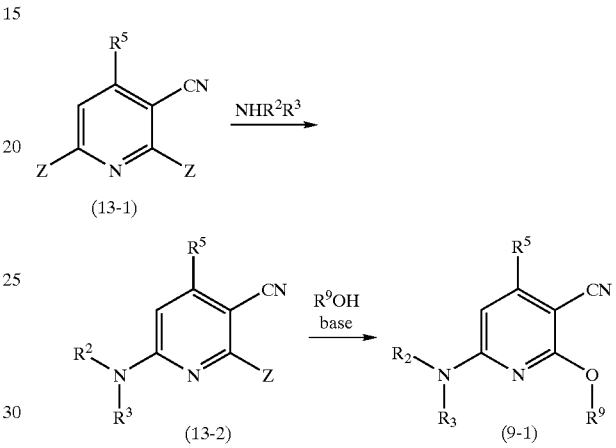

A dihalopyridine compound (13-1) may be treated with the amine compound: $NHR^2R^3$, to obtain a compound (13-2) according to the similar procedure described in Scheme 8. The alkoxylation of compound (13-2) may be carried out by conventional procedure described in Scheme 8 to provide compound (9-1).

Scheme 14:

When L is $CHR^{11}$; Y is methylene; $R^7$ and $R^8$ are hydrogen; and PG is Boc, the aldehyde compounds (14-7) used as in Scheme 11 may be prepared in the following reaction steps.

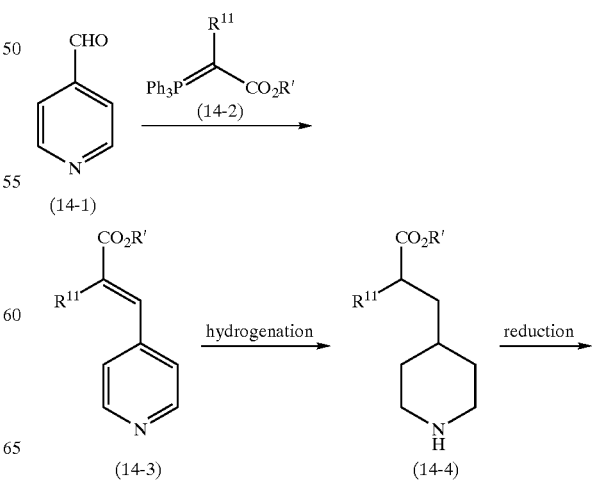

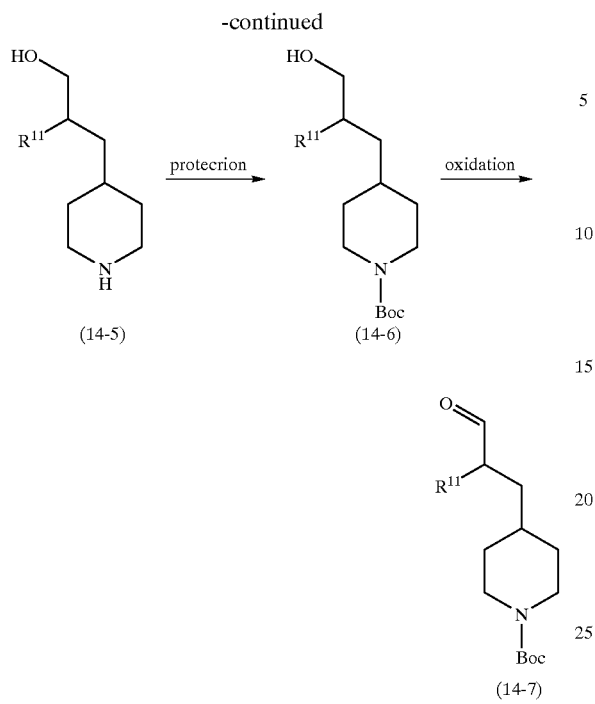

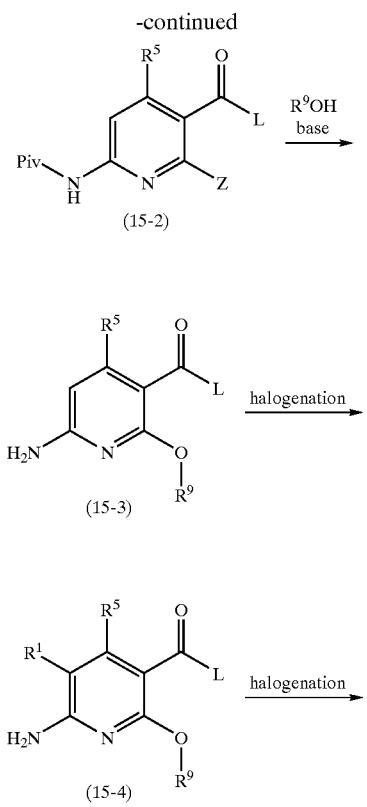

A pyridine compound (14-1) may be treated with Wittig reagent (14-2) to obtain a compound (14-3). This reaction can be carried out at a temperature in the range from 0° C. to the reflux temperature, usually from 25° C. to the reflux temperature for 5 minutes to 48 hours, usually 30 minutes to 12 hours. The compound (14-4) can be prepared by subjecting a compound (14-3) to catalytic hydrogenation followed by hydrolysis. This hydrogenation can be carried out by the similar procedure described in Scheme 6. Then, the compound (14-4) may be subjected to conventional reduction to obtain the compound (14-5) under the same condition described in Scheme 10. The protection of nitrogen group of compound (14-6) followed by the oxidation of hydroxy group to afford the aldehyde compound (14-7) by similar procedures described in Scheme 7 and 11.

Scheme 15:

The compound (Ia-7) (Compound (I) wherein $R^2$ and $R^3$ are hydrogen; $R^4$ is hydrogen; L is $(CR^{11}R^{12})n$ and M is O or $NR^{11}$), may be prepared in the following reaction steps.

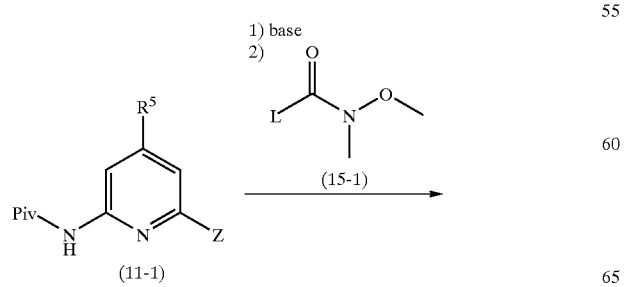

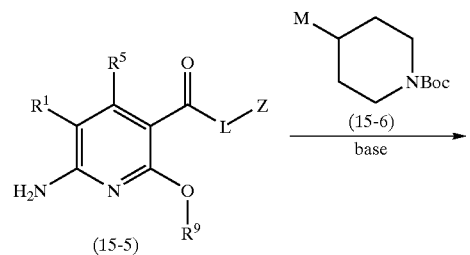

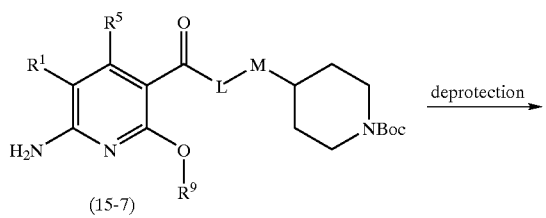

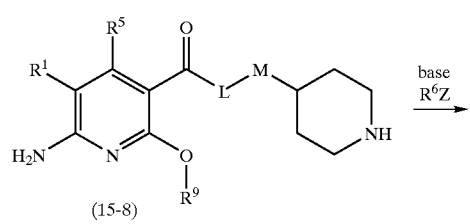

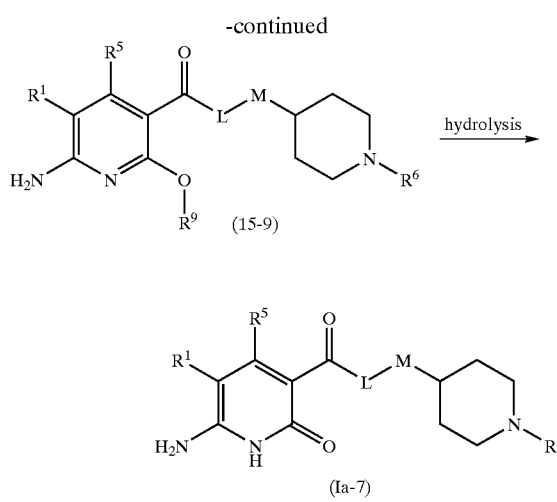

(15-9)

(Ia-7)

The compound (11-1) may be treated with a base such as n-BuLi or lithium diisopropylamide, followed by a Weinreb amide compound (15-1) to afford compound (15-2). This reaction can be carried out in a suitable reaction-inert solvent. Suitable solvents include, for example, ethers such as tetrahydrofuran, 1,2-dimethoxyethane, diethyl ether, diisopropyl ether, diphenyl ether and 1,4-dioxane. This reaction may be carried out at a temperature in the range from −100 to 100° C., usually from −90° C. to 50° C. for 30 minutes to 24 hours, usually 30 minutes to 10 hours. The alkoxylation of compound (15-2) followed by halogenation may be carried out by conventional procedures described in Scheme 8 to provide compound (15-4). The halogenation of □-position of carbonyl group of compound (15-4) may be carried out in the presence of a suitable halogen under the acidic condition. Suitable halogen include chlorine, bromine and iodine. Suitable acids include hydrogen bromide, acetic acid and hydrogen chloride. This reaction may be carried out at a temperature in the range from −20 to 150° C., usually from 0° C. to 120° C. for 30 minutes to 100 hours, usually 5 hours to 30 hours. The halide compound (15-5) may be coupled with the piperidine compound (15-6) to give a compound (15-7). The coupling reaction may be carried out in the presence of a suitable base in a reaction-inert solvent. Suitable bases include sodium bicarbonate, sodium carbonate, potassium carbonate, triethyl amine and diisopropyl ethyl amine. Suitable reaction-inert solvents include aqueous or non-aqueous organic solvents such as tetrahydrofuran, N,N-dimethylformamide (DMF), dioxane, acetone, dimethoxyethane and acetonitrile; and halogenated hydrocarbons such as chloroform, dichloromethane and dichloroethane. This reaction may be carried out at a temperature in the range from −20 to 150° C., usually from 0° C. to 100° C. for 30 minutes to 100 hours, usually 5 hours to 30 hours. The deprotection of compound (15-7) may be carried out by conventional procedures described in Scheme 11. The introducing $R^6$ group to nitrogen atom of piperidine ring, followed by hydrolysis may afford the compound (Ia-7) by similar procedure described in Scheme 11 and 2.

Scheme 16:

The compound (Ia-8) (Compound (I) wherein $R^6$ is $R^{11}R^{12}NC(=O)CH(R^d)$—), may be prepared in the following reaction steps.

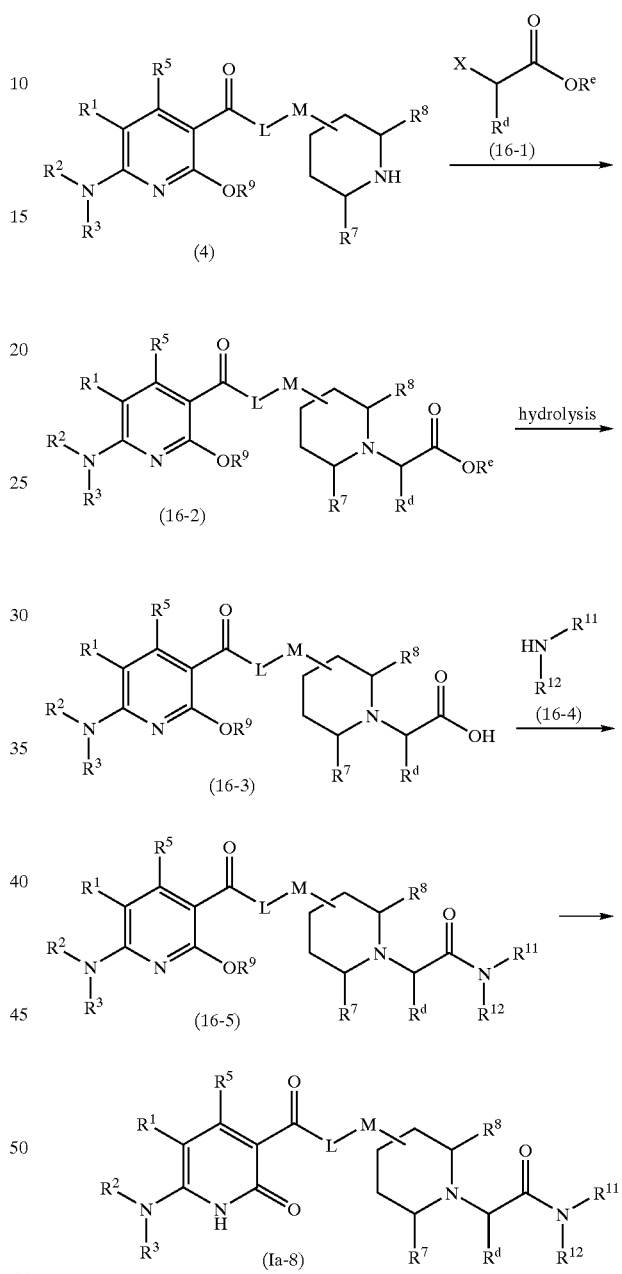

In scheme 16, $R^d$ is $C_{1-11}$ alkyl and $R^e$ is $C_{1-6}$ alkyl. The compound of formula (4) may be treated with appropriate halide derivatives (16-1 wherein X is halo) in the absence of or presence of a base such as sodium bicarbonate, sodium carbonate, potassium carbonate, cesium carbonate, triethyl amine and diisopropyl ethyl amine in a reaction inert solvent such as THF and DMF at about 30 to 150° C., usually from 50° C. to 100° C. for 30 minutes to 24 hours, usually 30 minutes to 12 hours. The hydrolysis of compounds (16-2) may be carried out by conventional procedures. In a typical procedure, the hydrolysis is carried out by treatment with sodium hydroxide, potassium hydroxide or lithium hydroxide in a suitable reaction-inert solvent. Suitable solvents include, for example, alcohols such as methanol, ethanol, propanol, butanol, 2-methoxyethanol, and ethylene glycol; ethers such as tetrahydrofuran, 1,2-dimethoxyethane, and 1,4-dioxane; halogenated hydrocarbons such as chloroform, dichloroethane, and 1,2-dichloroethane; amides such as N,N-dimethylformamide and hexamethylphospholictriamide; and sulfoxides such as dimethyl sulfoxide. This reaction may be carried out at a temperature in the range from −20 to 150° C., usually from 20° C. to 100° C. for 30 minutes to 24 hours, usually 60 minutes to 10 hour. The carboxylic acid compound (16-3) may be coupled with the amine compound (16-4) to give an amide compound (16-5). The coupling reaction may be carried out in the presence of a suitable condensation agent in a reaction-inert solvent. Suitable condensation agents include 1,1'-carbonyldiimidazole (CDI), diisopropylcarbodiimide (DIC), dicyclohexylcarbodiimide (DCC), water soluble carbodiimide (WSC), 2-ethoxy-N-ethoxycarbonyl-1,2-dihydroquinoline, benzotriazol-1-yloxy-tris(dimethylamino) phosphonium hexafluorophosphate (BOP), diethyl azodicarboxylate-triphenylphosphine, diethylcyanophosphonate (DEPC), diphenylphosphorylazide (DPPA), bromotripyrrolidino phosphonium hexafluorophosphate (PyBrop[trademark]), bis(2-oxo-3-oxazolidinyl) phosphinic chloride (BOPCl), benzotriazole-1-yl-oxy-tris-pyrrolidino-phosphonium hexafluorophosphate (PyBOP), 2-(1-H-benzotriazole-1-yl)-1,1,3,3,-tetramethyluronium hexafluorophosphate (HBTU) and ethyl chloroformate. Suitable reaction-inert solvents include aqueous or non-aqueous organic solvents such as tetrahydrofuran, N,N-dimethylformamide (DMF), dioxane, acetone, dimethoxyethane and acetonitrile; and halogenated hydrocarbons such as chloroform, dichloromethane and dichloroethane (preferably dichloromethane). This reaction may be carried out at a temperature in the range from −20 to 80° C., usually from 0° C. to 30° C. for 30 minutes to 100 hours, usually 5 hours to 30 hours. The obtained compound (16-5) may be subjected to hydrolysis to provide a compound (Ia-8) according to the similar procedure described in Scheme 1.

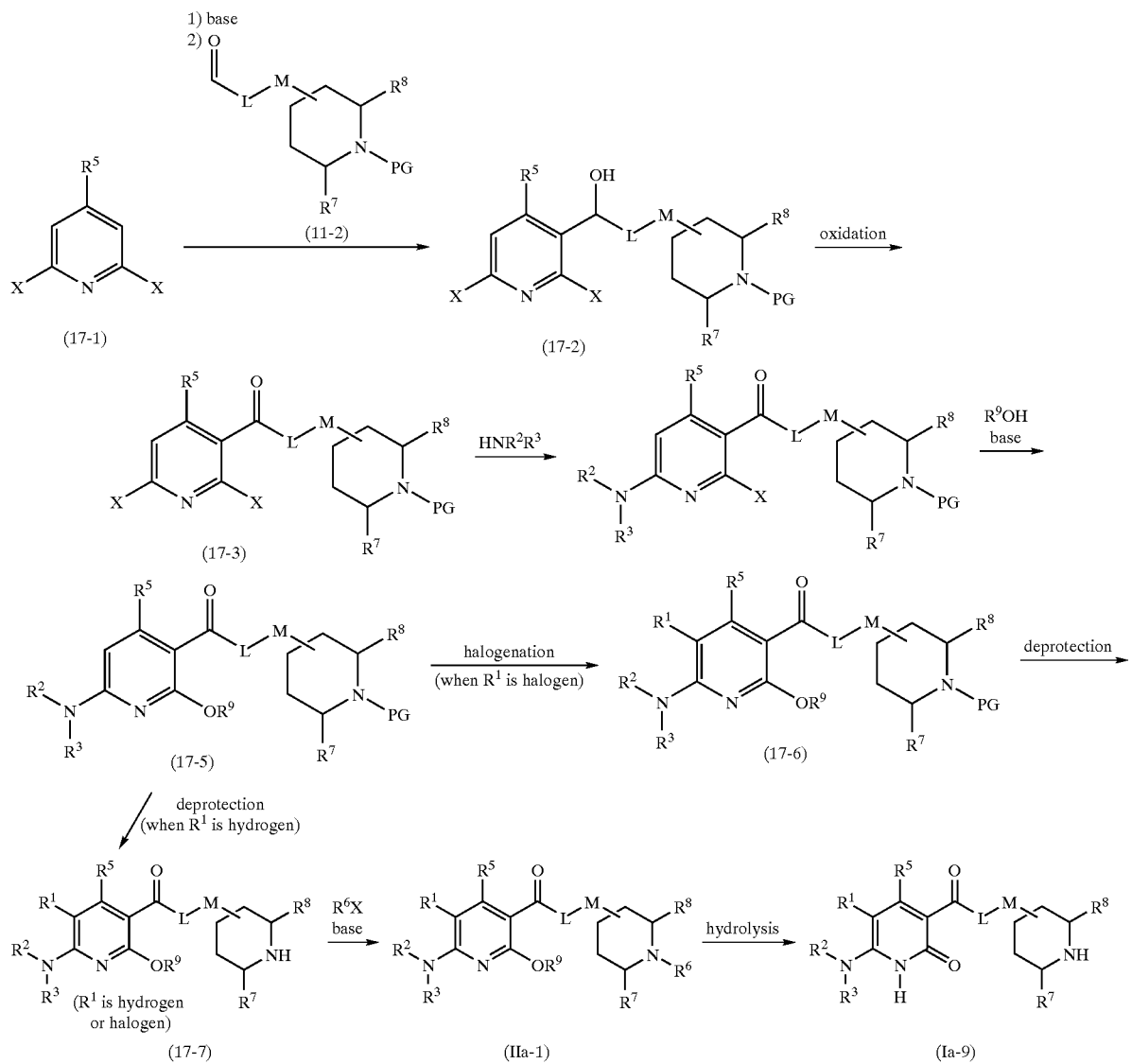

In Scheme 17, a pyridine compound (17-1) may be treated with a base such as n-BuLi or lithium diisopropylamide, followed by an aldehyde compound (11-2) wherein PG is defined above, to provide a compound (17-2). This reaction can be carried out in a suitable reaction-inert solvent. Suitable solvents include, for example, ethers such as tetrahydrofuran, 1,2-dimethoxyethane, diethyl ether, diisopropyl ether, diphenyl ether and 1,4-dioxane. This reaction may be carried out at a temperature in the range from −50 to 100° C., usually from 0° C. to 80° C. for 30 minutes to 24 hours, usually 30 minutes to 10 hours. The compound (17-2) may be treated with an oxidizing agent, for example, oxalyl chloride-dimethylsulfoxide (Swern oxidation condition), pyridinium chlorochromate (PCC), pyridinium dichromate (PDC), manganese dioxide, tetrapropylammonium perruthenate (TPAP), or the like, to obtain a compound (17-3). This reaction can be carried out in a suitable reaction-inert solvent such as halogenated hydrocarbons such as chloroform, dichloroethane and 1,2-dichloroethane. This reaction may be carried out at a temperature in the range from −100 to 80° C., usually from −80 to 50° C. for 5 minutes to 30 hours, usually 15 minutes to 20 hours. The compound of (17-3) may be reacted with an amine compound: $NHR^2R^3$, to obtain a compound (17-4). This reaction is generally carried out at a pressure from 1 to 5 atmospheres, preferably at 1 to 4 atmospheres. This reaction can be carried out in a suitable reaction-inert solvent. Suitable solvents include, for example, alcohols such as methanol, ethanol, propanol, butanol, 2-methoxyethanol and ethylene glycol; ethers such as tetrahydrofuran, 1,2-dimethoxyethane, diethyl ether, diisopropyl ether, diphenyl ether and 1,4-dioxane; halogenated hydrocarbons such as chloroform, dichloroethane and 1,2-dichloroethane; amides such as N,N-dimethylformamide and hexamethylphospholictriamide; sulfoxides such as dimethyl sulfoxide; acetonitrile; benzene, toluene, xylene; and pyridine. This reaction may be carried out at a temperature in the range from −50 to 100° C., usually from −30° C. to 50° C. for 30 minutes to 24 hours, usually 1 to 10 hours. Then, the compound (17-4) may be subject to alkoxylation according to the similar procedure described in Scheme 8. When $R^1$ is halogen, the obtained alkoxy compound may be subjected to halogenation according to the similar procedure described in Scheme 8. The deprotection of an amino-protecting group of compounds (17-5) wherein $R^1$ is hydrogen, and (17-6) wherein $R^1$ is halogen, to obtain a compound (17-7). The deprotection may be carried out by a number of standard procedures known to those skilled in the art (e.g., "Protection for the Hydroxy Group and the Amino Group", in *Protective Groups in Organic Synthesis,* 2nd Edition, T. W. Greene and P. G. M. Wuts, Ed., John Wiley and Sons, Inc. 1991, pp. 10–142, 309–405). Then, introducing $R^6$ group to nitrogen atom in piperidine ring may be carried out under the similar conditions described in Scheme 2. The obtained compound (IIa-1) may be subjected to hydrolysis to provide a compound (Ia-9) according to the similar procedure described in Scheme 1.

Scheme 18:

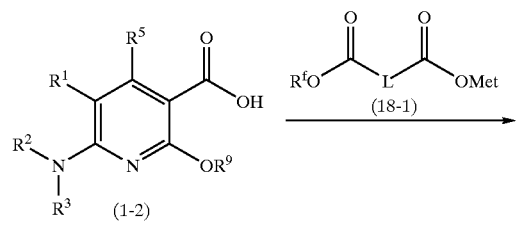

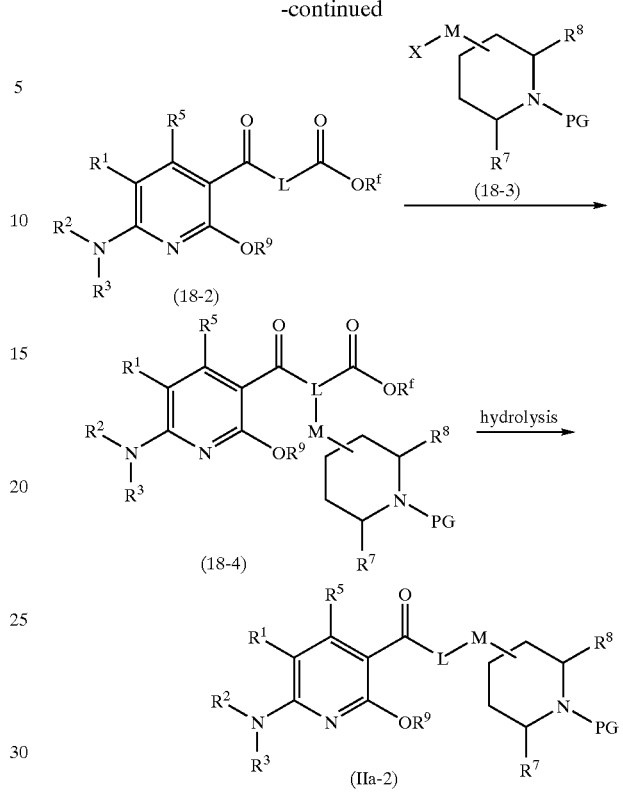

In Scheme 18, $R^f$ is $C_{1-6}$ alkyl, X is halo or methylsulfonyl and Met is lithium, sodium or potassium. The compound of formula (1-2) may be treated with the compound of formula (18-1) under the Masamune Reaction condition. This reaction may be carried out in the presence of a coupling agent, for example, 1,1'-carbonyldiimidazole (CDI), diisopropylcarbodiimide (DIC), dicyclohexylcarbodiimide (DCC), water soluble carbodiimide (WSC), 2-ethoxy-N-ethoxycarbonyl-1,2-dihydroquinoline, benzotriazol-1-yloxy-tris(dimethylamino) phosphonium hexafluorophosphate (BOP), diethyl azodicarboxylate-triphenylphosphine, diethylcyanophosphonate (DEPC), diphenylphosphorylazide (DPPA), bromotripyrrolidino phosphonium hexafluorophosphate (PyBrop[trademark]), bis(2-oxo-3-oxazolidinyl) phosphinic chloride (BOPCl), benzotriazole-1-yl-oxy-tris-pyrrolidino-phosphonium hexafluorophosphate (PyBOP), 2-(1-H-benzotriazole-1-yl)-1,1,3,3,-tetramethyluronium hexafluorophosphate (HBTU) and ethyl chloroformate. This reaction may be carried out in the presence of a catalyst, for example, magnesium chloride, magnesium bromide, magnesium iodide, calcium chloride, calcium bromide and calcium iodide. This reaction can be carried out in a suitable reaction-inert solvent such as halogenated hydrocarbons such as chloroform, dichloroethane, 1,2-dichloroethane, THF, acetonitrile, dimethylformamide and dimethylsulfoxide. This reaction may be carried out at a temperature in the range from 0 to 80° C., usually from 0 to 50° C. for 5 minutes to 30 hours, usually 15 minutes to 20 hours. The obtained compound formula (18-2) may be coupled with the compound of formula (18-3). A pyridine compound (18-2) may be treated with a base such as, sodium hydride or potassium carbonate, cesium carbonate, triethyl amine or diisopropyl ethylamine, followed by the compound of formula (18-3) wherein PG is defined above, to obtain a compound (18-4).

This reaction can be carried out in a suitable reaction-inert solvent. Suitable solvents include, for example, ethers such as tetrahydrofuran, 1,2-dimethoxyethane, diethyl ether, diisopropyl ether, diphenyl ether and 1,4-dioxane or acetone. This reaction may be carried out at a temperature in the range from −50 to 100° C., usually from 0C to 80° C. for 30 minutes to 24 hours, usually 30 minutes to 10 hours. The hydrolysis of compounds (18-4) may be carried out by conventional procedures. In a typical procedure, the hydrolysis is carried out by treatment with sodium hydroxide, potassium hydroxide or lithium hydroxide in a suitable reaction-inert solvent. Suitable solvents include, for example, alcohols such as methanol, ethanol, propanol, butanol, 2-methoxyethanol, and ethylene glycol; ethers such as tetrahydrofuran, 1,2-dimethoxyethane, and 1,4-dioxane; halogenated hydrocarbons such as chloroform, dichloroethane, and 1,2-dichloroethane; amides such as N,N-dimethylformamide and hexamethylphospholictriamide; and sulfoxides such as dimethyl sulfoxide. This reaction may be carried out at a temperature in the range from −20 to 150° C., usually from 20° C. to 100° C. for 30 minutes to 24 hours, usually 60 minutes to 10 hour.

In addition, starting compounds of formula 3, 3', 5, 8-1, 10-1, 11-1, 12-1, 15-1 and 18-3 are known or may be prepared from a known compound according to procedures known to those skilled in the art.

The present invention includes salt forms of the compounds (I) and (II) as obtained above. Insofar as the oxo or oxy-pyridine compounds of this invention are basic compounds, they are capable of forming a wide variety of different salts with various inorganic or organic acids.

The acids which are used to prepare the pharmaceutically acceptable acid addition salts of the aforementioned oxo or oxy-pyridine base compounds of formula (I) and (II) are those which form non-toxic acid addition salts, i.e., salts containing pharmaceutically acceptable anions, such as the chloride, bromide, iodide, nitrate, sulfate or bisulfate, phosphate or acid phosphate, acetate, lactate, citrate or acid citrate, tartrate or bi-tartrate, succinate, malate, fumarate, gluconate, saccharate, benzoate, methanesulfonate, ethanesulfonate, benzenesulfonate, p-toluenesulfonate and pamoate (i.e., 1.1'-methylene-bis-(2-hydroxy-3-naphthoate). The acid addition salts can be prepared by conventional procedures.

The compounds of formula (I) and (II) of this invention may contain one or more asymmetric centers. Thus, the compounds can exist in separated (+)- and (−)-optically active forms, as well as in the racemic form thereof. The present invention includes all such forms within its scope. Individual isomers can be obtained by known methods, such as optically selective reaction or chromatographic separation in the preparation of the final product or its intermediate.

In addition, when the compounds of this invention form hydrates or solvates they are also within the scope of this invention.

The oxo or oxy-pyridine compounds of this invention have $5\text{-HT}_4$ receptor binding activity (e.g., agonist or antagonist activities), and thus are useful for the treatment or prevention of gastroesophageal reflux disease, gastrointestinal disease, gastric motility disorder, upper gut motility disorder, non-ulcer dyspepsia, irritable bowel syndrome, constipation, dyspepsia, esophagitis, gastroesophageral disease, nausea, central nervous system disease, alzheimers disease, cognitive disorder, emesis, migraine, neurological disease, pain, ischaemic stroke, anxiety, cardiovascular disorders such as cardiac failure and heart arryhthmia, or the like in mammalian, especially human.

The compounds of the invention may advantageously be employed in combination with one or more other therapeutic ingredients selected from an antibiotic, anti-fungal and anti-viral agent.

Method for Assessing Biological Activities

The $5\text{-HT}_4$ receptor binding affinity of the compounds of this invention are determined by the following procedures.

Membrane Preparation

Pig heads are supplied from an abattoir. Striatal tissues are dissected, weighed and homogenized in 15 volumes of 50 mM ice-cold HEPES (pH 7.5) in a Polytron homogenizer (30 sec at full speed). Suspension is centrifuged at 48,000 g and 4° C. for 15 min. The resulting pellet is resuspended in an appropriate volume of 50 mM ice-cold HEPES, dispensed into aliquots and stored at −80° C. until use.

Bovine heads are also supplied from an abattoir. Striatal tissues are dissected, weighed and homogenized in 20 volumes of 50 mM ice-cold Tris-HCl (pH 7.4) in a Polytron homogenizer (30 sec at full speed). Suspension is centrifuged at 20,000 g and 4° C. for 30 min. The resulting pellet is resuspended in 15 volumes of 50 mM ice-cold Tris-HCl, homegenized and centrifuged again in the same way. The final pellet is resuspended in an appropriate volume of 50 mM Tris-HCl, dispensed into aliquots and stored at −80° C. until use.

Cerebral cortical tissues are removed from male Sprague-Dawley rats, weighed and placed in 10 volumes of 50 mM ice-cold HEPES (pH 7.5). This is homogenized in a Polytron homogenizer (30 sec at full speed) and subsequently centrifuged at 21,000 g and 4° C. for 12 min. The resulting pellet is resuspended in 50 mM ice-cold HEPES, homegenized and centrifuged again in the same way. The final pellet is resuspended in an appropriate volume of 50 mM HEPES, dispensed into aliquots and stored at −80° C. until use. The protein concentrations of homogenates are determined by Bradford method with BSA as a standard.

Binding Assays

Affinity of compounds for 5-HT4 and 5-HT3 receptors are assessed with using radiolabeled specific ligands, GR 113808 ({1-[2-(methylsulfonyl)ethyl]-4-piperidinyl}[methyl-$^3$H]-1H-indole-3-carboxylate) and BRL 43694 (1-Methyl-N-(9-[methyl-$^3$H]-9-azabicyclo[3.3.1]non-3-yl)-1H-indazole-3-caboxamide). Ten concentrations of compounds are incubated with 25–100 pM of [3H]-GR 113808 (Amersham) and 0.6–1 mg protein of pig or bovine striatal membranes suspended in a final volume of 0.8–1 ml of 50 mM HEPES (pH 7.5). Nonspecific binding is determined with 10–50 $\mu$M 5-HT. The binding of 0.3 nM [3H]-BRL 43694 (NEN) is measured using 400 $\mu$g protein of rat cortical membranes suspended in a final volume of 500 $\mu$l of 50 mM HEPES (pH 7.5). Nonspecific binding is determined with 10 $\mu$M 5-HT.

The plates are incubated at room temperature on a plate shaker for 30 min. The assays are stopped by rapid filtration using a Brandell cell harvester through Wallac-B filters pre-soaked in 0.2% poly(ethylenimine) at 4° C. for 60–90 min. The filters are washed three times with 1 ml of ice-cold 50 mM HEPES, and are dried in a microwave. They are bagged and heated with meltilex scintillant (Wallac) or soaked in BetaplateScint (Wallac). Receptor-bound radioactivity is quantified using Big-spot counter or Betaplate counter (Wallac).

All compounds prepared in the working examples as described below were tested by this method, and showed an $IC_{50}$ values of 1 nM to 1000 nM with respect to inhibition of binding at the 5-$HT_4$ receptor.

Functional Assay:

The presence of 5-$HT_4$ receptors in the rat oesophagus and the ability to demonstrate partial agonism in the TMM preparation are reported in the literature (See G. S. Baxter et al. Naunyn-Schmiedeberg's Arch Pharmacol (1991) 343: 439–446; M. Yukiko et al. JPET (1997) 283: 1000–1008; and J. J. Reeves et al. Br. J Pharmacol. (1991) 103: 1067–1072). More specifically, partial agonist activity can be measured according to the following procedures.

Male CD rats (supplier=Charles River) weighing 250–350 g are stunned and then killed by cervical dislocation. The oesophagus is dissected from immediately proximal to the stomach (including piece of stomach to mark distal end) up to the level of the trachea and then placed in fresh Krebs' solution.

The outer skeletal muscle layer is removed in one go by peeling it away from the underlying smooth muscle layer using forceps (stomach to tracheal direction). The remaining inner tube of smooth muscle is known as the TMM. This is trimmed to 2 cm from the original 'stomach-end' and the rest discarded.

The TMMs are mounted as whole 'open' tubes in longitudinal orientation in 5 ml organ baths filled with warm (32° C.) aerated Krebs. Tissues are placed under an initial tension of 750 mg and allowed to equilibrate for 60 minutes. The tissues are re-tensioned twice at 15 minute intervals during the equilibration period. The pump flow rate is set to 2 ml/min during this time.

Following equilibration, the pump is switched off. The tissues are exposed to 1 $\mu$M carbachol and will contract and reach a steady contractile plateau within 15 minutes. Tissues are then subject to 1 $\mu$M 5-HT (this is to prime the tissues). The tissues will relax in response to 5-HT fairly rapidly—within 1 minute. As soon as maximal relaxation has occurred and a measurement taken, the tissues are washed at maximum rate (66 ml/min) for at least 1 minute and until the original baseline (pre-carbachol and 5-HT) has returned (usually, the baseline will drop below the original one following initial equilibration). The pump flow rate is reduced to 2 ml/min and the tissues left for 60 minutes.

A cumulative concentration-effect-curve (CEC) to 5-HT is constructed across the range $1e^{-10}$ to $1 e^{-6}$M, in half-log unit increments (5-HT curve 1 for data analysis). Contact time between doses is 3 minutes or until plateau established. Tissues will respond quicker as concentration of 5-HT in the bath increases. At the end of the curve, the tissues are washed (at maximum rate) as soon as possible to avoid desensitisation of receptors. Pump rate is reduced to 2 ml/min and the tissues left for 60 minutes.

A second CEC is carried out—either to 5-HT (for time control tissues), another 5-$HT_4$ agonist (standard) or a test compound (curve 2 for data analysis). Contact time varies for other 5-$HT_4$ agonists and test compounds and is tailored according to the tissues' individual responses to each particular agent. In tissues exposed to a test compound, a high concentration (1 $\mu$M) of a 5-$HT_4$ antagonist (SB 203,186: 1H-Indole-3-carboxylic acid, 2-(1-piperidinyl)ethyl ester) is added to the bath following the last concentration of test compound. This is to see if any agonist-induced relaxation (if present) can be reversed. SB 203,186 reverses 5-HT induced relaxation, restoring the tissue's original degree of carbachol-induced tone.

Agonist activity of test compounds is confirmed by pre-incubating tissues with 100 nM standard 5$HT_4$ antagonist such as SB 203,186. SB 203,186 is added to the bath 5 minutes before the addition of carbachol prior to curve 2. Tissues must be 'paired' for data analysis i.e. the test compound in the absence of SB 203,186 in one tissue is compared with the test compound in the presence of SB 203,186 in a separate tissue. It is not possible to carry out a curve 3 i.e. 5-HT curve 1, followed by the test compound curve 2 (−SB 203,186), followed by the test compound curve 3 (+SB 203,186).

Agonist-Induced cAMP Elevation in Human 5-$HT_{4(d)}$ Transfected HEK293 Cells

Human 5-$HT_{4(d)}$ transfected HEK293 cells were established in-house. The cells were grown at 37° C. and 5% $CO_2$ in DMEM supplemented with 10% FCS, 20 mM HEPES (pH 7.4), 200 $\mu$g/ml hygromycin B (Gibco), 100 units/ml penicillin and 100 $\mu$g/ml streptomycin.

The cells were grown to 60–80% confluence. On the previous day before treatment with compounds dialyzed FCS (Gibco) was substituted for normal and the cells were incubated overnight.

Compounds were prepared in 96-well plates (12.5 $\mu$l/well). The cells were harvested with PBS/1 mM EDTA, centrifuged and washed with PBS. At the beginning of the assay, cell pellet was resuspended in DMEM supplemented with 20 mM HEPES, 10 $\mu$M pargyline (Sigma) and 1 mM 3-isobutyl-1-methylxanthine (Sigma) at the concentration of $1.6 \times 10^5$ cells/ml and left for 15 minutes at room temperature. The reaction was initiated by addition of the cells into plates (12.5 $\mu$l/well). After incubation for 15 minutes at room temperature, 1% Triton X-100 was added to stop the reaction (25 $\mu$l/well) and the plates were left for 30 minutes at room temperature. Homogenous time-resolved fluorescence-based cAMP (Schering) detection was made according to the manufacturer's instruction. ARVOsx multilabel counter (Wallac) was used to measure HTRF (excitation 320 nm, emission 665 nm/620 nm, delay time 50 $\mu$s, window time 400 $\mu$s).

Data was analyzed based on the ratio of fluorescence intensity of each well at 620 nm and 665 nm followed by cAMP quantification using cAMP standard curve. Enhancement of cAMP production elicited by each compound was normalized to the amount of cAMP produced by 1000 nM serotonin (Sigma).

According to the procedures as shown the above, the compounds prepared in Examples 1 to 110 were identified as 5$HT_4$ agonists.

Method of Gastric Emptying Model in Rats:

The effects of compounds on gastric emptying in rats were examined by the modified method of D. A. Droppleman et al. (J. Pharmacol. Methods 4, 227–230 (1980)). The test meal, non-fat caloric meal, was prepared according to the method of S. Ueki et al Arzneim.-Forsch./Drug Res. 49 (II), 618–625 (1999)). IGS-SD rats (Male, 7w, 230–270 g) were purchased from Charles River Japan (Atsugi). These rats were used in the experiments after one week acclimatization. In the experiments, rats were fasted 15 hrs before the experiments but allowed free access to water. Forty-five minutes prior to the start of the experiment, water was removed from the cage to prevent rats from taking water. Five minutes before the test meal administration, test compounds, cisapride or vehicle were dosed via an appropriate route to rats (n=8–10) in a volume of 0.1 ml per 100 g body weight. Cisapride (3 mg/kg) was used as a positive control for the experiment. Rats were given 3 ml of the test meal by gavage and were returned to the cages. Thirty minutes after the meal administration, rats were culled by $CO_2$ exposure.

Following a midline laparotomy, the stomach is ligated at the lower esophageal sphincter (LES) and pylorus. Then the stomach was removed and weighed (A). After the stomach was opened and rinsed with 0.9% saline, it was blotted the face with the tissue to remove any excess liquid and weighed again (B). After avoiding the rats that had eaten feces or given artificial miss, gastric emptying rate for individual animals was calculated by the formula:

$$GE \text{ rate } (\%) = (A-B)/\text{weight of the test meal.}$$

Gastric Motility in Conscious Dogs:

The surgical operation in dogs was performed by the modified method of Z. Itoh et al. (Gastroenterol. Jpn., 12, 275–283 (1977)). The effects of test compounds on gastric motility in dogs were examined by the modified method of N. Toshida et al. (J. Pharmacol. Exp/Ther., 257, 781–787 (1991)).

An evaluation in the fasted state: Animals were chronically implanted with a strain gauge force transducer on the gastric body, and fasted overnight prior to the experiment. The gastric motility was continuously recorded by a telemetry system for 8 h after administration of the compound. To quantitate the change in gastrointestinal motility, the motor index was determined as the area under the contraction curves during each 2 h period divided by the peak height of interdigestive migrating contraction.

An evaluation in the postprandial state: Animals were chronically implanted with a strain gauge force transducer on the gastric body, and fasted overnight prior to the experiment. Postprandial motility was induced by feeding with solid meal (100 grams), and the compound was administered 2 h later. The gastric motility was continuously recorded by a telemetry system for 8 h after administration of the compound. The motor index was determined to quantitate the change in gastrointestinal motility as the area under the contraction curves during each 1 h period divided by the area under the contraction curves for 1 h before the compound administration.

The oxo or oxy-pyridine compounds of formula (I) and (II) of this invention can be administered via either the oral, parenteral or topical routes to mammals. In general, these compounds are most desirably administered to humans in doses ranging from 0.3 mg to 750 mg per day, preferably from 10 mg to 500 mg per day, although variations will necessarily occur depending upon the weight and condition of the subject being treated, the disease state being treated and the particular route of administration chosen. However, for example, a dosage level that is in the range of from 0.06 mg to 2 mg per kg of body weight per day is most desirably employed for treatment of inflammation.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral-pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath temperature of up to 60° C.; reactions were monitored by thin layer chromatography (tlc) and reaction times are given for illustration only; melting points (m.p.) given are uncorrected (polymorphism may result in different melting points); the structure and purity of all isolated compounds were assured by at least one of the following techniques: tlc (Merck silica gel 60 $F_{254}$ precoated TLC plates or Merck $NH_2F_{254s}$ precoated HPTLC plates), mass spectrometry, nuclear magnetic resonance (NMR), infrared red absorption spectra (IR) or microanalysis. Yields are given for illustrative purposes only. Flash column chromatography was carried out using Merck silica gel 60 (230–400 mesh ASTM) or Fuji Silysia Chromatorex® DU3050 (Amino Type, 30–50 $\mu$m). Low-resolution mass spectral data (EI) were obtained on a Automass 120 (JEOL) mass spectrometer. Low-resolution mass spectral data (ESI) were obtained on a Quattro II (Micromass) mass spectrometer. NMR data was determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br.=broad, etc. IR spectra were measured by a Shimazu infrared spectrometer (IR-470). Optical rotations were measured using a JASCO DIP-370 Digital Polarimeter (Japan Spectroscopic CO, Ltd.). Chemical symbols have their usual meanings; b.p. (boiling point), m.p. (melting point), 1 (liter(s)), ml (milliliter(s)), g (gram(s)), mg(milligram(s)), mol (moles), mmol (millimoles), eq. (equivalent(s)).

Example 1

6-Amino-5-chloro-N-[(1-ethyl-4-piperidinyl)methyl]-2-oxo-1,2-dihydro-3-pyridinecarboxamide Step 1. 1,1-Dimethylethyl 4-[({[6-amino-5-chloro-2-(methyloxy)-3-pyridinyl] carbonyl}amino)methyl]-1-piperidinecarboxylate A mixture of 6-amino-5-chloro-2-(methyloxy)-3-pyridinecarboxylic acid (Y. Hirokawa et al., *Bioorg. Med. Chem. Lett.*, 1998, 12, 1551–1554, 500 mg, 2.47 mmol) and 1,1'-carbonyldiimidazole (440 mg, 2.71 mmol) in N,N-dimethylformamide (15 ml) was stirred at room temperature for 45 min. A solution of 1,1-dimethylethyl 4-(aminomethyl)-1-piperidinecarboxylate (529 mg, 2.47 mmol) in N,N-dimethylformamide (5 ml) was added and the resulting mixture was stirred at room temperature for 5 h. The mixture was poured into water (200 ml) and extracted with ethyl acetate/toluene (2:1, 200 ml×3). The combined organic layer was washed with water, dried over magnesium sulfate, and concentrated in vacuo. The obtained residue was chromatographed on a column of silica gel eluting with methanol/dichloromethane (1:25) to give 703 mg (71%) of the title compound as a pale yellow amorphous solid.

IR (KBr) ν: 3412, 3331, 3206, 2976, 2930, 2864, 1686, 1622, 1589, 1541, 1456, 1393, 1366, 1331, 1261, 1225, 1171, 1146, 1088, 1038, 993, 964, 941, 781, 710 cm$^{-1}$. $^1$H-NMR (CDCl$_3$) δ: 8.30 (1 H, s), 7.73 (1 H, br), 5.06 (2 H, br s), 4.19–4.05 (2 H, m), 3.99 (3 H, s), 3.37–3.27 (2 H, m), 2.69 (2 H, t, J=13.5 Hz), 1.80–1.65 (3 H, m), 1.29–1.10(2 H, m). Anal. Calcd. for C$_{18}$H$_{27}$ClN$_4$O$_4$: C, 54.20; H, 6.82; N, 14.05. Found: C, 53.81; H, 6.79; N, 13.98.

Step 2. 6-Amino-5-chloro-2-oxo-N-(4-piperidinylmethyl)-1,2-dihydro-3-pyridinecarboxamide dihydrochloride A suspension of 1,1-dimethylethyl 4-[({[6-amino-5-chloro-2-(methyloxy)-3-pyridinyl] carbonyl}amino)methyl]-1-piperidinecarboxylate (step 1, 350 mg, 0.88 mmol) in aqueous 2 N hydrochloric acid (20 ml) was refluxed with stirring for 12 h. After cooling to room temperature, the solvent was removed in vacuo. The residue was crystallized from methanol/diisopropyl ether to give 275 mg (88%) of the title compound as a gray powder.

MS (ESI) m/z: 285 (M+H$^+$), 283 (M−H$^-$). m.p.: 275° C. (decomposition). IR (KBr) ν: 3290, 2963, 2829, 2361, 2341, 1645, 1591, 1558, 1456, 1366, 1300, 1250, 1163, 1080 cm$^{-1}$. $^1$H-NMR (DMSO-d$_6$) δ: 9.32 (1 H, br), 8.71 (1 H, br), 8.34 (1 H, br), 7.98 ( 1 H, s), 7.14 (2 H, br s), 3.30–3.15 (4 H, m), 2.90–2.75 (2 H, m), 1.82–1.70 (3 H, m), 1.40–1.25 (2 H, m). Anal. Calcd. for C$_{12}$H$_{17}$ClN$_4$O$_2$·2HCl·0.8H$_2$O: C, 38.74; H, 5.58; N, 15.06. Found: C, 38.82; H, 5.75; N, 14.90.

Step 3. 6-Amino-5-chloro-N-[(1-ethyl-4-piperidinyl)methyl]-2-oxo-1,2-dihydro-3-pyridinecarboxamide A mixture of 6-amino-5-chloro-2-oxo-N-(4-piperidinylmethyl)-1,2-dihydro-3-pyridinecarboxamide dihydrochloride (step 2, 100 mg, 0.28 mmol), iodoethane (49 mg, 0.31 mmol) and potassium carbonate (172 mg, 1.25 mmol) in N,N-dimethylformamide (6 ml) was stirred at 60° C. for 15 h. After cooling to room temperature, the solvent was removed in vacuo. The residue was suspended in tetrahydrofuran (50 ml), and the solution was filtered through a pad of Celite. The filtrate was concentrated in vacuo, and the obtained residue was chromatographed on a column of aminopropyl silica gel eluting with methanol/dichloromethane (1:2.5) to give 43 mg (49%) of the title compound as a white solid.

MS (ESI) m/z: 313 (M+H$^+$), 311 (M−H$^-$). m.p.: 136–140° C. IR (KBr) ν: 3290, 3176, 2924, 1661, 1616, 1558, 1539, 1427, 1350, 1273, 1244, 1202, 1146, 953, 802, 791, 762, 700, 644 cm$^{-1}$. $^1$H-NMR (DMSO-d$_6$) δ: 9.43 (1 H, br), 7.95 (1 H, s), 7.16 (1 H, br), 3.13 ( 2 H, t, J=6.3 Hz), 2.90 (2 H, d, J=9.0 Hz), 2.40–2.29 (2 H, m), 1.97–1.82 (2 H, m), 1.62 (2 H, d, J=13.2 Hz), 1.50–1.35 (1 H, br), 1.24–1.09 (2 H, m), 0.99 (3 H, t, J=6.9 Hz). Anal. Calcd. for C$_{14}$H$_{21}$ClN$_4$O$_2$·0.7H$_2$O: C, 51.67; H, 6.94; N, 17.22. Found: C, 51.56; H, 7.18; N, 17.01.

Example 2

6-Amino-5-chloro-N-({1-[3-(methyloxy)propyl]-4-piperidinyl}-methyl)-2-oxo-1,2-dihydro-3-pyridinecarboxamide Step 1. 1-[3-(Methyloxy)propyl]-4-piperidinecarboxamide A mixture of isonipecotamide (10.6 g, 82.3 mmol), 1-bromo-3-(methyloxy)propane (C. A. Grob and A. Waldner, *Helv. Chim. Acta*, 1980, 63, 2152–2158., 12.6 g, 82.3 mmol), and potassium carbonate (22.8 g, 165 mmol) in ethanol (60 ml) was refluxed with stirring for 23 h. After cooling to room temperature, the solvent was removed in vacuo. The residue was dissolved in water (500 ml), and the aqueous layer was extracted with dichloromethane (300 ml×13). The combined organic layer was dried over magnesium sulfate, and concentrated in vacuo to give 8.04 g (49%) of the title compound as a white solid.

MS (ESI) m/z: 201 (M+H$^+$) $^1$H-NMR (CDCl$_3$) δ: 5.70 (2 H, br), 3.42 (2 H, t, J=6.6 Hz), 3.33 (3 H, s), 2.97 (2 H, br d, J=11.7 Hz), 2.45–2.37 (2H, m), 2.21–2.10 (1 H, m), 2.04–1.84 (4 H, m), 1.82–1.70 (4 H, m).

Step 2. {1-[3-(Methyloxy)propyl]-4-piperidinyl}methylamine

To a suspension of lithium aluminum hydride (3.32 g, 70.0 mmol) in tetrahydrofuran (200 ml) was added dropwise a solution of 1-[3-(methyloxy)propyl]-4-piperidinecarboxamide (step 1, 7.00 g, 35.0 mmol) in tetrahydrofuran (50 ml) at 0° C. over 15 minutes. The mixture was stirred at 0° C. for 30 min and at 40° C. for 1.5 h. After cooling to 0° C., water (3.3 ml), 15% aqueous sodium hydroxide (3.3 ml) and water (10 ml) were carefully added dropwise. The resulting mixture was filtered through a pad of Celite and the filtrate was concentrated in vacuo to give 6.31 g (97%) of the title compound as a pale yellow oil.

$^1$H-NMR (CDCl$_3$) δ: 3.41 (3 H, t, J=6.4 Hz), 3.33 (3 H, s), 2.94 (2 H, d, J=11.7 Hz), 2.57 (2 H, d, J=5.6 Hz), 2.39 (2 H, dd, J7.4, 9.7 Hz), 1.97–1.67 (6 H, m), 1.32–1.18 (3 H, m).

Step 3. 6-Amino-5-chloro-2-(methyloxy)-N-({1-[3-(methyloxy)propyl]-4-piperidinyl}methyl)-3-pyridinecarboxamide The title compound was prepared according to the procedure of step 1 in the example 1 using {1-[3-(methyloxy)

propyl]-4-piperidinyl}methylamine (step 2) instead of 1,1-dimethylethyl 4-(aminomethyl)-1-piperidinecarboxylate.

MS (ESI) m/z: 371 (M+H⁺) m.p.: 103° C. IR (KBr) v: 3395, 3354, 3121, 2932, 2810, 2359, 2341, 1630, 1587, 1541, 1481, 1454, 1393, 1333, 1302, 1265, 1219, 1148, 1119, 1042, 993, 972, 932, 784 cm⁻¹. ¹H-NMR (DMSO-d₆) δ: 7.91 (1 H, s), 7.85 (1 H, t, J=6.0 Hz), 6.90 (2 H, br), 3.90 (3 H, s), 3.31 (2 H, t, J=6.3 Hz), 3.20 (3 H, s), 3.14 (2 H, t, J6.6 Hz), 2.81 (2 H, br d, J=11.1 Hz), 2.26 (2 H, t, J=6.9 Hz), 1.79 (2 H, t, J=10.2 Hz), 1.68–1.39 (5 H, m), 1.23–1.05 (2 H, m). Anal. Calcd. for C₁₇H₂₇ClN₄O₃·0.1H₂O: C, 54.79; H, 7.36; N, 15.03. Found: C, 54.58; H, 7.35; N, 14.94.

Step 4. 6-Amino-5-chloro-N-({1-[3-(methyloxy)propyl]-4-piperidinyl}methyl)-2-oxo-1,2-dihydro-3-pyridinecarboxamide A solution of 6-amino-5-chloro-2-(methyloxy)-N-({1-[3-(methyloxy)propyl]-4-piperidinyl}methyl)-3-pyridinecarboxamide (step 3, 160 g, 0.43 mmol) in concentrated hydrochloric acid (2.5 ml) and 10% methanolic hydrochloric acid (10 ml) was stirred at 80° C. for 7 h. After cooling to room temperature, the solvent was removed in vacuo. The residue was suspended in diisopropyl ether and the precipitate was collected by filtration to give 85 mg (46%) of the title compound as a white amorphous solid.

MS (ESI) m/z: 357 (M+H⁺), 355 (M−H⁻). IR (KBr) v: 3410, 2943, 2725, 1361, 2341, 1647, 1560, 1481, 1364, 1298, 1248, 1196, 1165, 1115, 1082, 951, 760 cm⁻¹. ¹H-NMR (DMSO-d₆) δ: 9.73 (1 H, br), 9.34 (1 H, br), 7.98 (1 H, s), 7.19 (2 H, br), 3.47 (2 H, d, J=11.0 Hz), 3.70 (2 H, t, J=6.0 Hz), 3.25–3.14 (5 H, m), 3.07–2.98 (2 H, m), 2.92–2.78 (2 H, m), 1.96–1.85 (2 H, m), 1.84–1.65 (3 H, m), 1.54–1.38 (2 H, m). Anal. Calcd. for C₁₆H₂₅ClN₄O₃·2HCl·0.5H₂O: C, 43.80; H, 6.43; N, 12.77. Found: C, 43.53; H, 6.58; N, 12.59.

Example 3

6-Amino-N-[(1-butyl-4-piperidinyl)methyl]-5-chloro-2-oxo-1,2-dihydro-3-pyridinecarboxamide di-hydrochloride Step 1. 6-Amino-N-[(1-butyl-4-piperidinyl)methyl]-5-chloro-2-(methyloxy)-3-pyridinecarboxamide The title compound was prepared according to the procedure of step 1 in example 1 using (1-butyl-4-piperidinyl)methylamine (K. Ito et al., *Eur. J Med. Chem. Chim. Ther.,* 1999, 34, 977) instead of 1,1-dimethylethyl 4-(aminomethyl)-1-piperidinecarboxylate.

MS (EI) m/z: 354 (M⁺) ¹H-NMR (DMSO-d₆) δ: 7.91 (1 H, s), 7.85 (1 H, t, J=5.9 Hz), 6.90 (1 H, s), 3.91 (3 H, s), 3.14 (2 H, t, J=6.2 Hz), 2.95–2.87 (2 H, m), 2.21 (2 H, t, J=7.0 Hz), 1.85–1.72 (2 H, m), 1.65–1.09 (9 H, m), 0.87 (3 H, t, J=7.1 Hz).

Step 2. 6-Amino-N-[(1-butyl-4-piperidinyl)methyl]-5-chloro-2-oxo-1,2-dihydro-3-pyridinecarboxamide dihydrochloride The title compound was prepared according to the procedure of step 4 in example 2 using 6-amino-N-[(1-butyl-4-piperidinyl)methyl]-5-chloro-2-(methyloxy)-3-pyridinecarboxamide (step 1) instead of 6-amino-5-chloro-2-(methyloxy)-N-({1-[3-(methyloxyropyl]-4-piperidinyl}methyl)-3-pyridinecarboxamide.

MS (EI) m/z: 340 (M+). IR (KBr) v: 2950, 1650, 1558, 1470, 1355, 1300, 1249 cm⁻¹. ¹H-NMR (DMSO-d₆) δ: 9.60 (1 H, br s), 7.90 (1 H, s), 7.36 (2 H, br s), 3.11 (1 H, t, J=5.9 Hz), 2.83 (2 H, m), 2.20 (1 H, t, J=7.3 Hz), 1.89–1.73 (2 H, m), 1.68–1.55 (2 H, m), 1.50–1.10 (7 H, m), 0.86 (3 H, t, J=7.3 Hz). Anal. Calcd. for C₁₆H₂₅ClN₄O₂·2HCl: C, 46.44; H, 6.58; N, 13.54. Found: C, 47.01; H, 6.86; N, 12.97.

Example 4

6-Amino-N-[(1-butyl-4-piperidinyl)methyl]-5-chloro-1-methyl-2-oxo-1,2-dihydro-3-pyridinecarboxamide Step 1. 6-Amino-N-[(1-butyl-4-piperidinyl)methyl]-5-chloro-1-methyl-2-oxo-1,2-dihydro-3-pyridinecarboxamide To a solution of 6-amino-N-[(1-butyl-4-piperidinyl)methyl]-5-chloro-2-oxo-1,2-dihydro-3-pyridinecarboxamide dihydrochloride (step 2 in example 3, 80 mg, 0.19 mmol) in N,N-dimethylformamide (3 ml), sodium hydride (60% dispersion in mineral oil, 39 mg, 0.97 mmol) was added at 0° C. and the mixture was stirred for 15 min at room temperature. The mixture was cooled to 0° C. and iodomethane (1.0 M in N,N-dimethylformamide, 0.19 ml, 0.19 mmol) was added. After stirring for 18 h at room temperature, the mixture was poured into water, extracted with ethyl acetate (50 ml×2), washed with water (50 ml) and brine (50 ml) and dried over magnesium sulfate. Removal of solvent gave pale yellow oil, which was chromatographed on a column of silica gel eluting with 25% ammonium hydroxide/methanol/dichloromethane (0.2:1:12) to give 4 mg (6%) of the title compound as a white solid.

MS (EI) m/z: 354 (M⁺). IR (KBr) v: 3184, 2927, 1653, 1560, 1508, 1363, 1213, 788 cm⁻¹. ¹H-NMR (CDCl₃) δ: 9.54 (1 H, br s), 8.40 (1 H, s), 5.45 (2 H, br s), 3.59 (3 H, s), 3.32 (2 H, t, J=6.4 Hz), 3.02–2.93 (2 H, m), 2.40–2.20 (2 H, m), 2.10–1.20 (11 H, m), 0.91 (3 H, t, J=7.1 Hz)

Example 5

6-Amino-5-chloro-N-{[1-(3-methylbutyl)-4-piperidinyl]methyl}-2-oxo-1,2-dihydro-3-pyridinecarboxamide Step 1. 6-Amino-5-chloro-N-{[1-(3-methylbutyl)-4-piperidinyl]methyl}-2-oxo-1,2-dihydro-3-pyridinecarboxamide The title compound was prepared according to the procedure of step 3 in the example 1 using 1-iodo-3-methylbutane instead of iodoethane.

MS (ESI) m/z: 355 (M+H⁺), 353 (M−H⁻). m.p.: 131–135° C. IR (KBr) v: 3298, 3186, 2955, 2928, 2870, 2363, 1661, 1618, 1560, 1541, 1429, 1352, 1275, 1244, 1202, 1146, 1103, 945, 802, 790, 764, 702, 644 cm⁻¹. ¹H-NMR (DMSO-d₆) δ: 9.40 (1 H, br), 7.95 (1 H, s), 7.13 (2 H, br), 3.13 (2 H, t, J=6.0 Hz), 2.87 (2 H, d, J=10.3 Hz), 2.33–2.23 (2 H, m), 1.95–1.82 (2 H, m), 1.66–1.05 (8 H, m), 0.89 (6 H, d, J=6.4 Hz). Anal. Calcd. for C₁₇H₂₇ClN₄O₂·0.2H₂O: C, 56.96; H, 7.70; N, 15.63. Found: C, 57.10; H, 8.09; N, 15.71.

Example 6

6-Amino-5-chloro-N-{[1-(2-methylpropyl)-4-piperidinyl]methyl}-2-oxo-1,2-dihydro-3-pyridinecarboxamide Step 1. 6-Amino-5-chloro-N-{[1-(2-methylpropyl)-4-piperidinyl]methyl}-2-oxo-1,2-dihydro-3-pyridinecarboxamide The title compound was prepared according to the procedure of step 3 in the example 1 using 1-iodo-2-methylpropane instead of iodoethane.

MS (ESI) m/z: 341 (M+H⁺), 339 (M−H⁻). m.p.: 128–133° C. IR (KBr) ν: 3306, 3190, 2926, 2870, 2737, 1661, 1618, 1560, 1541, 1485, 1429, 1352, 1273, 1244, 1202, 1146, 1101, 961, 802, 791, 702, 644 cm⁻¹. ¹H-NMR (DMSO-d₆) δ: 9.34 (1 H, br), 7.97 (1 H, s), 7.05 (2 H, br), 3.13 ( 3 H, t, J=6.4 Hz), 2.81 (2 H, d, J=11.0 Hz), 2.01 (2 H, d, J=7.1 Hz), 1.90–1.70 (3 H, m), 1.60 (2 H, d, J=11.9 Hz), 1.45–1.35 (1 H, m), 1.28–1.05 (2 H, m), 0.83 (6 H, d, J= 6.4 Hz). Anal. Calcd. for C₁₆H₂₅ClN₄O₂·0.9H₂O: C, 53.82; H, 7.57; N, 15.69. Found: C, 54.04; H, 7.47; N, 15.68.

Example 7

Ethyl [4-({[(6-amino-5-chloro-2-oxo-1,2-dihydro-3-pyridinyl)carbonyl] amino}methyl)-1-piperidinyl] acetate Step 1. Ethyl [4-({[(6-amino-5-chloro-2-oxo-1,2-dihydro-3-pyridinyl)carbonyl]-amino}methyl)-1-piperidinyl]acetate The title compound was prepared according to the procedure of step 3 in the example 1 using ethyl bromoacetate instead of iodoethane MS (ESI) m/z: 371 (M+H⁺), 369 (M−H⁻). m.p.: 162–164° C. IR (KBr) ν: 3487, 3315, 3188, 2924, 2363, 1749, 1665, 1630, 1558, 1489, 1377, 1346, 1281, 1246, 1192, 1034, 1034, 972, 851, 791, 704, 638, 611 cm⁻¹. ¹H-NMR (DMSO-d₆) δ: 9.39 (1 H, br), 7.96 (1 H, s), 7.12 (2 H, br), 4.08 ( 2 H, q, J=7.0 Hz), 3.17–3.10 (4 H, m), 2.80 (2 H, d, J=11.1 Hz), 2.10 (2 H, t, J= 11.1 Hz), 1.58 (2 H, d, J=12.2 Hz), 1.48–1.30 (1 H, m), 1.27–1.15 (2 H, m), 1.18 (3 H, t, J= 7.0 Hz). Anal. Calcd. for C₁₆H₂₃ClN₄O₄·0.2H₂O: C, 51.32; H, 6.30; N, 14.96. Found: C, 51.32; H, 6.22; N, 15.00.

Example 8

1,1-Dimethylethyl [4-({[(6-amino-5-chloro-2-oxo-1,2-dihydro-3-pyridinyl)carbonyl] amino}methyl)-1-piperidinyl]acetate Step 1. 1,1-Dimethylethyl [4-({[(6-amino-5-chloro-2-oxo-1,2-dihydro-3-pyridinyl)carbonyl] amino}methyl)-1-piperidinyl]acetate The title compound was prepared according to the procedure of step 3 in the example 1 using tert-butyl bromoacetate instead of iodoethane.

MS (ESI) m/z: 399 (M+H⁺), 397 (M−H⁻). m.p.: 200–203° C. IR (KBr) ν: 3182, 2930, 1742, 1665, 1630, 1556, 1485, 1454, 1367, 1350, 1246, 1155, 1076, 791, 702 cm⁻¹. ¹H-NMR (DMSO-d₆) δ: 9.27 (1 H, br), 7.98 (1 H, s), 6.97 (2 H, br s), 3.13 ( 2 H, t, J=6.3 Hz), 3.05 (2 H, s), 2.80 (2 H, d, J=11.4 Hz), 2.10 (2 H, t, J=10.5 Hz), 1.57 (2 H, d, J=12.6 Hz), 1.40 (9 H, s), 1.45–1.30 (1 H, m), 1.23–1.09 (2 H, m). Anal. Calcd. for C₁₈H₂₇ClN₄O₄: C, 54.20; H, 6.82; N, 14.05. Found: C, 54.13; H, 6.71; N, 13.80.

Example 9

1-[6-Amino-5-chloro-2-(methoxy)-3-pyridinyl]-3-(4-piperidinyl)-1-propanone hydrochloride Step 1. 1,1-Dimethylethyl 4-(3-{6-[(2,2-dimethylpropanoyl)amino]-2-fluoro-3-pyridinyl}-3-hydroxypropyl)-1-piperidinecarboxylate To a solution of N-(6-fluoro-2-pyridinyl)-2,2-dimethylpropanamide (Turner, James A., *J. Org. Chem.*, 1983, 48, 3401–3408, 1.15 g, 5.87 mmol) in tetrahydrofuran (15 ml) was added dropwise a solution of n-butyllitium (8.1 ml, 12.9 mmol) at −78° C. over 10 min., and the mixture was stirred at 0° C. for 1 h. After cooling to −78° C., a solution of 1,1-dimethylethyl 4-(3-oxopropyl)-1-piperidinecarboxylate (Keenan, Richard M. et. al, *J. Med. Chem.*, 1999, 42, 545–559, 1.70 g, 7.04 mmol) in tetrahydrofuran (5 ml) was added to the mixture. After stirring for 0.5 h, the mixture was allowed to warm up to room temperature and stirred for further 2 h. The mixture was quenched with water (20 ml) and extracted with ethyl acetate (100 ml). The organic layer was washed with brine (50 ml) and dried over magnesium sulfate. Removal of solvent gave brown oily residue, which was chromatographed on a column of silica gel eluting with ethyl acetate/hexane (2:1) to afford 0.86 g (34%) of the title compound as a pale yellow amorphous solid.

MS (EI) m/z: 437 (M⁺). ¹H-NMR (CDCl₃) δ: 8.12 (1 H, dd, J=1.6 and 8.4 Hz), 7.91 (1 H, d, J=9.7 Hz), 7.86 (1 H, br s), 4.99 (1 H, q, J=5.4 Hz), 4.06 (2 H, br d, J=13.3 Hz), 2.65 (2 H, br t, J=13.3 Hz), 1.44 (9 H, s), 1.31 (9 H, s), 1.05–1.92 (9 H m).

Step 2. 1,1-Dimethylethyl 4-(3-{6-[(2,2-dimethylpropanoyl) amino]-2-fluoro-3-pyridinyl}-3-oxopropyl)-1-piperidinecarboxylate To a solution of oxalyl chloride (0.11 ml, 1.25 mmol) in dichloromethane (10 ml) was added dropwise dimethylsulfoxide (0.18 ml, 2.51 mmol) at −78° C. After stirring for 10 min, a solution of 1,1-dimethylethyl 4-(3-{6-[(2,2-dimethylpropanoyl)amino]-2-fluoro-3-pyridinyl}-3-hydroxypropyl)-1-piperidinecarboxylate (step 1, 500 mg, 1.14 mmol) in dichloromethane (5 ml) was added to the mixture at −78° C. After 15 min, triethylamine (0.79 ml, 5.70 mmol) was added at the same temperature and the resulting mixture was allowed to warm up to room temperature and stirred for 18 h. The mixture was quenched with 1N aqueous hydrochloric acid (100 ml) and extracted with dichloromethane (150 ml). The organic layer was washed with water (50 ml) and dried over magnesium sulfate. Removal of solvent gave a pale yellow solid, which was chromatographed on a column of silica gel eluting with ethyl acetate/hexane (4:1 ) to afford 362 mg (73%) of the title compound as a white solid.

Rf: 0.6 (n-hexane/ethyl acetate=2:1) ¹H-NMR (CDCl₃) δ: 8.38 (1 H, t, J=8.6 Hz), 8.21 (1 H, dd, J=2.2 and 8.4 Hz), 8.04 (1 H, br s), 4.11 (1 H, br s), 2.98 (2 H, dt, J=2.9 and 7.3 Hz), 2.68 (1 H, br t, J= 12.5 Hz), 1.46 (9 H, s), 1.33 (9 H, s), 1.07–1.71 (9 H, m).

Step 3. 1,1-Dimethylethyl 4-{3-[6-amino-2-(methyloxy)-3-pyridinyl]-3-oxopropyl}-1-piperidinecarboxylate A mixture of 1,1-dimethylethyl 4-(3-{6-[(2,2-dimethylpropanoyl)amino]-2-fluoro-3-pyridinyl}-3-oxopropyl)-1-piperidinecarboxylate (step 2, 360 mg, 0.827 mmol) and potassium tert-butoxide (278 mg, 2.48 mmol) in methanol (8 ml) was refluxed for 1 h. After cooling to room temperature, the mixture was diluted with water (20 ml) and extracted with diethyl ether (100 ml×2). The combined organic layer was washed with water (50 ml) and brine (50 ml), and dried over magnesium sulfate. Removal of the solvent gave 300 mg (100%) of the title compound as a colorless gum.

MS (EI) m/z: 363 (M⁺). ¹H-NMR (CDCl₃) δ: 8.04 (1 H, d, J=8.4 Hz), 6.09 (1 H, d, J=8.4 Hz), 4.75 (2 H, br s), 4.08 (1 H, br s), 3.95 (3H, s), 2.94 (2 H, t, J=7.7 Hz), 2.68 (2 H, br t, J= 12.9 Hz), 1.57–1.71 (6 H, m), 1.45 (9 H, s), 1.04–1.19 (2 H, m).

Step 4. 1,1-Dimethylethyl 4-{3-[6-amino-5-chloro-2-(methyloxy)-3-pyridinyl]-3-oxopropyl}-1-piperidinecarboxylate A mixture of 1,1-dimethylethyl 4-{3-[6-amino-2-(methyloxy)-3-pyridinyl]-3-oxopropyl}-1-piperidinecarboxylate (step 3, 300 mg, 0.825 mmol) and N-chlorosuccinimide (115.7 mg, 0.866mmol) in N,N-dimethylformamide (5 ml) was stirred at 80° C. for 4 h. After cooling to room temperature, the mixture was diluted with diethylether (150 ml), washed with water (50 ml×2) and brine (150 ml), and dried over magnesium sulfate. Removal of solvent gave a brown oil, which was chromatographed on a column of silica gel eluting with ethyl acetate/hexane (2:1) to afford 182 mg (56%) of the title compound as a colorless oil.

MS (EI) m/z: 397 (M$^+$). $^1$H-NMR (CDCl$_3$) δ: 8.08 (1 H, s), 5.17 (2 H, br s), 4.09 (2 H, br s), 3.95 (3 H, s), 2.92 (2 H, t, J=7.2 Hz), 2.68 (2 H, br t, J=12.3 Hz), 1.57–1.70 (5 H, m), 1.45 (9 H, s), 1.04–1.18 (2 H, m).

Step 5. 1-[6-Amino-5-chloro-2-(methyloxy)-3-pyridinyl]-3-(4-piperidinyl)-1-propanone A mixture of 1,1-dimethylethyl 4-{3-[6-amino-5-chloro-2-(methyloxy)-3-pyridinyl]-3-oxopropyl}-1-piperidinecarboxylate (step 4, 180 mg, 0.452 mmol) in 10% methanolic hydrochloric acid (2 ml) was stirred at room temperature for 18 h. After concentrated in vacuo, the mixture was dissolved in ethyl acetate (50 ml), washed with 2N aqueous sodium hydroxide (3 ml) and brine (5 ml), and dried over potassium carbonate. Removal of solvent gave 117.1 mg (87%) of the title compound as a white solid.

MS (EI) m/z: 297 (M$^+$). $^1$H-NMR (CDCl$_3$) δ: 8.07 (1 H, s), 5.30 (2 H, br s), 3.94 (3 H, s), 3.06 (2 H, br d, J=11.9 Hz), 2.92 (2 H, t, J=7.5 Hz), 2.58 (2 H, dt, J=2.4 and 12.1 Hz), 1.70 (2 H, br d, J=12.5 Hz), 1.58 (2 H, q, J=7.9 Hz), 1.34–1.46 (1 H, m), 1.12 (2 H, dq, J= 4.0, 12.1 Hz).

Step 6. 1-(6-Amino-5-chloro-2-methoxy-3-pyridinyl)-3-(4-piperidinyl)-1-propanone hydrochloride A mixture of tert-butyl 4-{3-[6-amino-5-chloro-2-(methyloxy)-3-pyridinyl]-3-oxopropyl}-1-piperidinecarboxylate (step 5, 610 mg, 1.53 mmol) in 10% methanolic hydrochloric acid (6 ml) was stirred at room temperature for 18 h. The formed solid was collected by filtration, washed with methanol and dried to give 242.0 mg (47%) of the title compound as a white solid.

MS (EI) m/z: 297 (M$^+$). m.p.: 230.6° C. IR (KBr) v: 3398, 3298, 2953, 1661, 1616, 1580, 1551, 1462, 1400, 1194 (cm$^{-1}$). $^1$H-NMR (DMSO-d6) δ: 8.44 (2 H, br s), 7.86 (1 H, s), 7.23 (1 H, br s), 3.90 (3 H, s), 3.23 (2 H, br d, J=12.4 Hz), 2.76–2.87 (4 H, m), 1.79 (2 H, br d, J=12.2 Hz), 1.21–1.53 (5 H, m). Anal. Calcd. for C$_{14}$H$_{20}$N$_3$O$_2$·HCl·1.2H$_2$O: C, 47.25; H, 6.63; N, 11.81. Found: C, 47.01; H, 6.74; N, 11.84.

Example 10

1-[6-Amino-5-chloro-2-(methoxy)-3-pyridinyl]-3-(1-butyl-4-piperidinyl)-1-propanone Step 1. 1-[6-Amino-5-chloro-2-(methyloxy)-3-pyridinyl]-3-(1-butyl-4-piperidinyl)-1-propanone A mixture of 1-[6-amino-5-chloro-2-(methyloxy)-3-pyridinyl]-3-(4-piperidinyl)-1-propanone (step 5 in example 9, 110 mg, 0.369 mmol), 1-iodobutane (0.046 ml, 0.406 mmol) and potassium carbonate (102 mg, 0.738 mmol) in tetrahydrofuran (3 ml) was refluxed for 2 h. After cooling to room temperature, the mixture was diluted with ethyl acetate (50 ml), washed with water (5 ml) and brine (10 ml), and dried over potassium carbonate. Removal of solvent gave a pale yellow oil, which was crystallized from methanol to afford 92 mg (64%) of the title compound as a white crystal.

MS (EI) m/z: 353 (M$^+$). m.p.: 86–87° C. (recrystallized from methanol). IR (KBr) v: 2928, 1630, 1580, 1553, 1460, 1394, 1339, 1231, 1180 cm$^{-1}$. $^1$H-NMR (CDCl$_3$) δ: 8.07 (1 H, s), 5.24 (2 H, br s), 3.94 (3 H, s), 2.91 (4 H, t, J=7.7 Hz), 2.29 (2 H, t, J=7.6 Hz), 1.87 (2 H, t, J=10.9 Hz), 1.23–1.72 (11 H, m), 0.91 (3 H, t, J=7.3 Hz). Anal. Calcd. for C$_{18}$H$_{28}$ClN$_3$O$_2$·1MeOH·0.1H$_2$O: C, 59.01; H, 8.13; N, 10.87. Found: C, 58.61; H, 8.27; N, 11.03.

Example 11

6-Amino-3-[3-(1-butyl-4-piperidinyl)propanoyl]-5-chloro-2(1H)-pyridinone

Step 1. 6-Amino-3-[3-(1-butyl-4-piperidinyl)propanoyl]-5-chloro-2(1H)-pyridinone A mixture of 1-[6-amino-5-chloro-2-(methyloxy)-3-pyridinyl]-3-(1-butyl-4-piperidinyl)-1-propanone (step 1 in example 10, 50 mg, 0.129 mmol) in 10% methanolic hydrochloric acid (2 ml) was refluxed for 1 h. The mixture was added concentrated hydrochloric acid (0.6 ml) and the resulting mixture was refluxed for 6 h. After cooling to room temperature, the mixture was concentrated in vacuo. The residue was dissolved in a mixture of ethyl acetate (150 ml) and tetrahydrofuran (150 ml), washed with 2 N aqueous sodium hydroxide (10 ml), water (20 ml) and brine (20 ml), and dried over potassium carbonate. Removal of solvent gave a pale red solid, which was chromatographed on a column of silica gel eluting with 25% ammonium hydroxide/methanol/dichloromethane (0.2:1:10 ) to afford a pale yellow solid. The solid was washed with ethyl acetate to yield 5.5 mg (13%) of the title compound as a pale yellow solid.

Rf: 0.3 (25% ammonium hydroxide/methanol/dichloromethane=0.2:1:10) MS (ESI) m/z: 339 (M$^+$). $^1$H-NMR (DMSO-d$_6$) δ: 8.00 (1 H, s), 7.36 (2 H, br s), 2.81–2.91 (4 H, m), 1.08–2.23 (15 H, m), 0.87 (3 H, t, J=7.2Hz).

Example 12

1-(6-Amino-2-methoxy-3-pyridinyl)-3-(1-butyl-4-piperidinyl)-1-propanone

Step 1. 1-(6-Amino-2-methoxy-3-pyridinyl)-3-(4-piperidinyl)-1-propanone

The title compound was prepared according to the procedure of step 5 in the example 9 using tert-butyl 4-[3-(6-amino-2-methoxy-3-pyridinyl)-3-oxopropyl]-1-piperidinecarboxylate (step 3 in example 9), instead of tert-butyl 4-{3-[6-amino-5-chloro-2-(methyloxy)-3-pyridinyl]-3-oxopropyl}-1-piperidinecarboxylate.

MS (EI) m/z: 263 (M$^+$). $^1$H-NMR (CDCl$_3$) δ: 8.04 (1 H, d, J=8.3 Hz), 6.09 (1 H, d, J=8.3 Hz), 4.72 (2 H, br s), 3.95 (3 H, s), 3.06 (2 H, d, J=11.7 Hz), 2.93 (2 H, t, J=7.5 Hz), 2.58 (2 H, dt, J=2.6 and 12.1 Hz), 1.55–1.73 (5 H, m), 1.38–1.45 (1 H, m), 1.07–1.19 (2 H, m).

Step 2. 1-(6-Amino-2-methoxy-3-pyridinyl)-3-(1-butyl-4-piperidinyl)-1-propanone

A mixture of 1-(6-amino-2-methoxy-3-pyridinyl)-3-(4-piperidinyl)-1-propanone (step 1, 175 mg, 0.665 mmol), 1-iodobutane (0.083 ml, 0.732 mmol) and potassium carbonate (184 mg, 1.33 mmol) in tetrahydrofuran (5 ml) was refluxed for 6 h. After cooling to room temperature, the mixture was diluted with ethyl acetate (50 ml), washed with water (5 ml) and brine (10 ml) and dried over potassium carbonate. Removal of solvent gave the pale yellow oil, which was chromatographed on a column of silica gel eluting with 25% ammonium hydroxide/methanol/dichloromethane (0.2:1:10) to give pale yellow solid, which was washed with acetonitrile to afford 107.0 mg (50%) of the title compound as pale yellow solids.

MS (EI) m/z: 319 (M$^+$). m.p.: 85–89° C. IR (KBr) v: 3341, 3217, 2959, 2936, 1655, 1641, 1593, 1556, 1458, 1387, 1366, 1244, 1217, 1117 (cm$^{-1}$). $^1$H-NMR (CDCl$_3$) δ: 8.04 (1 H, d, J=8.4 Hz), 6.08 (1 H, d, J=8.4 Hz), 4.72 (2 H, br s), 3.95 (3 H, s), 2.92 (4 H, t, J=7.6 Hz), 2.29 (2 H, t, J=7.9 Hz), 1.24–1.92 (13 H, m), 0.91 (3 H, t, J=7.4 Hz). Anal. Calcd. for C$_{18}$H$_{29}$N$_3$O$_2$·1H$_2$O: C, 64.07; H, 9.26; N, 12.45. Found: C, 63.75; H, 8.97; N, 12.42.

Example 13

6-Amino-5-chloro-n-{[1-(cyclohexylmethyl)-4-piperidinyl]-methyl}-2-oxo-1,2-dihydro-3-pyridinecarboxamide Step 1. 6-Amino-5-chloro-2-(methyloxy)-N-(4-piperidinylmethyl)-3-pyridinecarboxamide A solution of 1,1-dimethylethyl 4-[({[6-amino-5-chloro-2-(methyloxy)-3-pyridinyl] carbonyl}amino)methyl]-1-piperidinecarboxylate (step 1 in example 1, 6.20 g, 15.5 mmol) in 10% methanolic hydrochloric acid (130 ml) was stirred at room temperature for 7 h. The mixture was concentrated to ca. 30 ml. The residue was basified with 2 N aqueous sodium hydroxide (pH=10) and the aqueous layer was extracted with dichloromethane (80 ml×3). The combined organic layer was dried over magnesium sulfate and concentrated in vacuo. The residue was chromatographed on a column of aminopropyl silica gel eluting with methanol/dichloromethane (1:15) to give 3.94 g (85%) of the title compound as a white solid.

MS (ESI) m/z: 299 (M+H$^+$). $^1$H-NMR (DMSO-d$_6$) δ: 7.92 (1 H, s), 7.83 (1 H, t, J=5.9 Hz), 6.88 (2 H, br s), 3.91 (3 H, s), 3.12 (2 H, t, J=6.2 Hz), 2.91 (2 H, d, J=11.9 Hz), 2.39 (2 H, br t, J= 11.9 Hz), 1.60–1.50 (3 H, m), 1.11–0.95 (2 H, m).

Step 2. 6-Amino-5-chloro-N-{[1-(cyclohexylmethyl)-4-piperidinyl]methyl}-2-(methyloxy)-3-pyridinecarboxamide A mixture of 6-amino-5-chloro-2-(methyloxy)-N-(4-piperidinylmethyl)-3-pyridinecarboxamide (step 1, 150 mg, 0.50 mmol), (bromomethyl)cyclohexane (107 mg, 0.60 mmol), and triethylamine (140 μl, 1.00 mmol) in N,N-dimethylformamide (5 ml) was stirred at 90° C. for 10 h. After cooling to room temperature, the mixture was poured into water (50 ml) and the aqueous layer was extracted with ethyl acetate/toluene (2:1, 80 ml×2). The combined organic layer was washed with brine (100 ml), dried over magnesium sulfate and concentrated in vacuo. The residue was chromatographed on a column of silica gel eluting with 25% ammonia/methanol/dichloromethane (0.1:1:20) to give 130 mg (65%) of the title compound as a yellow amorphous solid.

MS (ESI) m/z: 395 (M+H$^+$). IR (KBr) v: 3412, 3302, 2920, 2847, 1622, 1583, 1539, 1456, 1394, 1330, 1263, 1222, 1148, 984, 779, 708 cm$^{-1}$. $^1$H-NMR (CDCl$_3$) δ: 8.31 (1 H, s), 7.71 (1 H, br), 5.03 (2 H, br s), 3.99 (3 H, s), 3.31 (2 H, t, J=6.1 Hz), 2.90–2.82 (2 H, m), 2.08 (2 H, d, J=7.3 Hz), 1.90–1.15 ( 16 H, m), 0.95–0.75 (2 H, m). Anal. Calcd. for C$_{20}$H$_{31}$ClN$_4$O$_2$·0.3H$_2$O: C, 60.00; H, 7.96; N, 13.99. Found: C, 59.94; H, 7.97; N, 14.14.

Step 3. 6-Amino-5-chloro-N-{[1-(cyclohexylmethyl)-4-piperidinyl]methyl}-2-oxo-1,2-dihydro-3-pyridinecarboxamide A solution of 6-amino-5-chloro-N-{[1-(cyclohexylmethyl)-4-piperidinyl]methyl}-2-(methyloxy)-3-pyridinecarboxamide (109 mg, 0.28 mmol) in 10% methanolic hydrogen chloride (8 ml) was refluxed with stirring for 10 h. After cooling to room temperature, the solvent was removed in vacuo. The residue was suspended in methanol/tetrahydrofuran (1:3, 50 ml) and potassium carbonate (ca. 50 mg) was added to the mixture. The mixture was filtered through a pad of Celite and the filtrate was concentrated in vacuo. The residue was chromatographed on a column of aminopropyl silica gel eluting with methanol/dichloromethane (1:3) to give 69 mg (66%) of the title compound as a white solid.

MS (ESI) m/z: 381 (M+H$^+$), 379 (M–H$^-$). m.p.: 142–146° C. IR (KBr) v: 3153, 2922, 2851, 1661, 1622, 1558, 1539, 1487, 1427, 1350, 1244, 1202, 1146, 947, 702, 644 cm$^{-1}$. $^1$H-NMR (DMSO-d$_6$) δ: 9.35 (1 H, br), 7.97 (1 H, s), 7.04 (2 H, br), 3.13 (2 H, t, J=6.2 Hz), 2.80 (2 H, br d, J=10.2 Hz), 2.05 (2 H, d, J=7.3 Hz), 1.87–1.54 ( 10 H, m), 1.50–1.32 (1 H, br), 1.25–1.10 (5 H, m), 0.89–0.72 (2 H, m). Anal. Calcd. for C$_{19}$H$_{29}$ClN$_4$O$_2$·0.8H$_2$O: C, 57.73; H, 7.80; N, 14.17. Found: C, 57.73; H, 7.86; N, 14.02.

Example 14

1-(6-Amino-5-chloro-2-methoxy-3-pyridinyl)-3-(1-isobutyl-4-piperidinyl)-1-propanone Step 1. 1-(6-Amino-5-chloro-2-methoxy-3-pyridinyl)-3-(1-isobutyl-4-piperidinyl)-1-propanone The title compound was prepared according to the procedure of step 2 in the example 13 using 1-(6-amino-5-chloro-2-methoxy-3-pyridinyl)-3-(4-piperidinyl)-1-propanone and 1-iodo-2-methylpropane, instead of 1-(6-amino-2-methoxy-3-pyridinyl)-3-(4-piperidinyl)-1-propanone and 1-iodobutane.

MS (EI) m/z: 353 (M$^+$). m.p.: 128° C. IR (KBr) v: 3319, 2930, 1653, 1626, 1580, 1555, 1462, 1396, 1331, 1238, 1213, 1192 (cm$^{-1}$). $^1$H-NMR (CDCl$_3$) δ: 8.07 (1 H, s), 5.15 (2 H, br s), 3.94 (3 H, s), 2.82–2.93 (4 H, m), 2.04 (2 H, d, J=7.3 Hz), 1.54–1.86 (7 H, m), 1.20–1.30 (3 H, m), 0.89 (6 H, d, J=6.4 Hz). Anal. Calcd. for C$_{18}$H$_{28}$N$_3$O$_2$Cl: C, 61.09; H, 7.97; N, 11.87. Found: C, 61.00; H, 8.11; N, 11.72.

Example 15

6-Amino-5-chloro-3-[3-(1-isobutyl-4-piperidinyl) propanoyl]-2(1H)-pyridinone

Step 1. 6-Amino-5-chloro-3-[3-(1-isobutyl-4-piperidinyl) propanoyl]-2(1H)-pyridinone A mixture of 1-(6-amino-5-chloro-2-methoxy-3-pyridinyl)-3-(1-isobutyl-4-piperidinyl)-1-propanone (step 1 in example 15, 50 mg, 0.141 mmol) in 10% methanolic hydrochloric acid (1 ml) was refluxed for 4 h. To this mixture, concentrated hydrochloric acid (0.2 ml) was added and the mixture was refluxed for 4 h. After cooling to room temperature, the mixture was concentrated in vacuo, treated with SCX column gave brown oil. This oil was chromatographed on a column of silica gel eluting with 25% ammonium hydroxide/methanol/dichloromethane (0.1:1:10) to give pale yellow solid, which was washed with ethyl acetate to afford 19.5 mg (40%) of the title compound as pale orange solids.

MS (EI) m/z: 339 (M$^+$). m.p.: 175° C. IR (KBr) ν: 1638, 1597, 1545, 1505, 1391, 1336, 1232, 1115 (cm$^{-1}$). $^1$H-NMR (CDCl$_3$) δ: 7.85 (1 H, s), 5.51 (2 H, br s), 2.80–2.85 (2 H, m), 1.29–2.04 (14 H, m), 0.89 (6 H, d, J=6.6 Hz). Anal. Calcd. for C$_{21}$H$_{32}$N$_3$O$_2$Cl·0.32H$_2$O: C, 63.10; H, 8.23; N, 10.51. Found: C, 62.70; H, 7.55; N, 10.48.

Example 16

1-(6-Amino-2-methoxy-3-pyridinyl)-3-[1-(cyclohexylmethyl)-4-piperidinyl]-1-propanone Step 1. 1-(6-Amino-2-methoxy-3-pyridinyl)-3-[1-(cyclohexylmethyl)-4-piperidinyl]-1-propanone The title compound was prepared according to the procedure of step 2 in the example 13 using (bromomethyl)cyclohexane instead 1-iodobutane.

MS (EI) m/z: 359 (M$^+$). m.p.: 73.2° C. IR (KBr) ν: 2924, 2849, 1626, 1589, 1450, 1387, 1360, 1227 (cm$^{-1}$). $^1$H-NMR (CDCl$_3$) δ: 8.04 (1 H, d, J=8.2 Hz), 6.08 (1 H, d, J=8.4 Hz), 4.70 (2 H, br s), 3.95 (3 H, s), 2.82–2.94 (4 H, m), 2.08 (2 H, d, J=6.8 Hz), 0.83–1.86 (20 H, m). Anal. Calcd. for C$_{21}$H$_{33}$N$_3$O$_2$·0.7H$_2$O: C, 67.78; H, 9.32; N, 11.29. Found: C, 67.67; H, 9.06; N, 11.08.

Example 17

6-Amino-N-[(1-butyl-4-piperidinyl)methyl]-2-oxo-1,2-dihydro-3-pyridinecarboxamide Step 1. Methyl 6-amino-5-iodo-2-(methyloxy)-3-pyridinecarboxylate A mixture of methyl 6-amino-2-(methyloxy)-3-pyridinecarboxylate (2.1 g, 11.8 mmol) and iodine (15 g, 59 mmol) in N,N-dimethylformamide (50 ml) was stirred overnight at room temperature. The mixture was poured into water (200 ml) and extracted with ethyl acetate (50 ml×2). The combined organic layer was washed with saturated sodium bicarbonate, 20% aqueous thiosulphate and brine, dried over magnesium sulfate, and concentrated in vacuo gave a brown solid. The residue was suspended in diethyl ether and collected by filtration to afford 2.9 g (79%) of the title compound as a pale brown solid.

MS (EI) m/z: 308 (M$^+$). $^1$H-NMR (CDCl$_3$) δ: 8.38 (1 H, s), 5.19 (2 H, br s), 3.95 (3 H, s), 3.80 (3 H, s).

Step 2. 6-Amino-5-iodo-2-(methyloxy)-3-pyridinecarboxylic acid

To a solution of methyl 6-amino-5-iodo-2-(methyloxy)-3-pyridinecarboxylate (1.4 g, 4.54 mmol) in methanol (30 ml), 1M aqueous lithium hydroxide (9 ml, 9 mmol) was added and the mixture was heated at 70° C. for 2 h. After cooling to room temperature, the mixture was concentrated in vacuo to give a solid. The residual solid was dissolved in water (50 ml) and acidified (pH=5) by addition of 2N aqueous hydrochloric acid. The resultant solid was collected by filtration, washed with water and dried in vacuo under 60° C. to give 1.3 g (92%) of the title compound.

MS (ESI) m/z: 293 (M−H$^-$) $^1$H-NMR (DMSO-d$_6$) δ: 8.18 (1 H, s), 3.80 (3 H, s).

Step 3. 6-Amino-N-[(1-butyl-4-piperidinyl)methyl]-5-iodo-2-(methyloxy)-3-pyridinecarboxamide The title compound was prepared according to the procedure of step 1 in example 1 using 6-amino-5-iodo-2-(methyloxy)-3-pyridinecarboxylic acid (step 3) and (1-butyl- 4-piperidinyl)methylamine instead of 6-amino-5-chloro-2-(methyloxy)-3-pyridinecarboxylic acid and 1,1-dimethylethyl 4-(aminomethyl)-1-piperidinecarboxylate.

MS (EI) m/z: 447 (M$^+$) $^1$H-NMR (CDCl$_3$) δ: 8.62 (1 H, s), 7.67 (1 H, br s), 5.18 (2 H, br s), 3.98 (3 H, s), 3.38–3.29 (2 H, m), 2.99–2.90 (2 H, m), 2.38–2.25 (2 H, m), 1.98–1.82 (2 H, m), 1.80–1.23 (7 H, m), 0.95–0.84 (3 H, m). Anal. Calcd. for C$_{17}$H$_{27}$IN$_4$O$_2$: C, 45.75; H, 6.10; N, 12.55. Found: C, 45.53; H, 6.13; N, 12.54.

Step 4. 6-Amino-N-[(1-butyl-4-piperidinyl)methyl]-2-oxo-1,2-dihydro-3-pyridinecarboxamide A mixture of 6-amino-N-[(1-butyl-4-piperidinyl)methyl]-5-iodo-2-(methyloxy)-3-pyridinecarboxamide (step 3, 112 mg, 0.25 mmol), 2-methylimidazole (420 mg, 5 mmol), copper powder (32 mg, 0.5 mmol) and potassium carbonate (69 mg, 0.5 mmol) was heated at 140° C. for 25 min, 150° C. for 30 min and 160° C. for 45 min. After cooling, the mixture was chromatographed on a column of silica gel eluting with 25% ammonium hydroxide/methanol/dichloromethane (1:10:90) to give 35 mg (46%) of the title compound as a pale yellow solid.

MS (ESI) m/z: 307 (M+H$^+$) $^1$H-NMR (CD$_3$OD) δ: 8.18–8.09 (1 H, m), 5.78–5.69 (1 H, m), 3.40–3.23 (2 H, m), 3.20–3.02 (2 H, m), 2.59–2.48 (2 H, m), 2.30–2.18 (2 H, m), 1.90–1.79 (2 H, m), 1.78–1.24 (7 H, m), 1.01–0.92 (3 H, m). Anal. Calcd. for C$_{16}$H$_{26}$N$_4$O$_2$: C, 55.9; H, 8.20; N, 16.2. Found: C, 56.1; H, 8.06; N, 15.7.

Example 18

2'-Amino-N-[(1-butyl-4-piperidinyl)methyl]-6'-oxo-1',6'-dihydro-2,3'-bipyridine-5'-carboxamide Step 1. Bis(1,1-dimethylethyl) 5-[([(1-butyl-4-piperidinyl)methyl]{[(1,1-dimethylethyl)oxy]carbonyl}amino)carbonyl]-3-iodo-6-(methoxy)-2-pyridinylimidodicarbonate.

To a solution of 6-amino-N-[(1-butyl-4-piperidinyl)methyl]-5-iodo-2-(methyloxy)-3-pyridinecarboxamide (step 3 in example 17, 600 mg, 1.35 mmol) in dichloromethane, di-tert-butyl dicarbonate (1.18 g mg, 5.4 mmol) and 4-(dimethylamino)pyridine (165 mg, 1.35 mmol) were added at room temperature. After stirring at room temperature for 16 h, the mixture was washed with saturated aqueous sodium bicarbonate (20 ml) and dried over magnesium sulfate. After removal of solvent, the residue was chromatographed on a column of silica gel eluting with methanol/dichloromethane (5/95) to afford 642 mg (64%) of the title compound as a colorless amorphous solid.

MS (ESI) m/z: 747 (M+H$^+$). $^1$H-NMR (CDCl$_3$) δ: 8.02 (1 H, s), 3.83 (3 H, s), 3.78–3.65 (2 H, m), 2.99–2.90 (2 H, m), 2.36–2.23 (2 H, m), 1.98–1.85 (2 H, m), 1.89–1.69 (2 H, m), 1.58 (2 H, s) 1.45–1.23 (32 H, m), 0.95–0.88 (3 H, m).

Step 2. Bis(1,1-dimethylethyl) 5'-[([(1-butyl-4-piperidinyl)methyl]{[(1,1-dimethylethyl)oxy]carbonyl}amino)carbonyl]-6'-(methoxy)-2,3'-bipyridin-2'-ylimidodicarbonate.

Bis(1,1-dimethylethyl) 5-[([(1-butyl-4-piperidinyl)methyl]{[(1,1-dimethylethyl)oxy]carbonyl}amino)carbonyl]-3-iodo-6-(methoxy)-2-pyridinylimidodicarbonate. (step 1, 200 mg, 0.27 mmol), tris(dibenzylideneacetone)dipalladium (0) (15 mg, 10% mol) and tri-2-furylphosphine (12 mg, 20% mol) were added to 2-pyridylzinc bromide (0.5 M in tetrahydrofuran, 1.3 ml, 0.67 mmol) in tetrahydrofuran (20 ml) and the mixture was refluxed for 3 h. Another 2-pyridylzinc bromide (0.5 M in tetrahydrofuran, 1.3 ml, 0.67 mmol), tris(dibenzylideneacetone)dipalladium(0) (15 mg, 10% mol) and tri-2-furylphosphine (12 mg, 20% mol) were added and the mixture was refluxed overnight. The mixture was poured into water (20 ml) and extracted with dichloromethane (40 ml), washed with brine (20 m) and dried over magnesium sulfate. After removal of solvent, the residue was chromatographed on a column of silica gel eluting with 25% ammonia/methanol/dichloromethane (0.5/5/95) to afford 130 mg (67%) of the title compound as a yellow gum.

MS (ESI) m/z: 598 (M+H$^+$). $^1$H-NMR (CDCl$_3$) δ: 8.60–8.55 (1 H, m), 8.16 (1 H, s), 7.80–7.63 (2 H, m), 7.20–7.17 (1 H, m), 3.99 (3 H, s), 3.80–3.62 (2 H, m), 3.19–3.00 (2 H, m), 2.59–2.41 (2 H, m), 2.28–2.10 (2 H, m), 1.98–1.68 (2 H, m), 1.65–1.40 (21 H, m), 1.30–1.20 (16 H, m).

Step 3. 2'-Amino-N-[(1-butyl-4-piperidinyl)methyl]-6'-oxo-1',6'-dihydro-2,3'-bipyridine-5'-carboxamide Hydrogen chloride was bubbled through into a solution of bis(1,1-dimethylethyl) 5'-[ ([(1-butyl-4-piperidinyl)methyl]{[(1,1-dimethylethyl)oxy]carbonyl}amino)carbonyl]-6'-(methoxy)-2,3'-bipyridin-2'-ylimidodicarbonate. (step 2, 130 mg, 0.19 mmol) in dichloromethane (20 ml) for 1 h. The mixture was concentrated and the residue was chromatographed on a column of silica gel eluting with 25% ammonia/methanol/dichloromethane (1/10/90) to afford 26 mg (37%) of the title compound as a white solid.

MS (ESI) m/z: 384 (M+H$^+$). IR (KBr) v: 1660, 1625, 1593, 1552, 1465, 790 cm$^{-1}$. $^1$H-NMR (CDCl$_3$) δ: 9.42 (1 H, s), 8.96 (1 H, s), 8.41 (1 H, s), 7.82–7.78 (1 H, m), 7.70–7.62 (1 H, m), 7.09–7.00 (1 H, m), 3.39–3.22 (2 H, m), 3.05–2.88 (2 H, m), 2.40–2.23 (2 H, m), 2.08–1.82 (2 H, m), 1.80–1.15 (9 H, m), 0.95–0.79 (3 H, m).

Examples 19–41

The compounds disclosed hereinafter were prepared according to the following procedure.

Step 1.

To a solution of requisite commercially available alkyl or benzyl chloride (in dimethylformamide 0.35 ml, 0.120 mmol) were added (piperidinomethyl)polystyrene (86 mg), a solution of potassium iodide (0.4 ml in dimethylformamide) and a solution of 6-Amino-5-chloro-2-oxo-N-(4-piperidinylmethyl)-1,2-dihydro-3-pyridinecarboxamide (18 mg, 0.0602 mmol in dimethylformamide 0.25 ml). The mixture was stirred at 90° C. for 15 hours. (When the reaction didn't finish under this condition, the temperature was raised up to 115° C.).

To the resultant mixture was added tetrahydrofuran (1 ml) and PS-isocyanate (76 mg). The mixture was agitated at 50° C. overnight. After cooled, the regins were filtered through varian bond reservor cartridge and washed with methanol (0.5 ml).

Step 2.

The eluent was concentrated and to the residue was added 10% methanolic hydrochloric acid (1 ml). The mixture was agitated at 90° C. for 5–10 h to complete the demethylation reaction. After cooled, the solvent was removed and the residue was purified with prep. LC/MS.

HPLC/LC-MS Method

MS Condition:
ionization method: ESI positive
equipment: micromass ZMD

Analytical Conditions:

Crude products were purified using LC/MS system.
column: Waters Xttera MS C18 5 um 4.6×50 mm
column temp.: 40° C.
flow rate: 1.0 ml/min.
solvent:
A: MeOH
B: 0.1% NH$_3$ aq.

| gradient: Time (min) | A (%) | B (%) |
| --- | --- | --- |
| 0.00 | 10 | 90 |
| 2.00 | 90 | 10 |
| 4.00 | 90 | 10 |
| 4.10 | 10 | 90 |
| 6.00 | 10 | 90 |

Preparative Conditions:

Crude products were purified using LC/MS system.
column: Waters Xttera MS C18 5 um 20×50 mm
column temp.: ambient temperature
flow: 20.0 ml/min.
solvent:
A: MeOH
B: 0.1% NH$_3$ aq.

| gradient: Time (min) | A (%) | B (%) |
| --- | --- | --- |
| 0.00 | 10 | 90 |
| 1.00 | 10 | 90 |
| 4.00 | 90 | 10 |
| 5.50 | 90 | 10 |
| 5.60 | 10 | 90 |
| 7.00 | 10 | 90 |

Example 19

Ethyl 2-[4-({[(6-amino-5-chloro-2-oxo-1,2-dihydro-3-pyridinyl)-carbonyl] amino}methyl)-1-piperidinyl] butanoate Ethyl 2-bromobutanoate was used as alkyl halide.
MS (ESI) m/z: 399 (M+H$^+$)

Example 20

Ethyl 2-[4-({[(6-amino-5-chloro-2-oxo-1,2-dihydro-3-pyridinyl)-carbonyl] amino}methyl)-1-piperidinyl] hexanoate Ethyl 2-bromohexanoate was used as alkyl halide.
MS (ESI) m/z: 427 (M+H$^+$)

Example 21

Ethyl 2-[4-({[(6-amino-5-chloro-2-oxo-1,2-dihydro-3-pyridinyl)-carbonyl] amino}methyl)-1-piperidinyl] pentanoate Ethyl 2-bromopentanoate was used as alkyl halide.
MS (ESI) m/z: 413 (M+H$^+$)

Example 22

Methyl [4-({[(6-amino-5-chloro-2-oxo-1,2-dihydro-3-pyridinyl)carbonyl] amino}methyl)-1-piperidinyl](phenyl)acetate 1-Bromo-3-methoxy-1-phenylacetone was used as alkyl halide.
MS (ESI) m/z: 433 (M+H$^+$)

Example 23

Butyl 2-[4-({[(6-amino-5-chloro-2-oxo-1,2-dihydro-3-pyridinyl)carbonyl] amino}methyl)-1-piperidinyl]propanoate Butyl 2-bromopropanoate was used as alkyl halide.
MS (ESI) m/z: 413 (M+H$^+$)

Example 24

Ethyl 2-[4-({[(6-amino-5-chloro-2-oxo-1,2-dihydro-3-pyridinyl)carbonyl] amino}methyl)-1-piperidinyl]-3-methylbutanoate Ethyl 2-bromo-3-methylbutanoate was used as alkyl halide.
MS (ESI) m/z: 413 (M+H$^+$)

Example 25

6-Amino-5-chloro-2-oxo-N-{[1-(1-phenylethyl)-4-piperidinyl]-methyl}-1,2-dihydro-3-pyridinecarboxamide (1-Bromoethyl)benzene was used as alkyl halide.
MS (ESI) m/z: 389 (M+H$^+$)

Example 26

6-Amino-5-chloro-2-oxo-N-({1-[2-(trifluoromethyl)benzyl]-4-piperidinyl}methyl)-1,2-dihydro-3-pyridinecarboxamide 1-(Bromomethyl)-2-(trifluoromethyl)benzene was used as alkyl halide.
MS (ESI) m/z: 443 (M+H$^+$)

Example 27

6-Amino-5-chloro-N-({1-[5-fluoro-2-(trifluoromethyl)benzyl]-4-piperidinyl}methyl)-2-oxo-1,2-dihydro-3-pyridinecarboxamide 2-(Bromomethyl)-4-fluoro-1-(trifluoromethyl)benzene was used as alkyl halide.
MS (ESI) m/z: 461 (M+H$^+$)

Example 28

6-Amino-5-chloro-N-{[1-(2-cyanobenzyl)-4-piperidinyl]methyl}-2-oxo-1,2-dihydro-3-pyridinecarboxamide 2-(Bromomethyl)benzonitrile was used as alkyl halide.
MS (ESI) m/z: 400 (M+H$^+$)

Example 29

6-Amino-5-chloro-N-({1-[2-(1H-indol-3-yl)ethyl]-4-piperidinyl}methyl)-2-oxo-1,2-dihydro-3-pyridinecarboxamide 3-(2-Bromoethyl)-1H-indole was used as alkyl halide.
MS (ESI) m/z: 428 (M+H$^+$)

Example 30

Methyl 3-[4-({[(6-amino-5-chloro-2-oxo-1,2-dihydro-3-pyridinyl)carbonyl] amino}methyl)-1-piperidinyl]propanoate Methyl 3-bromopropanoate was used as alkyl halide.
MS (ESI) m/z: 371 (M+H$^+$)

Example 31

6-Amino-5-chloro-2-oxo-N-{[1-(2-oxo-2,3,4,5-tetrahydro-1H-1-benzazepin-3-yl)-4-piperidinyl]methyl}-1,2-dihydro-3-pyridinecarboxamide 3-Bromo-1,3,4,5-tetrahydro-2H-1-benzazepin-2-one was used as alkyl halide.

MS (ESI) m/z: 444 (M+H$^+$)

Example 32

6-Amino-5-chloro-N-({1-[4-(1,3-dioxo-1,3-dihydro-2H-isoindol-2-yl)butyl]-4-piperidinyl}methyl)-2-oxo-1,2-dihydro-3-pyridinecarboxamide 2-(4-Bromobutyl)-1H-isoindole-1,3(2H)-dione was used as alkyl halide.
MS (ESI) m/z: 486 (M+H$^+$)

Example 33

Methyl 4-[4-({[(6-amino-5-chloro-2-oxo-1,2-dihydro-3-pyridinyl)carbonyl] amino}methyl)-1-piperidinyl]butanoate Methyl 4-bromobutanoate was used as alkyl halide.
MS (ESI) m/z: 385 (M+H$^+$)

Example 34

Methyl 5-[4-({[(6-amino-5-chloro-2-oxo-1,2-dihydro-3-pyridinyl)carbonyl] amino}methyl)-1-piperidinyl]pentanoate Methyl 5-bromopentanoate was used as alkyl halide.
MS (ESI) m/z: 399 (M+H$^+$)

Example 35

6-Amino-5-chloro-N-{[1-(3-cyanopropyl)-4-piperidinyl]methyl}-2-oxo-1,2-dihydro-3-pyridinecarboxamide 4-Bromobutanenitrile was used as alkyl halide.
MS (ESI) m/z: 352 (M+H$^+$)

Example 36

6-Amino-5-chloro-N-[(1-hexyl-4-piperidinyl)methyl]-2-oxo-1,2-dihydro-3-pyridinecarboxamide 1-Bromopentane was used as alkyl halide.
MS (ESI) m/z: 369 (M+H$^+$)

Example 37

6-Amino-5-chloro-2-oxo-N-({1-[2-(1H-pyrrol-1-yl)ethyl]-4-piperidinyl}methyl)-1,2-dihydro-3-pyridinecarboxamide 1-(2-Bromoethyl)-1H-pyrrole was used as alkyl halide.
MS (ESI) m/z: 378 (M+H$^+$)

Example 38

6-Amino-5-chloro-N-({1-[2-(1H-indol-2-yl)ethyl]-4-piperidinyl}methyl)-2-oxo-1,2-dihydro-3-pyridinecarboxamide 2-(2-Bromoethyl)-1H-indole was used as alkyl halide.
MS (ESI) m/z: 428 (M+H$^+$)

Example 39

6-Amino-5-chloro-N-{[1-(2-ethoxyethyl)-4-piperidinyl]methyl}-2-oxo-1,2-dihydro-3-pyridinecarboxamide 1-Bromo-2-ethoxyethane was used as alkyl halide.
MS (ESI) m/z: 357 (M+H$^+$)

Example 40

6-Amino-5-chloro-N-({1-[3-(1,3-dioxo-1,3-dihydro-2H-isoindol-2-yl)propyl]-4-piperidinyl}methyl)-2-oxo-1,2-dihydro-3-pyridinecarboxamide 2-(3-Bromopropyl)-1H-isoindole-1,3(2H)-dione was used as alkyl halide.
MS (ESI) m/z: 472 (M+H$^+$)

Example 41

6-Amino-5-chloro-2-oxo-N-{[1-(tetrahydro-2H-pyran-2-ylmethyl)-4-piperidinyl] methyl}-1,2-dihydro-3-pyridinecarboxamide 2-(Bromomethyl)tetrahydro-2H-pyran was used as alkyl halide.
MS (ESI) m/z: 383 (M+H$^+$)

Examples 42–75

The compounds disclosed hereinafter were prepared according to the following procedure.

Step 1.
To a requisite commercially available alkyl or benzyl bromide or iodide were added a solution of triethylamine (10 mg, 0.084 mmol) and sodium iodide (7.5 mg, 0.05 mmol) in 0.3 ml in dimethylformamide, then to this reaction mixture was added a solution of 6-Amino-5-chloro-2-oxo-N-(4-piperidinylmethyl)-1,2-dihydro-3-pyridinecarboxamide (12.5 mg, 0.042 mmol in dimethylformamide 0.3 ml). The mixture was stirred at 70° C. for 15 hours.

To the resultant mixture was added dimethylformamide (0.5 ml) and PS-isocyanate (102 mg). The mixture was agitated at 50° C. overnight. After cooled to room temperature, the regins were filtered through varian bond reservor cartridge and washed with methanol (2.5 ml).

Step 2.
The eluent was concentrated and to the residue was added 10% methanolic hydrochloric acid (1 ml). The mixture was agitated at 90° C. for 5 h. After cooled to room temperature, the solvent was removed. The residue was dissolved with methanol (1 ml) and the mixture was charged onto SCX conditioninged with methanol. It was washed with methanol (3 ml) and eluted with 1 M NH$_3$-methanol (3 ml). After concentrated, the residue was purified by prep. LC/MS.

HPLC/LC-MS Method

MS Condition:
  Ionization method: ESI positive
  Equipment: micromass ZMD
  Cone Voltage: 30V Analytical Conditions:
  Column: Waters Xttera MS C18 5 um 4.6×50 mm
  Column temp.: 40° C.
  Flow rate: 1.0 ml/min.
  Solvent:
    A: MeOH
    B: 0.1% HCOOH aq.

| Gradient: Time (min) | A (%) | B (%) |
|---|---|---|
| 0.00 | 10 | 90 |
| 2.00 | 90 | 10 |
| 4.00 | 90 | 10 |
| 4.10 | 10 | 90 |
| 6.00 | 10 | 90 |

Preparative Conditions:
Crude products were purified using LC/MS system.
  Column: Waters Xttera MS C18 5 um 20×50 mm
  Column temp.: ambient temperature
  Flow rate: 20.0 ml/min.
  Solvent:
    A: MeOH
    B: 0.1% HCOOH aq.

| Gradient: Time (min) | A (%) | B (%) |
|---|---|---|
| 0.00 | 10 | 90 |
| 1.00 | 10 | 90 |
| 4.00 | 90 | 10 |
| 5.50 | 90 | 10 |
| 5.60 | 10 | 90 |
| 7.00 | 10 | 90 |

Example 42

6-Amino-5-chloro-N-[(1-heptyl-4-piperidinyl)methyl]-2-oxo-1,2-dihydro-3-pyridinecarboxamide 1-Bromoheptane was used as alkyl halide.
MS (ESI) m/z: 383 (M+H$^+$)

Example 43

6-Amino-5-chloro-2-oxo-N-[(1-propyl-4-piperidinyl)methyl]-1,2-dihydro-3-pyridinecarboxamide 1-Bromopropane was used as alkyl halide.
MS (ESI) m/z: 327 (M+H$^+$)

Example 44

Methyl 4-[4-({[(6-amino-5-chloro-2-oxo-1,2-dihydro-3-pyridinyl)carbonyl]amino}methyl)-1-piperidinyl]butanoate Methyl 4-bromobutanoate was used as alkyl halide.
MS (ESI) m/z: 385 (M+H$^+$)

Example 45

6-Amino-N-{[1-(2-bromobenzyl)-4-piperidinyl]methyl}-5-chloro-2-oxo-1,2-dihydro-3-pyridinecarboxamide 1-Bromo-2-(bromomethyl)benzene was used as alkyl halide.
MS (ESI) m/z: 453 (M+H$^+$)

Example 46

6-Amino-5-chloro-N-{[1-(2,6-dichlorobenzyl)-4-piperidinyl]-methyl}-2-oxo-1,2-dihydro-3-pyridinecarboxamide 2-(Bromomethyl)-1,3-dichlorobenzene was used as alkyl halide.
MS (ESI) m/z: 443 (M+H$^+$)

Example 47

6-Amino-5-chloro-N-{[1-(3-methylbenzyl)-4-piperidinyl]methyl}-2-oxo-1,2-dihydro-3-pyridinecarboxamide 1-(Bromomethyl)-3-methylbenzene was used as alkyl halide.
MS (ESI) m/z: 389 (M+H$^+$)

Example 48

6-Amino-5-chloro-N-{[1-(4-cyanobenzyl)-4-piperidinyl]methyl}-2-oxo-1,2-dihydro-3-pyridinecarboxamide 4-(Bromomethyl)benzonitrile was used as alkyl halide.
MS (ESI) m/z: 400 (M+H$^+$)

Example 49

Methyl 4-{[4-({[(6-amino-5-chloro-2-oxo-1,2-dihydro-3-pyridinyl)carbonyl]amino}methyl)-1-piperidinyl]methyl}benzoate Methyl 4-(bromomethyl)benzoate was used as alkyl halide.
MS (ESI) m/z: 433 (M+H$^+$)

Example 50

6-Amino-N-{[1-(4-tert-butylbenzyl)-4-piperidinyl]methyl}-5-chloro-2-oxo-1,2-dihydro-3-pyridinecarboxamide 1-(Bromomethyl)-4-tert-butylbenzene was used as alkyl halide.
MS (ESI) m/z: 431 (M+H$^+$)

Example 51

6-Amino-5-chloro-N-{[1-(3-cyanobenzyl)-4-piperidinyl]methyl}-2-oxo-1,2-dihydro-3-pyridinecarboxamide 3-(Bromomethyl)benzonitrile was used as alkyl halide.
MS (ESI) m/z: 400 (M+H$^+$)

Example 52

6-Amino-5-chloro-N-{[1-(3-chlorobenzyl)-4-piperidinyl]methyl}-2-oxo-1,2-dihydro-3-pyridinecarboxamide 1-(Bromomethyl)-3-chlorobenzene was used as alkyl halide.
MS (ESI) m/z: 409 (M+H$^+$)

Example 53

6-Amino-5-chloro-N-{[1-(2-naphthylmethyl)-4-piperidinyl]-methyl}-2-oxo-1,2-dihydro-3-pyridinecarboxamide 2-(Bromomethyl)naphthalene was used as alkyl halide.
MS (ESI) m/z: 425 (M+H$^+$)

Example 54

6-Amino-5-chloro-N-{[1-(2-chlorobenzyl)-4-piperidinyl]methyl}-2-oxo-1,2-dihydro-3-pyridinecarboxamide 1-(Bromomethyl)-2-chlorobenzene was used as alkyl halide.
MS (ESI) m/z: 409 (M+H$^+$)

Example 55

6-Amino-5-chloro-N-{[1-(4-chlorobenzyl)-4-piperidinyl]methyl}-2-oxo-1,2-dihydro-3-pyridinecarboxamide 1-(Bromomethyl)-4-chlorobenzene was used as alkyl halide.
MS (ESI) m/z: 409 (M+H$^+$)

Example 56

6-Amino-N-{[1-(3-bromobenzyl)-4-piperidinyl]methyl}-5-chloro-2-oxo-1,2-dihydro-3-pyridinecarboxamide 1-Bromo-3-(bromomethyl)benzene was used as alkyl halide.
MS (ESI) m/z: 453 (M+H$^+$)

Example 57

6-Amino-5-chloro-N-{[1-(4-methylbenzyl)-4-piperidinyl]methyl}-2-oxo-1,2-dihydro-3-pyridinecarboxamide 1-(Bromomethyl)-4-methylbenzene was used as alkyl halide.
MS (ESI) m/z: 389 (M+H$^+$)

Example 58

Methyl 3-{[4-({[(6-amino-5-chloro-2-oxo-1,2-dihydro-3-pyridinyl)carbonyl] amino}methyl)-1-piperidinyl]methyl}benzoate Methyl 3-(bromomethyl)benzoate was used as alkyl halide.
MS (ESI) m/z: 433 (M+H$^+$)

Example 59

5,6-Dichloro-N-{[1-(2-cyanobenzyl)-4-piperidinyl]methyl}-2-oxo-1,2-dihydro-3-pyridinecarboxamide 2-(Bromomethyl)benzonitrile was used as alkyl halide.
MS (ESI) m/z: 400 (M+H$^+$)

Example 60

6-Amino-5-chloro-N-{[1-(3,4-dichlorobenzyl)-4-piperidinyl] methyl}-2-oxo-1,2-dihydro-3-pyridinecarboxamide 4-(Bromomethyl)-1,2-dichlorobenzene was used as alkyl halide.
MS (ESI) m/z: 443 (M+H$^+$)

Example 61

6-Amino-5-chloro-2-oxo-N-({1-[2-(phenylthio)ethyl]-4-piperidinyl}methyl)-1,2-dihydro-3-pyridinecarboxamide

[(2-Bromoethyl)thio]benzene was used as alkyl halide.
MS (ESI) m/z: 421 (M+H$^+$)

Example 62

6-Amino-5-chloro-N-{[1-(2-ethylhexyl)-4-piperidinyl]methyl}-2-oxo-1,2-dihydro-3-pyridinecarboxamide 2-Bromoethyl phenyl sulfide was used as alkyl halide.
MS (ESI) m/z: 397 (M+H$^+$)

Example 63

6-Amino-5-chloro-2-oxo-N-{[1-(2-phenylethyl)-4-piperidinyl] methyl}-1,2-dihydro-3-pyridinecarboxamide 3-(Bromomethyl)heptane was used as alkyl halide.
MS (ESI) m/z: 389 (M+H$^+$)

Example 64

6-Amino-5-chloro-N-{[1-(5-hexenyl)-4-piperidinyl]methyl}-2-oxo-1,2-dihydro-3-pyridinecarboxamide (2-Bromoethyl)benzene was used as alkyl halide.
MS (ESI) m/z: 367 (M+H$^+$)

Example 65

6-Amino-5-chloro-2-oxo-N-{[1-(4-pentenyl)-4-piperidinyl]-methyl}-1,2-dihydro-3-pyridinecarboxamide 6-Bromo-1-hexene was used as alkyl halide.
MS (ESI) m/z: 353 (M+H$^+$)

Example 66

6-Amino-5-chloro-N-{[1-(4-methyl-3-pentenyl)-4-piperidinyl]-methyl}-2-oxo-1,2-dihydro-3-pyridinecarboxamide 5-Bromo-2-methyl-2-pentene was used as alkyl halide.
MS (ESI) m/z: 365 (M+H$^+$)

Example 67

6-Amino-5-chloro-N-{[1-(4-methylpentyl)-4-piperidinyl]methyl}-2-oxo-1,2-dihydro-3-pyridinecarboxamide 1-Bromo-4-methylpentane was used as alkyl halide.
MS (ESI) m/z: 369 (M+H$^+$)

Example 68

6-Amino-5-chloro-N-({1-[2-(1-naphthyl)ethyl]-4-piperidinyl}-methyl)-2-oxo-1,2-dihydro-3-pyridinecarboxamide 1-(2-Bromoethyl)naphthalene was used as alkyl halide.
MS (ESI) m/z: 439 (M+H$^+$)

Example 69

6-Amino-5-chloro-N-({1-[2-(4-fluorophenyl)ethyl]-4-piperidinyl}methyl)-2-oxo-1,2-dihydro-3-pyridinecarboxamide 1-(2-bromoethyl)-4-fluorobenzene was used as alkyl halide.
MS (ESI) m/z: 407 (M+H$^+$)

Example 70

6-Amino-5-chloro-N-{[1-(2-cyclohexylethyl)-4-piperidinyl]-methyl}-2-oxo-1,2-dihydro-3-pyridinecarboxamide (2-Bromoethyl)cyclohexane was used as alkyl halide.
MS (ESI) m/z: 395 (M+H$^+$)

Example 71

6-Amino-5-chloro-N-{[1-(2-methyl-2-propenyl)-4-piperidinyl]-methyl}-2-oxo-1,2-dihydro-3-pyridinecarboxamide 3-Bromo-2-methyl-1-propene was used as alkyl halide.
MS (ESI) m/z: 339 (M+H$^+$)

Example 72

6-Amino-5-chloro-N-{[1-(2-methylbutyl)-4-piperidinyl]methyl}-2-oxo-1,2-dihydro-3-pyridinecarboxamide 1-Bromo-2-methylbutane was used as alkyl halide.
MS (ESI) m/z: 355 (M+H$^+$)

Example 73

6-Amino-5-chloro-N-{[1-(2-ethoxyethyl)-4-piperidinyl]methyl}-2-oxo-1,2-dihydro-3-pyridinecarboxamide 1-Bromo-2-ethoxyethane was used as alkyl halide.
MS (ESI) m/z: 357 (M+H$^+$)

Example 74

6-Amino-5-chloro-N-{[1-(2-ethylbutyl)-4-piperidinyl]methyl}-2-oxo-1,2-dihydro-3-pyridinecarboxamide 3-(Bromomethyl)pentane was used as alkyl halide.
MS (ESI) m/z: 369 (M+H$^+$)

Example 75

6-Amino-5-chloro-2-oxo-N-{[1-(4,4,4-trifluorobutyl)-4-piperidinyl] methyl}-1,2-dihydro-3-pyridinecarboxamide 4-Bromo-1,1,1-trifluorobutane was used as alkyl halide.
MS (ESI) m/z: 395 (M+H$^+$)

Examples 76–93

The compounds disclosed hereinafter were prepared according to the following procedure.

Step 1.

To a requisite commercially available alkyl or benzyl bromide or iodide (0.05 mmol) were added a solution of triethylamine (10 mg, 0.084 mmol) and sodium iodide (7.5 mg, 0.05 mmol) in 0.5 ml in dimethylformamide. To this reaction mixture was added a solution of 6-Amino-5-chloro-2-oxo-N-(4-piperidinylmethyl)-1,2-dihydro-3-pyridinecarboxamide (12.5 mg, 0.042 mmol in dimethylformamide 0.5 ml). The mixture was stirred at 70° C. or 115° C. 15 hours. To the resultant mixture was added PS-isocyanate (102 mg). The mixture was agitated at 50° C. for 3 h. After cooled to room temperature, the regins were filtered through varian bond reservoir cartridge and washed with methanol (2.5 ml).

Step 2.

The eluent was concentrated and to the residue was added 10% methanolic hydrochloric acid (1 ml). The mixture was agitated at 90° C. for 5 h. After cooled to room temperature, the solvent was removed. The residue was dissolved with methanol (1 ml) and the mixture was charged onto SCX conditioninged with methanol. It was washed with methanol (3 ml) and eluted with 1 M NH$_3$-methanol (3 ml). After concentrated, the residue was purified by prep. LC/MS.

HPLC/LC-MS Method

MS Condition:
  Ionization method: ESI positive
  Equipment: micromass ZMD
  Cone Voltage: 30V Analytical Conditions:
  Column: Waters Xttera MS C18 5 um 4.6×50 mm
  Column temp.: 40° C.
  Flow rate: 1.0 ml/min.
  Solvent:
    A: MeOH
    B: 0.1% HCOOH aq.

| Gradient: Time (min) | A (%) | B (%) |
|---|---|---|
| 0.00 | 10 | 90 |
| 2.00 | 90 | 10 |
| 4.00 | 90 | 10 |
| 4.10 | 10 | 90 |
| 6.00 | 10 | 90 |

Preparative Conditions:
Crude products were purified using LC/MS system.
  Column: Waters Xttera MS C18 5 um 20×50 mm
  Column temp.: ambient temperature
  Flow rate: 20.0 ml/min.
  Solvent:
    A: MeOH
    B: 0.1% HCOOH aq.

| Gradient: Time (min) | A (%) | B (%) |
|---|---|---|
| 0.00 | 10 | 90 |
| 1.00 | 10 | 90 |
| 4.00 | 90 | 10 |
| 5.50 | 90 | 10 |
| 5.60 | 10 | 90 |
| 6.00 | 10 | 90 |

Example 76

6-Amino-N-[(1-benzyl-4-piperidinyl)methyl]-5-chloro-2-oxo-1,2-dihydro-3-pyridinecarboxamide (Bromomethyl)benzene was used as alkyl halide.
MS (ESI) m/z: 375 (M+H$^+$)

Example 77

6-Amino-5-chloro-2-oxo-N-{[1-(pentafluorobenzyl)-4-piperidinyl] methyl}-1,2-dihydro-3-pyridinecarboxamide 1-(Bromomethyl)-2,3,4,5,6-pentafluorobenzene was used as alkyl halide.
MS (ESI) m/z: 465 (M+H$^+$)

Example 78

6-Amino-5-chloro-N-{[1-(2,6-difluorobenzyl)-4-piperidinyl]-methyl}-2-oxo-1,2-dihydro-3-pyridinecarboxamide 2-(Bromomethyl)-1,3-difluorobenzene was used as alkyl halide.
MS (ESI) m/z: 411 (M+H$^+$)

Example 79

6-Amino-5-chloro-N-{[1-(4-fluorobenzyl)-4-piperidinyl]methyl}-2-oxo-1,2-dihydro-3-pyridinecarboxamide 1-(Bromomethyl)-4-fluorobenzene was used as alkyl halide.
MS (ESI) m/z: 393 (M+H$^+$)

Example 80

6-Amino-5-chloro-2-oxo-N-({1-[3-(trifluoromethyl)benzyl]-4-piperidinyl}methyl)-1,2-dihydro-3-pyridinecarboxamide 1-(Bromomethyl)-3-(trifluoromethyl)benzene was used as alkyl halide.
MS (ESI) m/z: 443 (M+H$^+$)

Example 81

6-Amino-5-chloro-2-oxo-N-({1-[4-(trifluoromethyl)benzyl]-4-piperidinyl}methyl)-1,2-dihydro-3-pyridinecarboxamide 1-(Bromomethyl)-4-(trifluoromethyl)benzene was used as alkyl halide.
MS (ESI) m/z: 443 (M+H$^+$)

Example 82

6-Amino-5-chloro-N-{[1-(3,4-difluorobenzyl)-4-piperidinyl]-methyl}-2-oxo-1,2-dihydro-3-pyridinecarboxamide 4-(Bromomethyl)-1,2-difluorobenzene was used as alkyl halide.
MS (ESI) m/z: 411 (M+H$^+$)

Example 83

6-Amino-N-({1-[3,5-bis(trifluoromethyl)benzyl]-4-piperidinyl}-methyl)-5-chloro-2-oxo-1,2-dihydro-3-pyridinecarboxamide 1-(Bromomethyl)-3,5-bis(trifluoromethyl)benzene was used as alkyl halide.
MS (ESI) m/z: 511 (M+H$^+$)

Example 84

6-Amino-5-chloro-N-{[1-(3,5-difluorobenzyl)-4-piperidinyl]-methyl}-2-oxo-1,2-dihydro-3-pyridinecarboxamide 1-(Bromomethyl)-3,5-difluorobenzene was used as alkyl halide.
MS (ESI) m/z: 411 (M+H$^+$)

Example 85

6-Amino-N-{[1-(4-bromo-2-fluorobenzyl)-4-piperidinyl]methyl}-5-chloro-2-oxo-1,2-dihydro-3-pyridinecarboxamide 4-Bromo-1-(bromomethyl)-2-fluorobenzene was used as alkyl halide.
MS (ESI) m/z: 471 (M+H$^+$)

Example 86

6-Amino-5-chloro-N-({1-[3-(4-fluorophenoxy)benzyl]-4-piperidinyl}methyl)-2-oxo-1,2-dihydro-3-pyridinecarboxamide 1-(Bromomethyl)-4-(4-fluorophenoxy)benzene was used as alkyl halide.
MS (ESI) m/z: 485 (M+H$^+$)

Example 87

6-Amino-5-chloro-2-oxo-N-({1-[4-(trifluoromethoxy)benzyl]-4-piperidinyl}methyl)-1,2-dihydro-3-pyridinecarboxamide 1-(Bromomethyl)-4-(trifluoromethoxy)benzene was used as alkyl halide.
MS (ESI) m/z: 459 (M+H$^+$)

Example 88

6-Amino-N-{[1-(1,1'-biphenyl-2-ylmethyl)-4-piperidinyl]methyl}-5-chloro-2-oxo-1,2-dihydro-3-pyridinecarboxamide 2-(Bromomethyl)-1,1'-biphenyl was used as alkyl halide.
MS (ESI) m/z: 451 (M+H$^+$)

Example 89

6-Amino-5-chloro-N-{[1-(3-methoxybenzyl)-4-piperidinyl]-methyl}-2-oxo-1,2-dihydro-3-pyridinecarboxamide 1-(Bromomethyl)-3-methoxybenzene was used as alkyl halide.
MS (ESI) m/z: 405 (M+H$^+$)

Example 90

6-Amino-5-chloro-N-({1-[(2'-cyano-1,1'-biphenyl-4-yl)methyl]-4-piperidinyl}methyl)-2-oxo-1,2-dihydro-3-pyridinecarboxamide 4'-(Bromomethyl)-1,1'-biphenyl-2-carbonitrile was used as alkyl halide.
MS (ESI) m/z: 476 (M+H$^+$)

Example 91

6-Amino-5-chloro-2-oxo-N-({1-[2-(trifluoromethoxy)benzyl]-4-piperidinyl}methyl)-1,2-dihydro-3-pyridinecarboxamide 1-(Bromomethyl)-2-(trifluoromethoxy)benzene was used as alkyl halide.
MS (ESI) m/z: 459 (M+H$^+$)

Example 92

6-Amino-5-chloro-N-{[1-(3,5-dimethylbenzyl)-4-piperidinyl]-methyl}-2-oxo-1,2-dihydro-3-pyridinecarboxamide 1-(Bromomethyl)-3,5-dimethylbenzene was used as alkyl halide.
MS (ESI) m/z: 403 (M+H$^+$)

Example 93

6-Amino-5-chloro-N-{[1-(2-hydroxyethyl)-4-piperidinyl]methyl}-2-oxo-1,2-dihydro-3-pyridinecarboxamide 2-Iodoethanol was used as alkyl halide.
MS (ESI) m/z: 329 (M+H$^+$)

Examples 94–97

The compounds disclosed hereinafter were prepared according to the following procedure.

Step 1.
To a requisite commercially available α-haloketone (0.05 mmol) were added a solution of triethylamine (10 mg, 0.084 mmol) in acetonitrile (0.90 ml). To this reaction mixture was added a solution of 6-amino-5-chloro-2-oxo-N-(4-piperidinylmethyl)-1,2-dihydro-3-pyridinecarboxamide (12.5 mg, 0.042 mmol in dimethylformamide 0.1 ml). The mixture was stirred at 50° C. for 3 hours. To the resultant mixture was added PS-isocyanate (102 mg). The mixture was agitated at 50° C. for 15 h. After cooled to room temperature, the regins were filtered through varian bond reservor cartridge and washed with methanol (2.5 ml).

Step 2.
The eluent was concentrated and to the residue was added 10% methanolic hydrochloric acid (1 ml). The mixture was agitated at 90° C. for 5 h. After cooled to room temperature, the solvent was removed. The residue was dissolved with methanol (1 ml) and the mixture was charged onto SCX conditioninged with methanol. It was washed with methanol (3 ml) and eluted with 1 M NH$_3$-methanol (3 ml). After concentrated, the residue was purified by prep. LC/MS.

HPLC/LC-MS Method

MS Condition:
  Ionization method: ESI positive
  Equipment: micromass ZMD
  Cone Voltage: 30V Analytical Conditions:
  Column: Waters Xttera MS C18 5 um 4.6×50 mm
  Column temp.: 40° C.
  Flow rate: 1.0 ml/min.
  Solvent:
    A: MeOH
    B: 0.1% HCOOH aq.

| Gradient: Time (min) | A (%) | B (%) |
| --- | --- | --- |
| 0.00 | 10 | 90 |
| 2.00 | 90 | 10 |
| 4.00 | 90 | 10 |
| 4.10 | 10 | 90 |
| 6.00 | 10 | 90 |

Preparative Conditions:
Crude products were purified using LC/MS system.
  Column: Waters Xttera MS C18 5 um 20×50 mm
  Column temp.: ambient temperature
  Flow rate: 20.0 ml/min.
  Solvent:
    A: MeOH
    B: 0.1% HCOOH aq.

| Gradient: Time (min) | A (%) | B (%) |
| --- | --- | --- |
| 0.00 | 10 | 90 |
| 1.00 | 10 | 90 |
| 4.00 | 90 | 10 |
| 5.50 | 90 | 10 |
| 5.60 | 10 | 90 |
| 6.00 | 10 | 90 |

Example 94

Methyl 5-[4-({[(6-amino-5-chloro-2-oxo-1,2-dihydropyridin-3-yl)carbonyl] amino}methyl)piperidin-1-yl]-3,3-dimethyl-4-oxopentanoate Methyl 5-chloro-3,3-dimethyl-4-oxopentanoate (*J. Org. Chem.*, 1965, 30, 2064–2067.) was used as α-haloketone.
MS (ESI) m/z: 441 (M+H$^+$)

Example 95

6-Amino-5-chloro-N-({1-[2-(2,4-dimethoxyphenyl)-2-oxoethyl]-piperidin-4-yl}methyl)-2-oxo-1,2-dihydropyridine-3-carboxamide 2-Bromo-1-(2,4-dimethoxyphenyl)ethanone was used as α-haloketone.
MS (ESI) m/z: 463 (M+H$^+$)

Example 96

6-Amino-5-chloro-N-{[1-(1-methyl-2-oxo-2-phenylethyl)-piperidin-4-yl]methyl}-2-oxo-1,2-dihydropyridine-3-carboxamide 2-Bromo-1-phenylpropan-1-one was used as α-haloketone.
MS (ESI) m/z: 417 (M+H$^+$)

Example 97

6-Amino-5-chloro-N-{[1-(3,3-dimethyl-2-oxobutyl)piperidin-4-yl] methyl}-2-oxo-1,2-dihydropyridine-3-carboxamide 1-Chloro-3,3-dimethylbutan-2-one was used as α-haloketone.
MS (ESI) m/z: 383 (M+H$^+$)

Example 98

6-Amino-5-chloro-N-[(1-neopentylpiperidin-4-yl)methyl]-2-oxo-1,2-dihydropyridine-3-carboxamide Step 1. 6-Amino-5-chloro-2-(methyloxy)-N-(4-piperidinylmethyl)-3-pyridinecarboxamide
To a solution of 6-amino-5-chloro-2-(methyloxy)-N-(4-piperidinylmethyl)-3-pyridinecarboxamide (step 1 in example 13, 350 mg, 1.17 mmol) in methanol (30 ml) was added pivalaldehyde (0.64 mL, 5.86 mmol), sodium cyanoborohydride (221 mg, 3.51 mmol) and acetic acid (0.01 ml, 1.29 mmol) at room temperature. The mixture was stirred for 16 h and ammoniumhydroxide (10 ml) was added slowly. Solvent was removed in vacuo and extracted with diethyl ether (30 mL×3), washed with brine (30 ml). The organic layer was dried over magnesium sulfate, and concentrated in vacuo. The residue was chromatographed on a column of silica gel eluting with 25% ammonium hydroxide/methanol/dichloromethane (0.2:1:40) to give 42 mg (10%) of the title compound as clear colorless oil.

$^1$H-NMR (CDCl$_3$) δ: 8.30 (1 H, s), 7.74 (1H, br s), 5.05 (2H, br), 3.99 (3H, s), 3.30 (2H, t, J=6.2 Hz ), 2.70–2.68 (2H, m), 2.25–2.10 (2H, m), 2.03 (2H, s), 1.70–1.30 (5H, m), 1.09 (9H, s).

Step 2. 6-Amino-5-chloro-2-(methyloxy)-N-(4-piperidinylmethyl)-3-pyridinecarboxamide The title compound was prepared according to the procedure of step 3 in the example 13 using 6-amino-5-chloro-2-(methyloxy)-N-(4-piperidinylmethyl)-3-pyridinecarboxamide instead of 6-amino-5-chloro-N-{[1-(cyclohexylmethyl)-4-piperidinyl]methyl}-2-(methyloxy)-3-pyridinecarboxamide.

MS (EI) m/z: 354 (M$^+$). IR (KBr) v: 2950, 2864, 1624, 1541, 1508,1488, 1458 (cm$^{-1}$). $^1$H-NMR (CDCl$_3$, 2 drops of DMSO-d$_6$) δ: 9.35 (1H, br s), 8.31 (1H, s), 5.78 (2H, br s), 3.27 (2H, t, J=6.2 Hz), 2.82–2.75 (2H, m), 2.19–2.10 (2H, m), 1.67–1.27 (5H, m), 0.83 (9H, s). Anal. Calcd. for C$_{17}$H$_{27}$N$_4$O$_2$Cl·0.5H$_2$O: C, 56.82; H, 7.71; N, 15.59. Found: C, 56.82; H, 7.75; N, 15.28.

Example 99

6-Amino-5-chloro-N-[(1-{1-[(methylamino)carbonyl]pentyl}-piperidin-4-yl)methyl]-2-oxo-1,2-dihydropyridine-3-carboxamide Step 1. Ethyl 2-[4-({[(6-amino-5-chloro-2-methoxypyridin-3-yl)carbonyl] amino}-methyl)piperidin-1-yl]hexanoate To a solution of 6-amino-5-chloro-2-(methyloxy)-N-(4-piperidinylmethyl)-3-pyridinecarboxamide (step 1 in example 13, 4.0 g, 13 mmol) in dimethylformamide (70 ml) was added ethyl 2-bromohexanoate (3.1 g, 14 mmol), sodium iodide (2.0 g, 13 mmol) and triethyl amine (2.2 ml) at room temperature. The mixture was heated at 70° C. overnight. After cooled to room temperature, the mixture was poured into water (80 ml) and extracted with diethyl ether (200 ml×2), washed with water (100 ml×2), brine (100 ml). The organic layer was dried over magnesium sulfate, and concentrated in vacuo. The residue was chromatographed on a column of silica gel eluting with ethyl acetate/hexane (1:1) to give 5.4 g (93%) of the title compound as a clear colorless solid.

$^1$H-NMR (CDCl$_3$) δ: 8.30 (1 H, s), 7.70 (1H, br s), 5.06 (2H, br), 4.20–4.11 (2H, m) 3.98 (3H, s), 3.31 (2H, t, J=6.4 Hz), 3.18–3.09 (1H, m), 3.00–2.80 (2H, m), 2.43–2.10 (2H, m), 1.80–1.20 (14H, m), 0.89 (3H, t, J=6.9 Hz).

Step 2. 2-[4-({[(6-Amino-5-chloro-2-methoxypyridin-3-yl) carbonyl] amino}-methyl)piperidine-1-yl]hexanoic acid To a solution of ethyl 2-[4-({[(6-amino-5-chloro-2-methoxypyridin-3-yl)carbonyl]amino}methyl)piperidin-1-yl] hexanoate (4.3 g, 9.75 mmol) in methanol (50 ml) was added 2N aqueous sodium hydroxide (9.8 ml, 19.5 mmol) and the mixture was refluxed for 12 h. After cooled to room temperature, concentrated in vacuo. The resultant solid was treated with 2N aqueous hydrochloric acid (19.5 ml) to afford white solid, which was collected by filtration, washed with water (50 ml) gave 3.8 g (94%) of the title compound as white powder.

$^1$H-NMR (DMSO-d$_6$) δ: 7.91 (1H, s), 7.87 (1H, br s), 6.90 (2H, br s), 3.91 (3H, s), 3.17–2.30 (9H, m), 1.70–1.49 (4H, m), 1.38–1.18 (5H, m), 0.92–0.80 (3H, m).

Step 3. 6-Amino-5-chloro-N-[(1-{1-[(dimethylamino)carbonyl]pentyl}piperidin-4-yl)methyl]-2-methoxynicotinamide To a solution of 2-[4-({[(6-amino-5-chloro-2-methoxypyridin-3-yl)carbonyl]amino}methyl)piperidine-1-yl]hexanoic acid (500 mg, 1.2 mmol) in dimethylformamide (30 ml) was added diethyl cyanophosphonate (300 mg, 1.8 mmol), N,N-dimethylamine hydrochloride (148 mg, 1.8 mmol) and N,N-diisopropylethylamine (0.63 ml, 3.6 mmol). The mixture was stirred for 72 h at room temperature. The mixture was concentrated in vacuo. The resultant amorphous solid was chromatographed on a column of silica gel eluting with dichloromethane/methanol (20:1) to give 55 mg (10%) of the title compound as a colorless amorphous solid.

$^1$H-NMR (CDCl$_3$) δ: 8.30 (1H, s), 7.68 (1H, br), 5.04 (2H, br), 3.98 (3H, s), 3.45–3.25 (2H, m), 3.10 (3H, s), 2.96 (3H, s), 2.90–2.70 (1H, m), 2.55–2.40 (1H, m), 2.30–2.10 (1H, m), 1.99–1.01 (13H, m), 0.88 (3H, t, J=7.0 Hz).

Step 4. 6-Amino-5-chloro-N-[(1-{1-[(methylamino)carbonyl]pentyl}piperidine-4-yl)methyl]-2-oxo-1,2-dihydropyridine-3-carboxamide The title compound was prepared according to the procedure of step 3 in the example 13 using 6-amino-5-chloro-N-[(1-{1-[(dimethylamino)carbonyl]pentyl}piperidin-4-yl) methyl]-2-methoxynicotinamide instead of 6-amino-5-chloro-N-{[1-(cyclohexylmethyl)-4-piperidinyl]methyl}-2-(methyloxy)-3-pyridinecarboxamide.

MS (ESI) m/z: 426 (M+H$^+$) IR (KBr) v: 3305, 2929, 1625, 1556, 1485, 1350, 1245 (cm$^{-1}$). $^1$H-NMR (DMSO-d$_6$) δ: 7.97 (1H, s), 6.99 (2H, br s), 3.15–3.07 (2H, m), 3.04 (3H, s), 2.86–2.65 (5H, m), 2.49–2.24 (1H, m), 2.16–2.02 (1H, m), 1.73–0.97 (13H, m), 0.84 (3H, t, J=7.2 Hz).

Example 100

6-Amino-5-chloro-2-oxo-N-({1-[1-(piperidin-1-ylcarbonyl)-pentyl] piperidin-4-yl}methyl)-1,2-dihydropyridine-3-carboxaimde Step 1. 6-Amino-5-chloro-2-methoxy-N-({1-[1-(piperidine-1-ylcarbonyl)-pentyl]piperidin-4-yl}methyl)nicotinamide The title compound was prepared according to the procedure of step 3 in the example 99 using piperidine instead of N,N-dimethylamine hydrochloride.

MS (ESI) m/z: 480 (M+H$^+$) $^1$H-NMR (CDCl$_3$) δ: 8.30 (1H, s), 7.68 (1H, br), 5.04 (2H, br), 3.98 (3H, s), 3.82–3.71 (1H, m), 3.69–3.56 (1H, m), 3.49–3.23 (5H, m), 2.90–2.73 (2H, m), 2.51–2.38 (1H, m), 2.28–2.11 (1H, m), 1.93–1.00 (18H, m), 0.88 (3H, t, J=6.8 Hz).

Step 2. 6-Amino-5-chloro-2-oxo-N-({1-[1-(piperidin-1-ylcarbonyl)pentyl]-piperidin-4-yl}methyl)-1,2-dihydropyridine-3-carboxaimde The title compound was prepared according to the procedure of step 3 in the example 13 using 6-amino-5-chloro-2-methoxy-N-({1-[1-(piperidine-1-ylcarbonyl)pentyl] piperidine-4-yl}methyl)nicotinamide instead of 6-amino-5- chloro-N-{[1-(cyclohexylmethyl)-4-piperidinyl]methyl}-2-(methyloxy)-3-pyridinecarboxamide.

MS (ESI) m/z: 466 (M+H$^+$) IR (KBr) ν: 3184, 2931, 2856, 1618, 1556, 1483, 1245 (cm$^{-1}$). $^1$H-NMR (DMSO-d$_6$) δ: 9.27 (1H, br), 7.97 (1H, s), 6.97 (2H, br), 3.75–3.50 (2H, m), 2.84–2.60 (2H, m), 2.38–2.20 (1H, m), 2.12–1.98 (1H, m). Anal. Calcd. for C$_{23}$H$_{36}$N$_5$O$_3$Cl: C, 59.28; H, 7.79; N, 15.03. Found: C, 59.45; H, 8.10; N, 14.10.

Example 101

6-Amino-5-chloro-N-{[1-(1-{[cyclohexyl(methyl)amino]-carbonyl}pentyl)piperidine-4-yl]methyl}-2-oxo-1,2-dihydropyridine-3-carboxamide Step 1. 6-Amino-5-chloro-N-{[1-(1-{[cyclohexyl(methyl)amino]carbonyl}pentyl)-piperidine-4-yl]methyl}-2-methoxynicotinamide The title compound was prepared according to the procedure of step 3 in the example 99 using N-cyclohexyl-N-methylamine instead of N,N-dimethylamine hydrochloride.

MS (ESI) m/z: 508 (M+H$^+$) $^1$H-NMR (CDCl$_3$) δ: 8.02 (1H, s), 7.68 (1H, br s), 5.30 (2H, br s), 3.97 ( 3H, s), 3.35–3.25 (3H, m), 2.98 (3H, s), 2.80–2.70 (3H, m), 2.59–2.45 (1H, m), 2.30–2.10 (1H, m), 1.94–1.00 (22H, m), 0.88 (3H, t, J=7.0 Hz).

Step 2. 6-Amino-5-chloro-N-{[1-(1-{[cyclohexyl(methyl)amino]carbonyl}pentyl)-piperidine-4-yl] methyl}-2-oxo-1,2-dihydropyridine-3-carboxamide The title compound was prepared according to the procedure of step 3 in the example 13 using 6-amino-5-chloro-N-{[1-(1-{[cyclohexyl(methyl)amino]carbonyl}pentyl)-piperidine-4-yl]methyl}-2-methoxynicotinamide instead of 6-amino-5-chloro-N-{[1-(cyclohexylmethyl)-4-piperidinyl]methyl}-2-(methyloxy)-3-pyridinecarboxamide.

MS (ESI) m/z: 494 (M+H$^+$) $^1$H-NMR (DMSO-d$_6$) δ: 9.30 (1H, br s), 7.97 (1H, s), 6.97 (2H, br s), 4.35–4.20 (1H, m), 3.90–3.75 (1H, m), 3.35 (3H, s), 3.16–3.04 (2H, m), 2.85–0.79 (28H, m). Anal. Calcd. for C$_{25}$H$_{40}$N$_5$O$_3$Cl: C, 60.77; H, 8.16; N, 14.17. Found: C, 60.86; H, 8.28; N, 13.86.

Example 102

1-{4-[3[(6-Amino-5-chloro-2-methoxypyridine-3-yl)-3-oxopropyl] piperidine-1-yl]3,3-dimethylbutan-2-one Step 1. 1-{4-[3[(6-Amino-5-chloro-2-methoxypyridine-3-yl)-3-oxopropyl]-piperidine-1-yl]3,3-dimethylbutan-2-one The title compound was prepared according to the procedure of step 1 in the example 10 using 1-chloro-3,3-dimethylbutan-2-one instead of 1-iodobutane. Then treated with equal amount of fumaric acid in methanol and concentrated in vacuo gave yellow gum solid, which was recrystallized from acetnitrile-isopropanol to afford fumarate as a white solid.

MS (ESI) m/z: 396 (M+H$^+$). m.p.: 170.9° C. IR (KBr) ν: 3323, 1724, 1661, 1618, 1636, 1580, 1553, 1430, 1394, 1234, 1190, 1121, 1047 (cm$^{-1}$). $^1$H-NMR (DMSO-d6) δ: 7.85 (1 H, s), 7.19 (2 H, br s), 6.60 (2 H, s), 3.90 (3 H, s), 2.79–2.85 (4 H, m), 2.08 (2 H, br t, J=10.4 Hz), 1.62 (2H, br d, J=9.4 Hz), 1.43–1.50 (2 H, m), 1.98 (9 H, s), 1.02–1.21 (5 H, m). Anal. Calcd. for C$_{20}$H$_{30}$N$_3$O$_4$Cl·C$_4$H$_4$O$_4$·0.1H$_2$O: C, 56.10; H, 6.71; N, 8.18. Found: C, 55.75; H, 6.67; N, 8.19.

Example 103

6-Amino-5-chloro-3-{3-[1-(3,3-dimethyl-2-oxobutyl)-piperidine-4-yl]prpanoyl}pyridin-2(1H)-one Step 1. 6-Amino-5-chloro-3-{3-[1-(3,3-dimethyl-2-oxobutyl)piperidine-4-yl] prpanoyl}pyridin-2(1H)-one The title compound was prepared according to the procedure of step 3 in the example 13 using 1-{4-[3[(6-Amino-5-chloro-2-methoxypyridine-3-yl)-3-oxopropyl] piperidine-1-yl]3,3-dimethylbutan-2-one (step 1 in example 102) instead of 6-amino-5-chloro-N-{[1-(cyclohexylmethyl)-4-piperidinyl]methyl}-2-(methyloxy)-3-pyridinecarboxamide.

MS (ESI) m/z: 382 (M+H$^+$) m.p.: 161.6° C. IR (KBr) ν: 3146, 1717, 1638, 1609, 1545, 1391, 1354, 1337, 1319, 1231 (cm$^{-1}$). $^1$H-NMR (CDCl$_3$) δ: 13.53 (1 H, br s), 7.84 (1 H, s), 5.57 (2 H, br s), 3.36 (2 H, s), 2.90 (2 H, br d, J=11.6 Hz), 2.83 (2 H, t, J=7.5 Hz), 2.00 (2 H, br t, J=11.0 Hz), 1.71–1.64(5 H, m), 1.49–1.34(2 H, m), 1.15 (9 H, s). Anal. Calcd. for C$_{19}$H$_{28}$N$_3$O$_3$Cl: C, 59.76; H, 7.39; N, 11.00. Found: C, 59.75; H, 7.58; N, 10.98.

Example 104

4-{4-[3-(6-Amino-5-chloro-2-methoxypyridin-3-yl)-3-oxopropyl] piperidin-1-yl}-2,2-dimethylpentan-3-one Step 1. 4-{4-[3-(6-Amino-5-chloro-2-methoxypyridin-3-yl)-3-oxopropyl]-piperidin-1-yl}-2,2-dimethylpentan-3-one The title compound was prepared according to the procedure of step 1 in the example 10 using 4-chloro-2,2-dimethylpentan-3-one (Ogloblin, K. A. et al., *J. Gen. Chem. USSR. (Engl. Transl.).*, 1964, 34, 1538–1542) instead of 1-iodobutane. Then treated with equal amount of fumaric acid in methanol and concentrated gave yellow solid, which was recrystallized from ethanol/diethyl ether to afford the title compound as a pale yellow amorphous solid.

IR (KBr) ν: 1710, 1579, 1558, 1461, 1394, 983 (cm$^{-1}$). $^1$H-NMR (CD$_3$OD) δ: 7.95 (1H, s), 6.69 (2H, s), 4.41–4.55 (1H, m), 3.96 (3H, s), 3.62–3.50 (1H, m), 3.26–3.14 (1H, m), 3.04–2.76 (4H, m), 2.05–1.87 (2H, m), 1.72–1.37 (7H, m), 1.25 (9H, s). Anal. Calcd. for C$_{19}$H$_{28}$N$_3$O$_3$Cl·0.2H$_2$O: C, 56.69; H, 6.93; N, 7.93. Found: C, 56.62; H, 7.13; N, 7.65.

Example 105

6-Amino-5-chloro-3-{3-[1-(1,3,3-trimethyl-2-oxobutyl-2-oxobutyl)piperidine-4-yl]propanoyl}pyridin-2(1H)-one Step 1. 6-Amino-5-chloro-3-{3-[1-(1,3,3-trimethyl-2-oxobutyl-2-oxobutyl)piperidine-4-yl]propanoyl}pyridin-2(1H)-one The title compound was prepared according to the procedure of step 3 in the example 13 using 4-{4-[3-(6-amino-5-chloro-2-methoxypyridin-3-yl)-3-oxopropyl]piperidin-1-yl}-2,2-dimethylpentan-3-one (step 1 in example 104) instead of 6-amino-5-chloro-N-{[1-(cyclohexylmethyl)-4-piperidinyl]methyl}-2-(methyloxy)-3-pyridinecarboxamide. Then treated with equal amount of fumaric acid in methanol and concentrated gave brown solid, which was recrystallized from ethanol/diethyl ether to afford the title compound as a pale brown solid.

MS (ESI) m/z: 396 (M+H⁺) m.p.: 175–185° C. IR (KBr) v: 3132, 2933, 1710, 1635, 1494, 1386 (cm⁻¹). ¹H-NMR (DMSO-d₆) δ: 7.99 (1H, br s), 7.37 (1H, br s), 6.62 (1H, s), 3.94–3.82 (1H, m), 2.93–2.75 (3H, m), 2.64–2.53 (1H, m), 2.50–2.38 (1H, m), 2.16–2.02 (1H, m), 1.72–1.55 (2H, m), 1.50–1.39 (2H, m), 1.22–1.00 (2H, m), 1.13 (9H, s), 1.06 (3H, d, J=6.6 Hz). Anal. Calcd. for $C_{19}H_{28}N_3O_3Cl \cdot 0.3H_2O$: C, 55.71; H, 6.74; N, 8.12. Found: C, 55.31; H, 6.68; N, 7.94.

Example 106

6-Amino-5-chloro-3-{3-[1-(cyclohexylmethyl)piperidine-4-yl] propanoyl}pyridin-2(1H)-one Step 1. 1-(6-Amino-5-chloro-2-methoxypyridin-3-yl)-3-[1-cyclohexylmethyl]-piperidine-4-yl]propan-1-one The title compound was prepared according to the procedure of step 1 in the example 10 using (bromomethyl)cyclohexane instead of 1-iodobutane.

MS (ESI) m/z: 394 (M+H⁺) ¹H-NMR (CDCl₃) δ: 8.10 (1H, s), 5.18 (br, 2H), 3.98 (3H, s), 3.10–2.88 (3H, m), 2.19–0.78 (23H, m)

Step 2. 6-Amino-5-chloro-3-{3-[1-(cyclohexylmethyl)piperidine-4-yl]propanoyl}pyridin-2(1H)-one The title compound was prepared according to the procedure of step 1 in the example 15 using 1-(6-amino-5-chloro-2-methoxypyridin-3-yl)-3-[1-cyclohexylmethyl]piperidine-4-yl]propan-1-one instead of 6-amino-5-chloro-3-[3-(1-isobutylpiperidin-4-yl)propanoyl] pyridin-2(1H)-one.

MS (EI) m/z: 379 (M⁺). m.p.: 164.3° C. IR (KBr) v: 3396, 3134, 2920, 2851, 1639, 1597, 1545, 1504, 1391, 1350, 1335, 1232 (cm⁻¹). ¹H-NMR (DMSO-d6) δ: 8.00 (1 H, s), 7.37 (2 H, br s), 2.89 (2 H, t, J=7.2 Hz), 2.76 (2 H, br d, J=10.1 Hz), 2.02 (2 H, br d, J=7.2 Hz), 1.80–1.60 (9 H, m), 1.48–1.42 (3 H, m), 1.21–1.08 (6 H, m), 0.85–0.74 (2 H, m). Anal. Calcd. for $C_{20}H_{30}N_3O_2Cl$: C, 63.23; H, 7.96; N, 11.06. Found: C, 62.83; H, 7.71; N, 10.93.

Example 107

1-(6-Amino-5-chloro-2-methoxypyridin-3-yl)-3-[1-(2-hydroxy-3,3-dimethylbutyl)piperidine-4-yl]propan-1-one Step 1. 1-(6-Amino-5-chloro-2-methoxypyridin-3-yl)-3-[1-(2-hydroxy-3,3-dimethylbutyl)piperidine-4-yl]propan-1-one The title compound was prepared according to the procedure of step 1 in the example 10 using 2-tert-butyloxirane instead of 1-iodobutane.

MS (ESI) m/z: 398 (M+H⁺) m.p.: 134.0° C. IR (KBr) v: 2943, 1659, 1622, 1578, 1560, 1460, 1448, 1393, 1339, 1231, 1186 (cm⁻¹). ¹H-NMR (CDCl₃) δ: 8.07 (1 H, s), 5.15 (2 H, br s), 3.95 (3 H, s), 3.32 (1 H, t, J=7.2 Hz), 3.01 (1 H, br d, J=11.0 Hz), 2.91 (2 H, t, J7.5 Hz), 2.75 (1 H, br d, J=9.9 Hz), 2.32–2.23 (3 H, m), 1.85 (1 H, dt, J=11.9 and 2.2 Hz), 1.72–1.67 (2 H, m), 1.58 (2 H, br q, J=8.3 Hz), 1.32–1.10 (3 H, m), 0.90 (9 H, s). Anal. Calcd. for $C_{20}H_{32}N_3O_3Cl$: C, 60.36; H. 8.11; N, 10.56. Found: C, 60.05; H, 8.48; N, 10.51.

Example 108

6-Amino-5-chloro-3-{3-[1-(2-hydroxy-3,3-dimethylbutyl)-piperidine-4-yl]propanoyl}pyridin-2(1H)-one Step 1. 6-Amino-5-chloro-3-{3-[1-(2-hydroxy-3,3-dimethylbutyl)piperidine-4-yl] propanoyl}pyridin-2(1H)-one The title compound was prepared according to the procedure of step 3 in the example 13 using 1-(6-amino-5-chloro-2-methoxypyridin-3-yl)-3-[1-(2-hydroxy-3,3-dimethylbutyl)piperidine-4-yl]propan-1-one (step 1 in example 107) instead of 6-amino-5-chloro-3-[3-(1-isobutylpiperidin-4-yl)propanoyl]pyridin-2(1H)-one.

MS (ESI) m/z: 384 (M+H⁺) m.p.: 211.3° C. IR (KBr) v: 3173, 2949, 1638, 1599, 1556, 1418, 1383, 1367, 1339, 1271, 1219 (cm⁻¹). ¹H-NMR (CDCl₃) δ: 7.85 (1 H, s), 5.60 (2 H, br s), 3.33 (1 H, t, J=7.2 Hz), 3.04 (1 H, br d, J=10.3 Hz), 2.86–2.76 (3 H, m), 2.32–2.25 (3 H, m), 1.90–1.12 (9 H, m), 0.9 (9 H, s). Anal. Calcd. for $C_{19}H_{30}N_3O_3Cl$: C, 59.44; H, 7.88; N, 10.95. Found: C, 59.27; H, 7.98; N, 10.67.

Example 109

1-(6-Amino-5-chloro-2-methoxypyridin-3-yl)-3-[1-(2-hydroxy-2-methylpropyl)piperidine-4-yl]propan-1-one Step 1. 1-(6-Amino-5-chloro-2-methoxypyridin-3-yl)-3-[1-(2-hydroxy-2-methylpropyl)piperidine-4-yl]propan-1-one The title compound was prepared according to the procedure of step 1 in the example 10 using 2,2-dimethyloxirane instead of 1-iodobutane.

MS (ESI) m/z: 370 (M+H⁺) m.p.: 108.1° C. IR (KBr) v: 2939, 1651, 1611, 1572, 1553, 1462, 1400, 1331, 1310, 1232, 1198, 1175 (cm⁻¹). ¹H-NMR (CDCl₃) δ: 8.07 (1 H, s), 5.16 (2 H, br s), 3.95 (3 H, s), 2.87–2.94 (4 H, m), 2.26–2.33(4 H, m), 1.55–1.68 (4 H, m), 1.27 (3 H, br s), 1.15 (6 H, s). Anal. Calcd. for $C_{18}H_{28}N_3O_3Cl$: C, 58.45; H,. 7.63; N. 11.36. Found: C, 58.55; H, 7.74; N, 11.44.

Example 110

1-{4-[3-(6-Amino-5-chloro-2-methoxypyridin-3-yl)-3-oxopropyl] piperidine-1-yl}-3-hydroxy-3-methyl-butzn-2-one Step 1. 1-{4-[3-(6-Amino-5-chloro-2-methoxypyridin-3-yl)-3-oxopropyl]-piperidine-1-yl}-3-hydroxy-3-methyl-butzn-2-one The title compound was prepared according to the procedure of step 1 in the example 10 using 1-bromo-3-hydroxy-3-methylbutan-2-one.

MS (ESI) m/z: 398 (M+H⁺) m.p.: 131–137° C. IR (KBr) v: 1728, 1654, 1616, 1579, 1458, 1392, 1226, 1190, 972 (cm⁻¹). ¹H-NMR (CDCl₃) δ: 8.07 (1 H, s), 5.85 (1H, br), 5.17 (2H, br s), 3.94 (3H, s), 3.35 (2H, s), 2.97–2.80 (4H, m), 2.15–2.05 (2H, m), 2.20–1.50 (7H, m), 1.35 (6H, m). Anal. Calcd. for $C_{19}H_{28}N_3O_4Cl$: C, 57.35; H, 7.09; N, 10.56. Found: C, 57.13; H, 7.25; N, 10.36.

What is claimed is:

1. Compounds of formula (I) and (II):

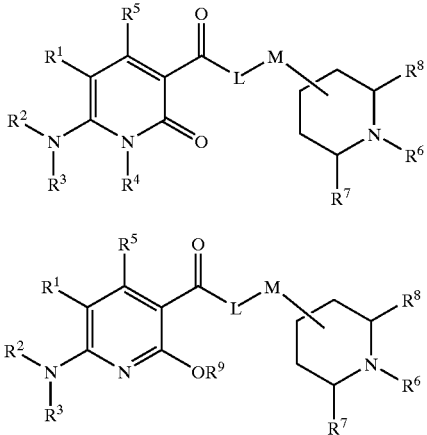

or the pharmaceutically acceptable esters thereof, and the pharmaceutically acceptable salts thereof wherein $R^1$ is hydrogen, halo, $C_{1-6}$ alkyl, aryl or heteroaryl;

$R^2$ and $R^3$ are independently hydrogen, $C_{1-6}$ alkyl, $C_{2-6}$ alkenyl, $C_{2-6}$ alkynyl, amino($C_{1-5}$)alkyl or hydroxy($C_{1-5}$)alkyl; or two of $R^2$ and $R^3$, or $R^3$ and $R^4$ taken together with the nitrogen atom to which they are attached may form a nitrogen-containing heterocycle selected from morpholino, piperazino, piperidino, pyrrolidino, azetidino, pyrazolidino, (1,2,3,4)-tetrahydroisoquinolino, or perhydroisoquinolino;

$R^4$ and $R^5$ are independently hydrogen, $C_{1-6}$ alkyl, $C_{2-6}$ alkenyl, $C_{2-6}$ alkynyl, aryl, heteroaryl or $C_{1-6}$ alkyl substituted by 1 to 6 halogen atom(s);

$R^6$ is hydrogen, $C_{1-12}$ alkyl, $C_{1-6}$ alkyl-C(=O)(CH$_2$)$_n$, $R^{11}R^{12}N(CH_2)_nC(=O)$, $C_{1-6}$ alkoxy ($C_{1-6}$)alkyl, $C_{2-8}$ alkenyl, $C_{2-6}$ alkynyl, aryl, aryl($C_{1-6}$)alkyl, aryloxy ($C_{1-6}$)alkyl, aryl ($C_{1-6}$)alkoxy ($C_{1-6}$)alkyl or $C_{1-12}$ alkyl substituted by up to 3 substituents selected from the groups consisting of halo, cyano, C(=O)R$^{10}$, NR$^{11}$R$^{12}$, R$^{11}$R$^{12}$NC(=O), NR$^{11}$SO$_2$R$^{12}$, $C_{3-8}$ cycloalkyl, $C_{1-6}$alkyl-S(O)$_m$, aryl, heteroaryl, aryl-S(O)$_m$, hydroxy, oxo and heterocyclic;

$R^7$ and $R^8$ are hydrogen;

$R^9$ is $C_{1-6}$ alkyl or $C_{3-8}$ cycloalkyl;

$R^{10}$ is $C_{1-6}$ alkyl, aryl, OR$^{11}$ or NR$^{11}$R$^{12}$;

L is (CR$^{11}$R$^{12}$)$_n$ or NR$^{11}$;

M is O, NR$^{11}$ or (CR$^{11}$R$^{12}$)$_n$;

$R^{11}$ and $R^{12}$ are independently hydrogen, $C_{1-6}$ alkyl, $C_{3-8}$ cycloalkyl or aryl($C_{1-6}$)alkyl;

n is an integer from 0 to 5; and m is an integer from 0 to 2;

said heterocyclic, aryl and heteroaryl are unsubstituted or are substituted by at least one substituent selected from the group consisting of halo, $C_{1-6}$ alkyl, amino, hydroxy, cyano, mono- or di-($C_{1-6}$)alkylamino, $C_{1-6}$ alkoxy, aryloxy, aryl ($C_{1-6}$)alkoxy, ($C_{1-6}$)alkoxy carbonyl, di-($C_{1-6}$) alkylaminocarbonyl, di-($C_{1-6}$)alkylamino ($C_{1-6}$)alkoxy, ($C_{1-6}$)alkylsulfonylamino($C_{1-6}$)alkoxy, $C_{1-6}$ alkyl substituted by 1 to 6 halogen atom(s), $C_{1-6}$ alkoxy substituted by 1 to 6 halogen atom(s), phenyl, phenoxy substituted by 1 to 5 halogen atom(s) and ($C_{1-6}$)alkoxy($C_{1-6}$)alkyl, with the proviso that when $R^9$ is $C_{1-6}$ alkyl, then L is not NR$^{11}$; and when $R^9$ is $C_{1-6}$ alkyl and L is (CR$^{11}$R$^{12}$), wherein n is 0, then M is not NR$^{11}$.

2. A compound according to claim 1, wherein $R^1$ is hydrogen, halo, $C_{1-6}$ alkyl or heteroaryl;

$R^2$ and $R^3$ are independently hydrogen or $C_{1-6}$ alkyl; or two of $R^2$ and $R^3$, or $R^3$ and $R^4$ taken together with the nitrogen atoms to which they are attached may form a nitrogen-containing heterocycle selected from morpholino, piperazino, piperidino, pyrrolidino, azetidino, pyrazolidino, (1,2,3,4)-tetrahydroisoquinolino, or perhydroisoquinolino;

$R^4$ and $R^5$ are independently hydrogen, $C_{1-6}$ alkyl, aryl, $C_{1-6}$ alkyl substituted with 1 to 6 halogen atom(s);

said aryl is unsubstituted or is substituted by at least one substituent selected from the groups consisting of halo, $C_{1-6}$ alkyl, amino, hydroxy, cyano, mono- or di-($C_{1-6}$) alkylamino, $C_{1-6}$ alkoxy, aryloxy, aryl ($C_{1-6}$)alkoxy, ($C_{1-6}$)alkoxy carbonyl($C_{1-6}$)alkoxy, di-(C1–6) alkylaminocarbonyl, di-($C_{1-6}$)alkylamino($C_{1-6}$)alkoxy, ($C_{1-6}$)alkylsulfonylamino($C_{1-6}$)alkoxy and ($C_{1-6}$) alkoxy($C_{1-6}$)alkyl;

$R^6$ is $C_{1-12}$ alkyl, $C_{3-8}$ alkenyl or $C_{1-12}$ alkyl substituted by up to 3 substituents selected from the groups consisting of C(=O)R$^{10}$, $C_{3-8}$ cycloalkyl, hydroxy, cyano, oxo, phenyl, naphthyl, phenyl-S and 5–12 membered monocyclic or bicyclic aromatic or non-aromatic ring containing 1 to 4 heteroatoms selected from O, N and S;

said phenyl, naphthyl and 5–12 membered monocyclic or bicyclic aromatic or non-aromatic ring are unsubstituted or are substituted by at least one substituent selected from the groups consisting of halo, cyano, $C_{1-6}$ alkyl, $C_{1-6}$ alkyl substituted by 1 to 6 halogen atom(s), $C_{1-6}$ alkoxy, $C_{1-6}$ alkoxy substituted by 1 to 6 halogen atom(s), mono- or di-($C_{1-6}$)alkyl amino and $C_{1-6}$ alkoxy ($C_{1-6}$)alkyl; and $R^9$ is $C_{1-6}$ alkyl;

$R^{10}$ is $C_{1-6}$alkyl, OR$^{11}$ or NR$^{11}$R$^{12}$ wherein R$^{11}$ and R$^{12}$ are independently hydrogen, C$_{3-8}$ cycloalkyl or $C_{1-6}$ alkyl;

L is (CR$^{11}$R$^{12}$)$_n$ or NR$^{11}$, wherein R$^{11}$ and R$^{12}$ are independently hydrogen or $C_{1-6}$ alkyl, and n is an integer from 0 to 3; and M is (CR$^{11}$R$^{12}$)$_n$ or NR$^{11}$, wherein R$^{11}$ and R$^{12}$ are independently hydrogen or $C_{1-6}$ alkyl, and n is an integer from 0 to 3;

said heterocyclic, aryl and heteroaryl are unsubstituted or are substituted by at least one substituent selected from the group consisting of halo, $C_{1-6}$ alkyl, amino, hydroxy, cyano, mono- or di-($C_{1-6}$)alkylamino, $C_{1-6}$ alkoxy, aryloxy, aryl ($C_{1-6}$)alkoxy, ($C_{1-6}$)alkoxy carbonyl($C_{1-6}$)alkoxy, di-(C1–6)alkylaminocarbonyl, di-($C_{1-6}$)alkylamino($C_{1-6}$)alkoxy, ($C_{1-6}$)alkylsulfonylamino($C_{1-6}$)alkoxy and ($C_{1-6}$)alkoxy($C_{1-6}$)alkyl.

3. A compound according to claim 1, wherein $R^1$ is hydrogen, halo or heteroaryl;

$R^2$ and $R^3$ are independently hydrogen or $C_{1-6}$ alkyl;

$R^4$ and $R^5$ are independently hydrogen, $C_{1-6}$ alkyl or $C_{1-6}$ alkyl substituted by 1 to 6 halogen atom(s);

$R^6$ is $C_{1-10}$ alkyl, $C_{3-8}$ alkenyl or $C_{1-10}$ alkyl substituted with up to 3 substituents selected from the groups consisting of C(=O)R$^{10}$, $C_{5-7}$ cycloalkyl, hydroxy, cyano, oxo, phenyl, naphthyl, phenyl-S, NR$^{11}$R$^{12}$ and heteroaryl selected from the groups consisting of indolyl, pyrazolyl, furyl, thienyl, oxazolyl, tetrazolyl, thiazolyl, imidazolyl, pyridyl, pyrimidinyl, pyrrolyl and quinolyl, and heterocyclic selected from the groups consisting of pyrazolino, pyrazolidino, imidazolinyl, piperidino, morpholino, thiamorpholino, pyrrolidino, piperazinyl, pyrrolidinyl, tetrahydrofuranyl, tetrahydropyranyl and phthalimidolyl;

said phenyl, naphthyl, heteroaryl and heterocyclic are unsubstituted or are substituted by at least one substituent selected from the groups consisting of halo, cyano, $C_{1-6}$ alkyl, $C_{1-6}$ alkyl substituted by 1 to 6 halogen atom(s), $C_{1-6}$ alkoxy, $C_{1-6}$ alkoxy substituted by 1 to 6 halogen atom(s), mono- or di-($C_{1-6}$)alkyl amino and $C_{1-6}$ alkoxy($C_{1-6}$)alkyl;

$R^{10}$ is $C_{1-6}$alkyl or $C_{1-6}$ alkoxy;

$R^{11}$ and $R^{12}$ are independently hydrogen, $C_{3-8}$ cycloalkyl or $C_{1-6}$ alkyl;

L is $(CR^{11}R^{12})_n$ or $NR^{11}$, wherein $R^{11}$ and $R^{12}$ are independently hydrogen or methyl, and n is an integer from 0 to 2; and M is $(CR^{11}R^{12})_n$, wherein $R^{11}$ and $R^{12}$ are independently hydrogen or methyl, and n is an integer from 0 to 2.

4. A compound according to claim 1, wherein $R^1$ is hydrogen or halo;

$R^2$ and $R^3$ are hydrogen;

$R^4$ and $R^5$ are independently hydrogen or $C_{1-6}$ alkyl;

$R^6$ is $C_{1-10}$ alkyl, $C_{3-8}$ alkenyl or $C_{1-10}$ alkyl substituted with up to 3 substituents selected from the groups consisting of C(=O)$R^{10}$, $C_{5-7}$ cycloalkyl, oxo, phenyl, naphthyl, phenyl-S, $NR^{11}R^{12}$, heteroaryl selected from the groups consisting of indolyl, furyl, thienyl, oxazolyl, pyridyl, pyrrolyl and quinolyl, and heterocyclic selected from the groups consisting of piperidino, morpholino, pyrrolidino, piperazinyl, phthalimidolyl, pyrrolidinyl and tetrahydropyaranyl;

said phenyl, naphthyl, heteroaryl and heterocyclic are unsubstituted or are substituted by at least one substituent selected from the groups consisting of halo, cyano, $C_{1-6}$ alkyl, $C_{1-6}$ alkyl substituted by 1 to 6 halogen atom(s), $C_{1-6}$ alkoxy, $C_{1-6}$ alkoxy substituted by 1 to 6 halogen atom(s), mono- or di-($C_{1-6}$)alkyl amino and $C_{1-6}$ alkoxy($C_{1-6}$)alkyl;

$R^{10}$ is $C_{1-6}$ alkoxy;

$R^{11}$ and $R^{12}$ are independently $C_{3-8}$ cycloalkyl or $C_{1-6}$ alkyl;

L is $(CR^{11}R^{12})_n$ or $NR^{11}$, wherein $R^{11}$ and $R^{12}$ are independently hydrogen or methyl, and n is an integer from 0 to 2; and M is $(CR^{11}R^{12})_n$, wherein $R^{11}$ and $R^{12}$ are independently hydrogen or methyl, and n is an integer from 0 to 2.

5. A compound according to claim 1, wherein $R^1$ is hydrogen or halo;

$R^2$ and $R^3$ are hydrogen;

$R^4$ and $R^5$ are hydrogen;

$R^6$ is $C_{1-10}$ alkyl, $C_{3-8}$ alkenyl or $C_{1-10}$ alkyl substituted with up to 3 substituents selected from the groups consisting of $C_{1-6}$ alkoxycarbonyl, $C_{5-7}$ cycloalkyl, oxo, phenyl, naphthyl, phenyl-S, heteroaryl selected from the groups consisting of indolyl and pyridyl, and heterocyclic selected from the groups consisting of pyrrolyl, piperidino, phthalimidolyl and tetrahydropyranyl;

said phenyl, naphthyl, heteroaryl and heterocyclic are unsubstituted or are substituted by at least one substituent selected from the groups consisting of halo, $C_{1-6}$ alkyl, $C_{1-6}$ alkyl substituted by 1 to 6 halogen atom(s), $C_{1-6}$ alkoxy and $C_{1-6}$ alkoxy substituted by 1 to 6 halogen atom(s);

$R^{10}$ is $C_{1-6}$alkyl;

L is $(CR^{11}R^{12})_n$ or $NR^{11}$, wherein $R^{11}$ and $R^{12}$ are independently hydrogen or methyl, and n is an integer from 0 to 2; and M is $(CR^{11}R^{12})_n$, wherein $R^{11}$ and $R^{12}$ are independently hydrogen or methyl, and n is an integer from 0 to 2.

6. A compound according to claim 1, wherein $R^1$ is hydrogen or halo;

$R^2$ and $R^3$ are hydrogen;

$R^4$ and $R^5$ are hydrogen;

$R^6$ is isobutyl, cyclohexylmethyl, n-butyl, indolylethyl, phenylethyl, fluorophenylethyl, ethoxycarbonyl(n-propyl)methyl, methoxycarbonyl(phenyl)methyl, naphthylethyl, trifuluoromethoxyphenylmethyl, n-heptyl, n-butyl(ethoxycarbonyl)methyl, (1,3-dioxo-1,3-dihydro-2H-isoindol-2-yl)propyl, isopentyl, n-hexyl, hexenyl, chlorophenylmethyl, dichlorophenylmethyl, pyrrolylethyl, ethoxycarbonyl(ethyl)methyl, cyclohexylethyl, ethoxycarbonyl(isopropyl)methyl, ethylhexyl, phenylthioethyl, methylpentyl, (1,3-dioxo-1,3-dihydro-2H-isoindol-2-yl)butyl, bromofluorophenylmethyl, butylmethyl, bromophenylmethyl, dimethoxyphenyl-oxoethyl, benzoylethyl, 3,3-dimethyl-2-oxobutyl, 1,3,3-trimethyl-2-oxobutyl-2-oxobutyl, 2-hydroxy-3,3 -dimethylbutyl, 4-methoxycarbonyl-3,3-dimethyl-2-oxo-butyl, 3,3-dimethyl-2-oxobutyl, neopentyl, [(dimethylamino)carbonyl]pentyl, (piperidinylcarbonyl)pentyl or {[cyclohexyl(methyl)amino]carbonyl}pentyl;

$R^{10}$ is $C_{1-6}$alkoxy;

L is $(CR^{11}R^{12})_n$ or $NR^{11}$, wherein $R^{11}$ and $R^{12}$ are independently hydrogen or methyl, and n is an integer from 0 to 2; and M is chemical bond or methylene.

7. A compound according to claim 1, wherein $R^1$ is hydrogen or halo;

$R^2$ and $R^3$ are hydrogen;

$R^4$ and $R^5$ are hydrogen;

$R^6$ is isobutyl, cyclohexylmethyl, n-butyl, indolylethyl, phenylethyl, fluorophenylethyl, ethoxycarbonyl(n-propyl)methyl, methoxycarbonyl(phenyl)methyl, naphthylethyl, 4-methoxycarbonyl-3,3-dimethyl-2-oxo-butyl, 3,3-dimethyl-2-oxobutyl, neopentyl, [(dimethylamino)carbonyl]pentyl, (piperidinylcarbonyl)pentyl or {[cyclohexyl(methyl)amino]carbonyl}pentyl;

$R^{10}$ is $C_{1-6}$alkoxy;

L is $NR^{11}$; and

M is chemical bond or methylene.

8. A compound selected from 6-amino-5-chloro-2-oxo-N-({1-[4-(trifluoromethoxy)benzyl]-4-piperidinyl}methyl)-1,2-dihydro-3-pyridinecarboxamide;

6-amino-5-chloro-N-[(1-heptyl-4-piperidinyl)methyl]-2-oxo-1,2-dihydro-3-pyridinecarboxamide;

ethyl 2-[4-({[(6-amino-5-chloro-2-oxo-1,2-dihydro-3-pyridinyl)carbonyl]-amino}methyl)-1-piperidinyl]hexanoate;

6-amino-5-chloro-N-({1-[3-(1,3-dioxo-1,3-dihydro-2H-isoindol-2-yl)propyl]-4-piperidinyl}methyl)-2-oxo-1,2-dihydro-3-pyridinecarboxamide;

6-amino-5-chloro-N-{[1-(3-methylbutyl)-4-piperidinyl]methyl}-2-oxo-1,2-dihydro-3-pyridinecarboxamide;

6-amino-5-chloro-N-[(1-hexyl-4-piperidinyl)methyl]-2-oxo-1,2-dihydro-3-pyridinecarboxamide;

6-amino-5-chloro-N-{[1-(5-hexenyl)-4-piperidinyl]methyl}-2-oxo-1,2-dihydro-3-pyridinecarboxamide;

6-amino-5-chloro-N-{[1-(3-chlorobenzyl)-4-piperidinyl]methyl}-2-oxo-1,2-dihydro-3-pyridinecarboxamide;

6-amino-5-chloro-N-{[1-(2,6-dichlorobenzyl)-4-piperidinyl]methyl}-2-oxo-1,2-dihydro-3-pyridinecarboxamide;

6-amino-5-chloro-2-oxo-N-({1-[2-(1H-pyrrol-1-yl)ethyl]-4-piperidinyl}methyl)-1,2-dihydro-3-pyridinecarboxamide;

ethyl 2-[4-({[(6-amino-5-chloro-2-oxo-1,2-dihydro-3-pyridinyl)carbonyl]-amino}methyl)-1-piperidinyl]butanoate;

6-amino-5-chloro-N-{[1-(2-cyclohexylethyl)-4-piperidinyl]methyl}-2-oxo-1,2-dihydro-3-pyridinecarboxamide;

ethyl 2-[4-({[(6-amino-5-chloro-2-oxo-1,2-dihydro-3-pyridinyl)carbonyl]-amino}methyl)-1-piperidinyl]-3-methylbutanoate;

6-amino-5-chloro-N-{[1-(2-ethylhexyl)-4-piperidinyl]methyl}-2-oxo-1,2-dihydro-3-pyridinecarboxamide;

6-amino-5-chloro-2-oxo-N-({1-[2-(phenylthio)ethyl]-4-piperidinyl}methyl)-1,2-dihydro-3-pyridinecarboxamide;

6-amino-5-chloro-N-{[1-(4-methylpentyl)-4-piperidinyl]methyl}-2-oxo-1,2-dihydro-3-pyridinecarboxamide;

6-amino-5-chloro-N-({1-[4-(1,3-dioxo-1,3-dihydro-2H-isoindol-2-yl)butyl]-4-piperidinyl}methyl)-2-oxo-1,2-dihydro-3-pyridinecarboxamide;

6-amino-N-{[1-(4-bromo-2-fluorobenzyl)-4-piperidinyl]methyl}-5-chloro-2-oxo-1,2-dihydro-3-pyridinecarboxamide;

6-amino-N-[(1-butyl-4-piperidinyl)methyl]-5-chloro-2-oxo-1,2-dihydro-3-pyridinecarboxamide di-hydrochloride;

6-amino-5-chloro-N-{[1-(2-methylbutyl)-4-piperidinyl]methyl}-2-oxo-1,2-dihydro-3-pyridinecarboxamide;

6-amino-N-{[1-(2-bromobenzyl)-4-piperidinyl]methyl}-5-chloro-2-oxo-1,2-dihydro-3-pyridinecarboxamide;

6-amino-N-{[1-(3-bromobenzyl)-4-piperidinyl]methyl}-5-chloro-2-oxo-1,2-dihydro-3-pyridinecarboxamide;

1-(6-amino-5-chloro-2-methoxy-3-pyridinyl)-3-(1-isobutyl-4-piperidinyl)-1-propanone;

6-amino-5-chloro-N-{[1-(cyclohexylmethyl)-4-piperidinyl]methyl}-2-oxo-1,2-dihydro-3-pyridinecarboxamide;

6-amino-5-chloro-N-({1-[2-(1H-indol-2-yl)ethyl]-4-piperidinyl}methyl)-2-oxo-1,2-dihydro-3-pyridinecarboxamide;

6-amino-5-chloro-2-oxo-N-{[1-(2-phenylethyl)-4-piperidinyl]methyl}-1,2-dihydro-3-pyridinecarboxamide;

6-amino-5-chloro-N-({1-[2-(4-fluorophenyl)ethyl]-4-piperidinyl}methyl)-2-oxo-1,2-dihydro-3-pyridinecarboxamide;

6-amino-5-chloro-N-({1-[2-(1H-indol-3-yl)ethyl]-4-piperidinyl}methyl)-2-oxo-1,2-dihydro-3-pyridinecarboxamide;

ethyl 2-[4-({[(6-amino-5-chloro-2-oxo-1,2-dihydro-3-pyridinyl)carbonyl]-amino}methyl)-1-piperidinyl]pentanoate;

methyl [4-({[(6-amino-5-chloro-2-oxo-1,2-dihydro-3-pyridinyl)carbonyl]-amino}methyl)-1-piperidinyl](phenyl)acetate;

6-amino-5-chloro-N-{[1-(2-methylpropyl)-4-piperidinyl]methyl}-2-oxo-1,2-dihydro-3-pyridinecarboxamide;

6-amino-5-chloro-N-({1-[2-(1-naphthyl)ethyl]-4-piperidinyl}methyl)-2-oxo-1,2-dihydro-3-pyridinecarboxamide;

6-amino-5-chloro-N-({1-[2-(2,4-dimethoxyphenyl)-2-oxoethyl]piperidin-4-yl}methyl)-2-oxo-1,2-dihydropyridine-3-carboxamide;

6-Amino-5-chloro-N-{[1-(1-methyl-2-oxo-2-phenylethyl)piperidin-4-yl]methyl}-2-oxo-1,2-dihydropyridine-3-carboxamide;

6-amino-5-chloro-3-{3-[1-(3,3-dimethyl-2-oxobutyl)piperidine-4-yl] propanoyl}pyridin-2(1H)-one;

6-amino-5-chloro-3-{3-[1-(1,3,3-trimethyl-2-oxobutyl-2-oxobutyl)piperidine-4-yl]propanoyl}pyridin-2(1H)-one;

6-amino-5-chloro-3-{3-[1-(cyclohexylmethyl)piperidine-4-yl]propanoyl}pyridin-2( 1H)-one;

6-amino-5-chloro-3-{3-[1-(2-hydroxy-3,3-dimethylbutyl)piperidine-4-yl]propanoyl}pyridin-2(1H)-one;

methyl 5-[4-({[(6-amino-5-chloro-2-oxo-1,2-dihydropyridin-3-yl)carbonyl]-amino}methyl)piperidin-1-yl]-3,3-dimethyl-4-oxopentanoate;

6-amino-5-chloro-N-{[1-(3,3-dimethyl-2-oxobutyl)piperidin-4-yl]methyl}-2-oxo-1,2-dihydropyridine-3-carboxamide;

6-amino-5-chloro-N-[(1-neopentylpiperidin-4-yl)methyl]-2-oxo-1,2-dihydropyridine-3-carboxamide;

6-amino-5-chloro-N-[(1-{1-[(methylamino)carbonyl]pentyl}piperidin-4-yl)methyl]-2-oxo-1,2-dihydropyridine-3-carboxamide;

6-amino-5-chloro-2-oxo-N-({1-[1-(piperidin-1-ylcarbonyl)pentyl]piperidin-4-yl}methyl)-1,2-dihydropyridine-3-carboxaimde; or 6-amino-5-chloro-N-{[1-(1-{[cyclohexyl(methyl)amino]carbonyl}pentyl)-piperidine-4-yl] methyl}-2-oxo-1,2-dihydropyridine-3-carboxamide; and salts thereof.

9. A compound selected from 1-(6-amino-5-chloro-2-methoxy-3-pyridinyl)-3-(1-isobutyl-4-piperidinyl)-1-propanone;

6-amino-5-chloro-N-{[1-(cyclohexylmethyl)-4-piperidinyl]methyl}-2-oxo-1,2-dihydro-3-pyridinecarboxamide;

6-amino-5-chloro-N-({1-[2-(1H-indol-2-yl)ethyl]-4-piperidinyl}methyl)-2-oxo-1,2-dihydro-3-pyridinecarboxamide;

6-amino-5-chloro-2-oxo-N-{[1(2-phenylethyl)-4-piperidinyl]methyl}-1,2-dihydro-3-pyridinecarboxamide;

6-amino-5-chloro-N-({1-[2-(4-fluorophenyl)ethyl]-4-piperidinyl}methyl)-2-oxo-1,2-dihydro-3-pyridinecarboxamide;

6-amino-5-chloro-N-({1-[2-(1H-indol-3-yl)ethyl]-4-piperidinyl}methyl)-2-oxo-1,2-dihydro-3-pyridinecarboxamide;

ethyl 2-[4-({[(6-amino-5-chloro-2-oxo-1,2-dihydro-3-pyridinyl)carbonyl]-amino}methyl)-1-piperidinyl]pentanoate;

methyl [4-({[(6-amino-5-chloro-2-oxo-1,2-dihydro-3-pyridinyl)carbonyl]-amino}methyl)-1-piperidinyl](phenyl)acetate;

6-amino-5-chloro-N-{[1-(2-methylpropyl)-4-piperidinyl]methyl}-2-oxo-1,2-dihydro-3-pyridinecarboxamide;

6-amino-5-chloro-N-({1-[2-(1-naphthyl)ethyl]-4-piperidinyl}methyl)-2-oxo-1,2-dihydro-3-pyridinecarboxamide;

6-amino-5-chloro-2-oxo-N-({1-[4-(trifluoromethoxy)benzyl]-4-piperidinyl}methyl)-1,2-dihydro-3-pyridinecarboxamide;

methyl 5-[4-({[(6-amino-5-chloro-2-oxo-1,2-dihydropyridin-3-yl)carbonyl]-amino}methyl)piperidin-1-yl]-3,3-dimethyl-4-oxopentanoate;

6-amino-5-chloro-N-{[1-(3,3-dimethyl-2-oxobutyl-2-oxobutyl)piperidin-4-yl]methyl}-2-oxo-1,2-dihydropyridine-3-carboxamide;

6-amino-5-chloro-N-[(1-neopentylpiperidin-4-yl)methyl]-2-oxo-1,2-dihydropyridine-3-carboxamide;

6-amino-5-chloro-N-[(1-{1-[(methylamino)carbonyl]pentyl}piperidin-4-yl)methyl]-2-oxo-1,2-dihydropyridine-3-carboxamide;

6-amino-5-chloro-2-oxo-N-({1-[1-(piperidin-1-ylcarbonyl)pentyl]piperidin-4-yl}methyl)-1,2-dihydropyridine-3-carboxaimde; or 6-amino-5-chloro-N-{[1-(1-{[cyclohexyl(methyl)amino]carbonyl}pentyl)-piperidine-4-yl] methyl}-2-oxo-1,2-dihydropyridine-3-carboxamide; and salts thereof.

10. A pharmaceutical composition comprising a compound according to any one of claims 1 to 9 and a pharmaceutically acceptable carrier.

11. A method of treating gastroesophageal reflux disease comprising administering a therapeutically effective amount of a compound according to any one of claims 1 to 9 to a mammal in need thereof.

* * * * *